United States Patent
Sheriff et al.

(10) Patent No.: US 12,390,569 B2
(45) Date of Patent: Aug. 19, 2025

(54) SIMPLIFIED REGENERATION OF APHERESIS COLUMNS

(71) Applicant: Pentracor GmbH, Hennigsdorf (DE)

(72) Inventors: Ahmed Sheriff, Berlin (DE); Birgit Vogt, Berlin (DE); Christopher Bock, Berlin (DE)

(73) Assignee: Pentracor GmbH, Hennigsdorf (DE)

( * ) Notice: Subject to any disclaimer, the term of this patent is extended or adjusted under 35 U.S.C. 154(b) by 1160 days.

(21) Appl. No.: 17/266,158

(22) PCT Filed: Aug. 1, 2019

(86) PCT No.: PCT/EP2019/070840
§ 371 (c)(1),
(2) Date: Feb. 5, 2021

(87) PCT Pub. No.: WO2020/030532
PCT Pub. Date: Feb. 13, 2020

(65) Prior Publication Data
US 2021/0308352 A1  Oct. 7, 2021

(30) Foreign Application Priority Data
Aug. 6, 2018 (EP) .................................... 18187611

(51) Int. Cl.
*A61M 1/34* (2006.01)
*B01D 15/20* (2006.01)
*B01D 15/38* (2006.01)

(52) U.S. Cl.
CPC .......... *A61M 1/3496* (2013.01); *B01D 15/203* (2013.01); *B01D 15/3804* (2013.01); *A61M 2202/0445* (2013.01)

(58) Field of Classification Search
CPC ........ A61M 1/3496; A61M 2202/0445; A61M 2205/7581; A61M 1/3679; A61M 1/3696;
(Continued)

(56) References Cited

U.S. PATENT DOCUMENTS 4,708,714 A   11/1987 Larsson et al.
6,083,187 A    7/2000 Nakayama et al.
(Continued)

FOREIGN PATENT DOCUMENTS

DE        4338858 C1 *  4/1995
WO    WO2016075269    *  5/2016

OTHER PUBLICATIONS

English translation of DE4338858C1, 11 pages. No Date.*
(Continued)

*Primary Examiner* — Pranav N Patel
(74) *Attorney, Agent, or Firm* — Amin, Turocy & Watson, LLP

(57) ABSTRACT

The present invention relates to an apheresis device (1) for the extracorporeal removal of C-reactive protein from blood of a patient, wherein the apheresis device is connectable to the blood circulation of the patient. The blood is pumped via a part of the extracorporeal circulation system (2) of the apheresis device (1) according to the invention to a cell separator (7) for separation of the blood into blood plasma and cellular components. Via a first outlet of the cell separator (7), the separated blood plasma is directed by means of a plasma line (8A) to an apheresis column (4) for affinity chromatographic removal of C-reactive protein from the blood plasma. After removal of the C-reactive protein from the blood plasma of the patient, said now treated blood plasma is combined with the cellular components of the blood via a plasma line (8B). Furthermore, the apheresis device (1) according to the invention comprises a bypass line (12), which leads from the plasma line (8A) into the plasma line (8B) while bypassing the apheresis column (4). The apheresis device (1) according to the invention also comprises a regeneration line (14), which runs into the plasma line (8A) or directly into the apheresis column (4).

14 Claims, 9 Drawing Sheets

(58) Field of Classification Search
CPC ........ A61M 2205/7554; A61M 1/3486; A61M 2202/0057; B01D 15/203; B01D 15/3804
See application file for complete search history.

(56) References Cited

U.S. PATENT DOCUMENTS

| | | | |
|---|---|---|---|
| 2004/0024342 A1* | 2/2004 | Weitzel | A61M 1/3603 435/284.1 |
| 2009/0196938 A1 | 8/2009 | Vogt | |
| 2012/0323158 A1* | 12/2012 | Tebbey | A61M 1/362 604/6.01 |
| 2013/0248450 A1* | 9/2013 | Kenley | A61M 1/3633 210/96.1 |
| 2014/0291248 A1 | 10/2014 | Foley et al. | |
| 2017/0319982 A1* | 11/2017 | Sheriff | B01J 20/3204 |
| 2018/0264186 A1* | 9/2018 | Van Bruggen | A61M 1/3633 |

OTHER PUBLICATIONS

International Search Report and Written Opinion for International Patent Application No. PCT/EP2019/070840 dated Oct. 9, 2019, 19 pages.

* cited by examiner

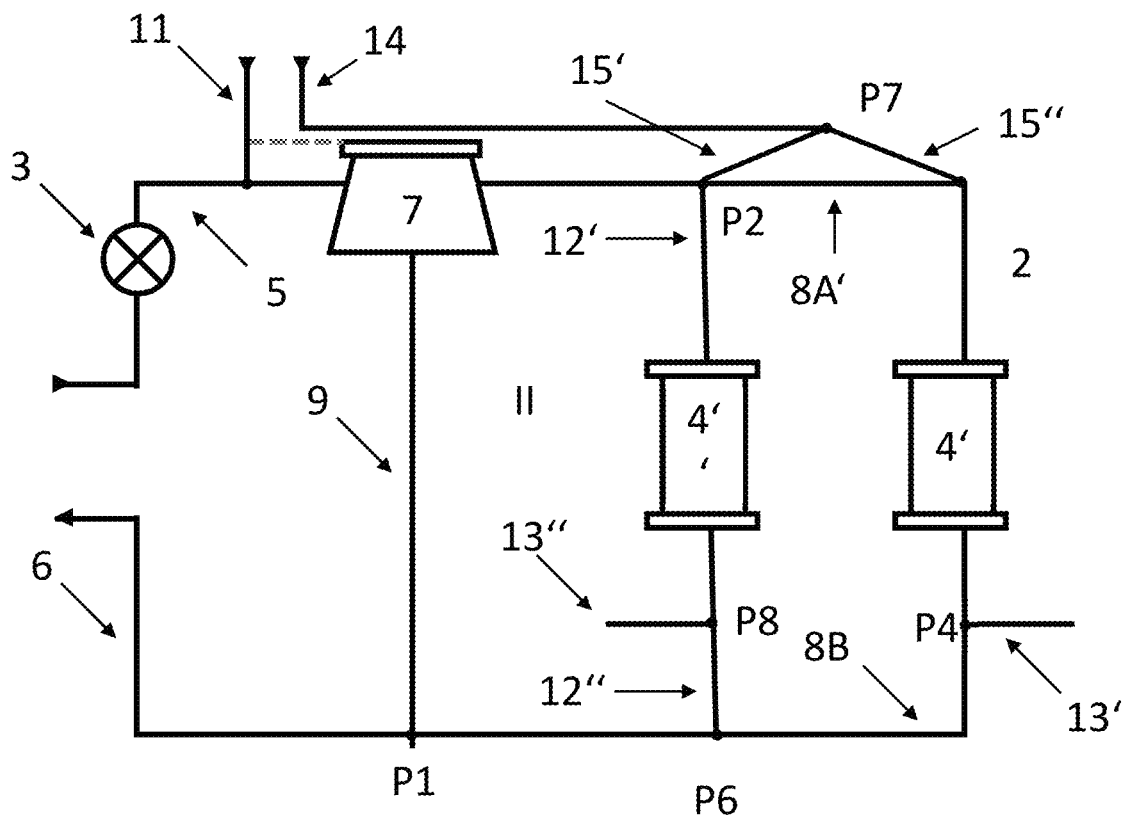
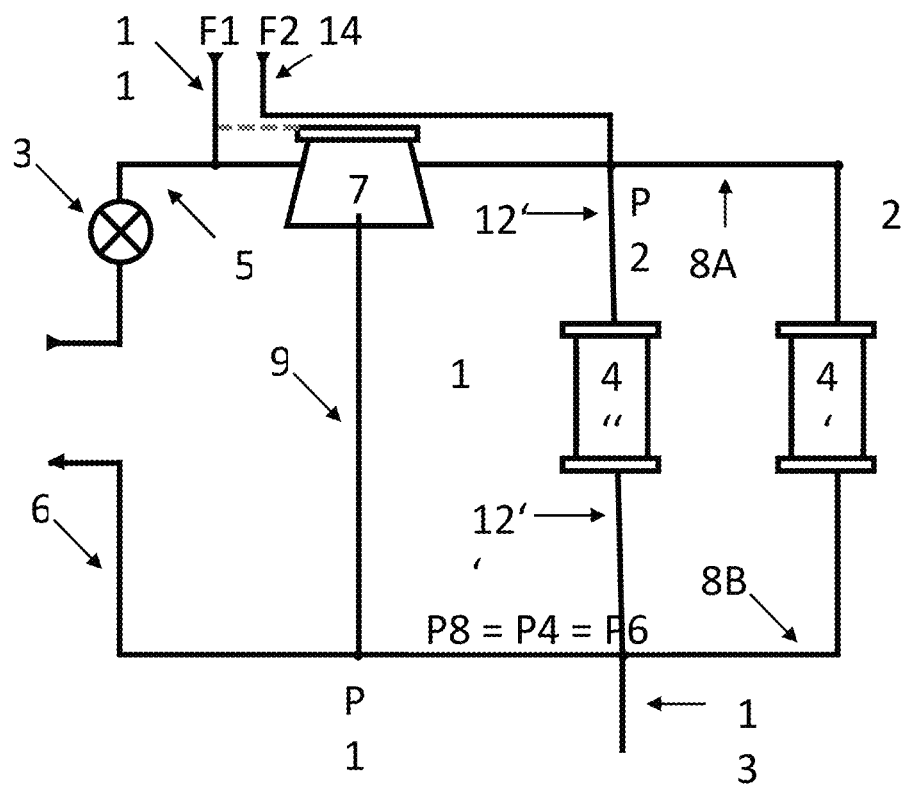

SIMPLIFIED REGENERATION OF APHERESIS COLUMNS

The present invention relates to an apheresis device (1) for the extracorporeal removal of C-reactive protein from blood of a patient, wherein the apheresis device is connectable to the blood circulation of the patient. The blood is pumped via a part of the extracorporeal circulation system (2) of the apheresis device (1) according to the invention to a cell separator (7) for separation of the blood into blood plasma and cellular components. Via a first outlet of the cell separator (7), the separated blood plasma is directed by means of a plasma line (8A) to an apheresis column (4) for affinity chromatographic removal of C-reactive protein from the blood plasma. After the removal of the C-reactive protein from the blood plasma of the patient, said now treated blood plasma is combined with the cellular components of the blood via a plasma line (8B). Furthermore, the apheresis device (1) according to the invention comprises a bypass line (12), which leads from the plasma line (8A) into the plasma line (8B) while bypassing the apheresis column (4). The apheresis device (1) according to the invention also comprises a regeneration line (14), which runs into the plasma line (8A) or directly into the apheresis column (4).

In addition, the present invention comprises a method for simplified regeneration of an apheresis column.

BACKGROUND OF THE INVENTION

According to the World Health Organization (WHO) approx. 17,000,000 people died from cardiovascular diseases in the year 2008. This makes cardiovascular diseases the most common cause of death among noncommunicable diseases and is responsible for about one-third of all deaths worldwide each year. According to estimates, this number will increase to approximately 23,000,000 deaths per year until the year 2030.

Thus, cardiovascular diseases are and will remain not only the main cause of death worldwide, but also cause enormous medical costs for the national health systems and health insurances. Two of the most common and most damaging manifestations of cardiovascular diseases are the occurrence of arteriosclerosis and thrombosis, which in turn are inter alia causal for heart attacks and strokes.

Great progress has been achieved in the treatment of cardiovascular diseases in the last years. This progress has been made possible not only by growing understanding regarding the disease-causing mechanisms, but also by the early identification of patient at risk. Indeed, the identification of disease risks and early treatment thereof are important features of modern medical practice. Over the last 25 years, a variety of factors and clinical parameters have been identified that correlate either with the current state of disease or with the future likelihood of a cardiovascular disease. Such risk factors can be measurable biochemical or physiological parameters such as levels of serum cholesterol, HDL, LDL and fibrinogen, but may also include behaviour patterns such as overweight and smoking. In cases where a risk factor not merely indicative of a disease or its development, but is actually causally involved in its development, a therapeutic influence of said risk factor can affect the course of disease or can reduce the risk of its development.

As an acute phase protein, CRP is part of the innate immune system and is formed in the liver in the course of inflammatory reactions and released into the blood. The formation of C-reactive protein (CRP) is primarily induced by cytokines, which are expressed in the course of an acute or chronic inflammatory reaction. The strongest stimulus for the formation of CRP is interleukin-6 (IL-6). Therefore, the levels of CRP as well as IL-6 in the blood are indicators of a local or systemic inflammatory reaction. Chronic inflammation is presumed to be one of the underlying and supporting pathological occurrences in cardiovascular diseases. Here, it is increasingly assumed, that CRP is not only predicative for cardiovascular disease, but also causally involved in its development or can affect its course.

Yeh (*Clin Cardiol.*, 2005, 28:408-412) shows that the CRP level can be used to predict the cardiovascular disease risk, CRP is moreover an indicator of inflammatory reactions and that inflammation promotes all stages of atherosclerosis. Zoccali et al., (*Semin. Nephrol.*, 2005, 25:358-362) show that CRP level is predictive of cardiovascular mortality risk in patients with end stage renal disease. According to Nurmohamed et al., (*Neth. J. Med.*, 2005, 63:376-381) CRP level is predictive of cardiovascular mortality risk in hemodialysis patients.

Sola et al., (*J. Card. Fail.*, 2005, 11:607-612) could show that statin therapies can be used to lower the amount of CRP and thus reduce mortality and morbidity caused by cardiovascular disease. However, this form of therapy is not sufficient to significantly reduce high amounts of CRP (up to 1000-fold above normal level) that occur after a heart attack or high amounts of CRP in the blood of dialysis patients.

Slagman et al. 2011 (Specific Removal of C-Reactive Protein by Apheresis in a Porcine Cardiac Infarction Model, Blood Purif 2011; 31:9-17), Sheriff et al. 2014 (C-Reactive Protein-Adsorber therapies: new ideas and concepts; LECTURE NOTES OF THE ICB SEMINAR: ADVANCES IN MEMBRANE AND ADSORBER TECHNOLOGY IN LIFE SCIENCES, Warsaw, April 2014), Sheriff et al. 2015 (Selective Apheresis of C-Reactive Protein: A New Therapeutic Option in Myocardial Infarction? Journal of Clinical Apheresis 30:15-21 (2015))

Consequently, there is increasing interest in therapeutic methods for reduction of CRP levels in the blood of patients.

WO 90/12632 discloses a method and a device for extracorporeal treatment of biological fluids with the aim of removal of CRP as well as anti-phosphocholine antibodies from these biological fluids for the treatment of cancer. The phosphocholine containing matrix used for this purpose can consist, for example, of silica, Sepharose, acrylic beads or agarose, wherein both CRP and anti-phosphocholine antibodies are bound by the phosphocholine contained.

WO 2007/076844 discloses a method by extracorporeal CRP removal from blood plasma by apheresis to reduce the risk to a patient caused by an elevated CRP level in the blood. According to the invention a column containing a matrix to which phosphocholine derivates are bound is used for this purpose in order to bind and remove CRP from plasma and thus to treat and/or prevent autoimmune diseases, cardiovascular diseases, diabetes as well as renal insufficiency.

The normal level of CRP in the blood of humans varies from person to person but is on average about 0.8 mg CRP per liter of blood, but can rise well over 100 mg CRP per liter of blood in the case of acute or chronic inflammatory reactions (e.g., bacterial infections, atherosclerosis, after a heart attack). Since the half-life of CRP in the blood (approx. 19 hours) is constant and thus independent of state of health of the patient, the synthesis rate of CRP alone is responsible for the regulation of the CRP level in the blood (Pepys & Hirschfield, *J. Clin. Invest.*, 2003, 111:1805-1812). Consequently, the greatly increased synthesis of CRP in acute pathological conditions places special demands on therapeutic approaches to CRP removal from patients (high-risk or acute patients) since a substantial amount of CRP must be removed to reduce blood CRP levels to normal levels. Thus, there is a need for particularly efficient devices for CRP removal from blood of patients.

DE 102005061715 A1 discloses a method for treatment of the risk of elevated amounts of C-reactive protein (CRP) by performing an extracorporeal perfusion of blood plasma through a device such as a column, which contains adsorbent matrix material, including lipids, peptides, polypeptides, phosphocholine (PC) or PC derivatives, to remove C-reactive protein. The ability for regeneration of the column is not disclosed.

Reusable adsorbers are known from the prior art, which consist of a housing filled with a carrier substance and a binding factor coupled to it. Reusable adsorbers are generally regenerable, since after plasma, whose amount depends on the concentration substance to be adsorbed, has passed through, the adsorber is "saturated" and binding of the substance can no longer take place. Thereby, the adsorber is rinsed free of the bound substances with various regeneration solutions and thus prepared again for a new plasma charge. The permissible number of regenerations is specified by the manufacturers. The reusable adsorber may only be used on one and the same patient. To prevent germ growth in the adsorbers, they must be filled with a preservative fluid at the end of each treatment, which must be rinsed out before each new therapy. However, significant costs could be saved by reusing them. The operation of the existing devices (combination of two or more medical devices) is overly complex and highly demanding. In addition, the devices are rarely used overall.

DE 102005019406 A1 discloses a method and a device for the automatic discharge of rinsing fluid during an apheresis treatment. Also disclosed is the use of auxiliary devices, whereby two adsorbers are alternately and repeatedly loaded and rinsed. These auxiliary devices have their own peristaltic pumps, peristaltic clamps and control elements. While these prior art devices and methods are efficient, a disadvantage of them is the simultaneous operation of two devices, which, as mentioned above, are not regularly used due to their complexity. According to the disclosure of DE 102005019406 A1, the objective was to reduce switching operations between fluid discharge and fluid recirculation during treatment to enable direct adsorber operation without an additional device on a cell separator. In this context, DE 102005019406 A1 teaches a combination of collecting containers and check valves to enable, for example, a changeover of the loading from a first adsorber to the second adsorber by means of a 3-way valve in the feeding tube system. Thus, DE 102005019406 A1 teaches an alternative device with two apheresis columns. The disadvantage of increased costs due to the second apheresis column, which again can only be used with one and the same patient, is not eliminated by the disclosure of DE 102005019406 A1.

WO 2012/143103 discloses a device for extracorporeal blood treatment and for monitoring the fluid flow therein, wherein the fluid flow is switched between treatment mode and filling and rinsing mode by means of a changeover clamp. During the filling and rinsing mode, the rinsing solution is collected in a collection bag, and during the treatment mode, it is necessary to ensure that the purified plasma does not enter the collection bag. Therefore, monitoring of the correct function of the exchange clamp is required. Monitoring of the fluid flow takes place by detecting a change in the weight of the collection bag. An evaluation unit for monitoring the change in the weight of the collection bag is taught as an additional feature in WO 2012/143103, and contributes to the complex structure of the disclosed subject matter. The skilled personnel operating the disclosed device must measure a predetermined time interval such that the tube lines of the fluid system can be filled completely with rinsing liquid. Only when the tube lines of the fluid system are completely filled with fluid, the weight of the collection bag can be expected to increase. Here, the skilled personnel must pay attention to different acoustic and/or optical signals generated by the control unit. Consequently, the device taught in WO 2012/143103 represents a very high training effort for the clinical staff. Furthermore, although WO 2012/143103 discloses a blood treatment unit (10) having one or more filters or adsorbers, it does not disclose with which fluids the blood treatment unit is regenerated, nor whether the plasma flow is interrupted during regeneration. Thus, the presence of a bypass line is neither taught nor suggested by WO 2012/143103.

DE 4338858 C1 also discloses a device for the regeneration of an apheresis column. DE 4338858 C1 teaches the use of a reservoir in which the plasma is temporarily stored during the regeneration of the apheresis column. The regeneration of the apheresis column takes place via the combination of glycine, NaCl solution and PBS known from the prior art. Consequently, the teaching of DE 4338858 C1 does not contain any reference regarding the use of the anticoagulation solution or the rinsing solution of the plasma separator as regeneration solution for the apheresis column, according to the device of the invention. Furthermore, DE 4338858 C1 does not disclose a bypass line that allows the plasma flow to be diverted bypassing the apheresis column during the regeneration of the latter.

International patent application WO2012141697 A1 discloses an apheresis device for extracorporeal removal of CRP from blood. Regeneration of the apheresis column during apheresis without stopping the treatment is not described.

European patent application EP 0834329 A1 is directed to a device for removing cholesterol from blood. No specific columns or column materials are mentioned therein. The removal of CRP is not taught. Columns for affinity chromatographic removal of cholesterol do not exist. Basically, cholesterol is removed via lipoprotein apheresis. Columns are used that are only partially selective for LDL cholesterol, i.e. LDL cholesterol binds with higher affinity to the matrix in the apheresis column than other substances present in the blood. Very well, however, other substances are removed from the blood or blood plasma with a high percentage. The columns disclosed in EP 0834329 A1 are not suitable for selective removal of CRP from blood. European patent application EP 0111696 A2 discloses a device for the removal of anti-factor VII or IX antibodies. The removal of CRP is not taught. Therefore, in particular, apheresis columns for affinity chromatographic removal of CRP are not disclosed, i.e., that CRP does not bind with higher affinity to the matrix in the apheresis column than other substances present in the blood, but that there is specificity for antibodies. The columns disclosed in EP 0834329 A1 are not suitable for selective removal of CRP from blood.

It is the object of the present invention to provide a device for simplified regeneration of apheresis columns while minimizing the stated disadvantages of the devices known from the prior art. In other words, the object of the present invention is to provide a device for simplified regeneration of apheresis columns and, in particular, an apheresis column for selective removal of CRP from blood, which can be operated with reduced training effort, and thus with reduced personnel effort and reduced overall costs.

This task is solved by the teachings of the independent claims. Further advantageous embodiments result from the description, the examples and the pending claims.

Surprisingly, it was found that by providing a regeneration line which either runs directly into the apheresis column or runs into the plasma line before the apheresis column but after the bypass line, a simplified regeneration of the apheresis column is made possible while minimizing the disadvantages known from the prior art.

DESCRIPTION OF THE INVENTION

The present invention relates to an apheresis device (1) for extracorporeal removal and preferably for extracorporeal selective removal of CRP from blood of a patient, wherein the apheresis device is connectable to the blood circulation of the patient. The blood is pumped via a part of the extracorporeal circulation system (2) of the apheresis device (1) according to the invention to a cell separator (7) for separation of the blood into blood plasma and cellular components. Via a first outlet of the cell separator (7), the separated blood plasma is directed by means of a plasma line (8A) to an apheresis column (4) for affinity chromatographic removal of CRP from the blood plasma. After the removal and preferably after selective removal of the CRP from the blood plasma of the patient, said, now treated, blood plasma is combined with the cellular components of the blood via a plasma line (8B). Furthermore, the apheresis device (1) according to the invention comprises a bypass line (12), which leads from the plasma line (8A) into the plasma line (8B) while bypassing the apheresis column (4). Further, the apheresis device (1) according to the invention comprises a regeneration line (14), which runs into the plasma line (8A) in the direction of flow at or after, preferably after the bypass line (12) or directly into the apheresis column (4).

In addition, the present invention comprises a method for simplified regeneration of an apheresis column.

Device

The present invention relates to an apheresis device (1) for extracorporeal removal of CRP from blood comprising:
  an extracorporeal circulation system (2) for blood,
  means (3) for generation and regulation of a flow of blood in the extracorporeal circulation system (2),
  a cell separator (7) for separation of the blood into blood plasma and cellular components, at least one apheresis column (4) for affinity chromatographic removal of CRP from blood, wherein the extracorporeal circulation system (2) comprises an arterial line (5) to the cell separator (7), a plasma line (8A) from the cell separator (7) to the apheresis column (4), a plasma line (8B) for CRP-depleted blood plasma from the apheresis column (4) to a point (P1), a cell line (9) for the separated cellular components from the cell separator (7) to the point (P1) and a venous line (6) starting from the point (P1),
  a central processing unit (10) for controlling the apheresis device (1),
  at least one connection line (11) for connection of at least one liquid container (F) to the arterial line (5) or the cell separator (7),
  characterized in that
  a bypass line (12) branches off from the plasma line (8A) and runs into the plasma line (8B),
  a waste line (13) goes off directly from the apheresis column (4) or from the plasma line (8B) in the direction of flow before the junction of the bypass line (12), and
  at least one regeneration line (14) which goes off from the at least one liquid container (F) or from the at least one connection line (11) and leads to the plasma line (8A) in the direction of flow at or after the branch of the bypass line (12) or runs directly into the apheresis column (4).

As explained above, the apheresis device (1) according to the invention for extracorporeal removal of CRP from blood is connectable to the blood circulation of a patient. From a vascular access on the patient (usually a venous access), the blood is pumped to a cell separator (7) via a part of the extracorporeal circulation system (2) of the apheresis device (1) according to the invention. The part of the extracorporeal circulation system (2) that directs the blood out of the patient and to the cell separator (7), directs the blood away from the patient and thus away from the patient's heart and is therefore referred to as "arterial line" (5) in reference to vascular nomenclature in the human body.

The blood of the patient is directed through an inlet of the cell separator (7) into the cell separator (7) and is separated by the latter into blood plasma (sometimes also referred to simply as "plasma") and the cellular components of the blood. Thereby, it must be taken into account that the separation into blood plasma and cellular components is not performed completely, but merely preferably 10 to 90% of the total blood plasma is separated from the cellular components. Via a first outlet of the cell separator (7), the separated blood plasma is directed via a plasma line (8A) to the apheresis column (4) for affinity chromatographic removal of CRP from the blood (or from the blood plasma). After removal or reduction of CRP in the blood plasma of the patient, said now treated blood plasma (also referred to as "depleted blood plasma") is directed to a point (P1) via a plasma line (8B). Via a second outlet of the cell separator (7) and a connecting line (the so-called cell line (9)), the cellular components of the blood bypass the apheresis column (4) and are directed to point (P1). There, the cellular components are combined with the depleted blood plasma. After combining the cellular components with the depleted blood plasma, the now treated blood is led back to the patient via a further part of the extracorporeal circulation system (2) of the present invention. The part of the extracorporeal circulation system (2) which directs the treated blood from the point (P1) of the extracorporeal circulation system (2) back to the patient, directs the blood to the patient and thus also to the patient's heart and is therefore referred to as "venous line" (6) in reference to vascular nomenclature in the human body.

In an alternative embodiment of the present invention, it is also possible that the cellular components are fed back to the patient directly after the separation from the plasma via the second outlet of the cell separator and a connecting line, and merely the treated plasma is fed back to the patient via the venous line.

In order to be able to prevent coagulation of the blood in the extracorporeal circulation system or to enable flushing or pre-rinsing of the extracorporeal circulation system (e.g. with a physiological saline solution), the apheresis device according to the invention comprises at least one line (the so-called connection line (11)) that enables the connection of at least one liquid container (F) und thus the feeding of the liquid (e.g. a anticoagulation agent or a physiological saline solution) contained in the fluid container (F) into the extracorporeal circulation system. In this context it is also referred to that the connection line (11) for connection of at least one liquid container (F) is in fluidic connection with the extracorporeal circulation system, i.e. a liquid from a liquid container can be introduced into the extracorporeal circulation system via the connection line (11). In preferred embodiments of the present invention, the at least one connection line (11) runs into the extracorporeal circulation system (2) before the cell separator, i.e. into the arterial line (5), or directly into the cell separator (7).

It is obvious for the skilled person that the liquid container(s) (F) themselves do not have to be part of the apheresis device according to the invention, since these are generally single use articles, e. g. in form of common infusion bags, which are connected to the connection line by the operating personnel (e. g. the attending physician or a nurse) in accordance with the specific application.

According to the invention, the presence of a single connection line (11) for connection of a liquid container is possible. However, it is also conceivable that a single connection line (11) is present to which two or three preferably more liquid containers can be connected. Embodiments of the apheresis device according to the invention with two, preferably three or preferably more connection lines (11', 11", 11'", etc.) each for connection of at least one liquid container are also possible, whereby it is then preferred that these two, preferably three or preferably more connection lines independently to each other can run into the arterial line (5) or directly into the cell separator (7). "Independent to each other" means, in this context, for example, that in an embodiment of the apheresis device according to the invention with two connection lines (11', 11"), one connection line (11') can run into the arterial line (5) and the other connection line (11") can run directly into the cell separator (7), but also that both connection lines (11', 11") can run into the arterial line (5) or that that both connection lines (11', 11") can run directly into the cell separator (7).

According to an embodiment of the present invention, it is particularly preferred if the apheresis device (1) according to the invention has two connection lines (11', 11") each for connection of at least one liquid container, wherein the connection lines (11', 11") run independently of each other into the arterial line (5) or directly into the cell separator (7). Consequently, both connection lines (11', 11") run into the arterial line (5) or both connection lines (11', 11") run directly into the cell separator (7) or particularly preferably, one connection line (11') runs into the arterial line (5) and the other connection line (11") runs directly into the cell separator (7). This makes possible that the two connection lines (11', 11") can be connected to different liquid containers. It is particularly preferred if one of the two connection lines (e. g. 11') is connected to a liquid container containing a physiological saline solution (e. g. NaCl solution), while the second of the two connection lines (e. g. 11") is connected to a liquid container containing a citrate solution.

Thus, it is particularly preferred if the apheresis device (1) has a connection line (11') for the connection of a liquid container (F1) and a connection line (11") for the connection of a liquid container (F2) and the connection line (11') runs into the arterial line (5) or into the cell separator (7) and the connection line (11") runs into the arterial line (5) or into the cell separator (7) or into the connection line (11') and thus ultimately also into the arterial line (5) or into the cell separator (7).

The present invention therefore also relates to an apheresis device (1) for extracorporeal removal of CRP from blood comprising:

an extracorporeal circulation system (2) for blood,
means (3) for generation and regulation of a flow of blood in the extracorporeal circulation system (2),
a cell separator (7) for separation of the blood into blood plasma and cellular components, at least one apheresis column (4) for affinity chromatographic removal of CRP from blood, wherein the extracorporeal circulation system (2) comprises an arterial line (5) to the cell separator (7), a plasma line (8A) from the cell separator (7) to the apheresis column (4), a plasma line (8B) for CRP-depleted blood plasma from the apheresis column (4) to a point (P1), a cell line (9) for the separated cellular components from the cell separator (7) to the point (P1) and a venous line (6) starting from the point (P1),
a central processing unit (10) for controlling the apheresis device (1),
two connection lines (11', 11") each for connection of at least one liquid container to the arterial line (5) or the cell separator (7),
characterized in that
a bypass line (12) branches off from the plasma line (8A) and runs into the plasma line (8B),
a waste line (13) goes off directly from the apheresis column (4) or from the plasma line (8B) in the direction of flow before the junction of the bypass line (12), and
at least one regeneration line (14) leads to the plasma line (8A) in the direction of flow at or after the branch of the bypass line (12) or runs directly into the apheresis column (4).

A substantial advantage of the apheresis device of the present invention is that the apheresis column, which is naturally limited in its purification capacity, can be regenerated during operation, i.e. without having to stop the blood sampling and supply or the cell separator. For this purpose, there is a bypass line (12, also referred to as "shunt"), which allows redirection of the plasma flow while bypassing the apheresis column (4). This bypass line (12) enables temporary decoupling of the apheresis column (4) from the plasma flow and thus regeneration of the apheresis column (4) without the need to interrupt the flow of blood or blood plasma in the device according to the invention. The bypass line branches off from the plasma line (8A), wherein the point in the plasma line (8A) from which the bypass line branches off is referred to as point (P2) and preferably runs into the plasma line (8B), wherein the point in the plasma line (8B) into which the bypass line (12) runs is referred to as point (P6). In an also possible embodiment, the bypass line (12) does not run into the plasma line (8B), but into the cell line (9), wherein the point in the cell line (9) into which the bypass line (12) runs is referred to as point (P3).

The regeneration solution necessary for the regeneration of the apheresis column is fed into the extracorporeal circulation system (2) via the regeneration line (14), wherein the regeneration line (14) either runs directly into the apheresis column (4) or runs into the plasma line (8A) (in the direction of flow) before the apheresis column (4) but (in the direction of flow) after the branch of the bypass line, i.e. after the point (P2).

In order to remove the regeneration solution from the system after flowing through the apheresis column (4) (rather than being delivered to the patient), there exists a waste line (13), which branches off from the plasma line (8B), wherein the point in the plasma line (8B) from which the waste line (13) branches off is referred to as point (P4). In embodiments in which the bypass line (12) runs into the cell line (9), the point (P4) is preferably located in a region from the apheresis column (4) to the point (P1). In embodiments in which the bypass line (12) runs into the plasma line (8B), the point (P4) is preferably located in a region from the apheresis column (4) to the point (P6). Of course, a collection container, for example, can be connected to said waste line (13). For example, a physiological sodium chloride solution, TRIS-glycine solution, or a citrate solution can be used as the regeneration solution.

In addition to the regeneration solution, a rinsing solution can also be used. The rinsing solution can, but does not have to, serve to regenerate the apheresis column (4), but has the primary function of removing the blood plasma from the plasma line (8A) in the region from point P2 to the apheresis column (4), from the apheresis column (4) and from the plasma line (8B) from the apheresis column (4) to point P4 before the regeneration solution is used, which is then discarded via the waste line (13) after flowing through the apheresis column (4). The rinsing solution, on the other hand, can be supplied to the patient at least partially as well as completely and does not have to be discarded, at least as long as no regeneration solution is contained in the rinsing solution. Preferably, a physiological NaCl solution is used as the rinsing solution. It is even more preferred to use a physiological NaCl solution as the rinsing solution if a citrate solution is used as the regeneration solution.

The present invention therefore also relates to an apheresis device (1) for extracorporeal removal and preferably for selective extracorporeal removal of CRP from blood comprising:
  an extracorporeal circulation system (2) for blood,
  means (3) for generation and regulation of a flow of blood in the extracorporeal circulation system (2),
  a cell separator (7) for separation of the blood into blood plasma and cellular components, at least one apheresis column (4) for affinity chromatographic removal of CRP from blood, wherein the extracorporeal circulation system (2) comprises an arterial line (5) to the cell separator (7) for separation of the blood into blood plasma and cellular components, a plasma line (8A) from the cell separator (7) to the apheresis column (4) for affinity chromatographic removal of CRP from blood, a plasma line (8B) for CRP-depleted blood plasma from the apheresis column (4) to a point (P1), a cell line (9) for the separated cellular components from the cell separator (7) to the point (P1) and a venous line (6) starting from the point (P1),
  a central processing unit (10) for controlling the apheresis device (1),
  at least one connection line (11) for connection of at least one liquid container to the arterial line (5) or the cell separator (7),
  characterized in that
  a bypass line (12) branches off from the plasma line (8A) and runs into the plasma line (8B),
  a waste line (13) goes off directly from the apheresis column (4) or from the plasma line (8B) in the direction of flow before the junction of the bypass line (12), and
  at least one regeneration line (14) leads into the extracorporeal circulation system (2) in a region from the junction of the bypass line (12) at the plasma line (8A) to the apheresis column (4).

The present invention also relates to an apheresis device (1) for extracorporeal removal and preferably for selective extracorporeal removal of CRP from blood or blood plasma comprising:
  an extracorporeal circulation system (2) for blood or blood plasma, connectable to the blood circulation system of a patient,
  means (3) for generation and regulation of a flow of blood in the extracorporeal circulation system (2),
  a cell separator (7) for separation of the blood into blood plasma and cellular components, at least one apheresis column (4) for affinity chromatographic removal of CRP from blood or blood plasma,
  wherein the extracorporeal circulation system (2) comprises an arterial line (5) from the patient to the cell separator (7),
  a plasma line (8A) starting from the cell separator (7) for the separated blood plasma in fluidic connection with the apheresis column (4) for affinity chromatographic removal of CRP from blood,
  a plasma line (8B) starting from the apheresis column (4) for CRP-depleted plasma blood,
  a cell line (9) starting from the cell separator (7) for the separated cellular components, that runs into the plasma line (8B) at a point (P1),
  and
  a venous line (6) from the point (P1) to the patient;
  a central processing unit (10) for controlling the apheresis device (1),
  at least one connection line (11) for connection of at least one liquid container in fluidic connection with the extracorporeal circulation system,
  characterized in that the apheresis device (1) further comprises:
  a bypass line (12) that leads from a point (P2) in the plasma line (8A) to a point (P3) in the cell line (9) or to a point (P6) in the plasma line (8B),
  a waste line (13) that branches off from a point (P4) in the plasma line (8B),
  at least one regeneration line (14) which runs into the extracorporeal circulation system (2) within a region from point (P2) to the apheresis column (4),
  and point (P4) is arranged before points (P1) and (P6) or point (P4) coincides with point (P6).

The present invention also relates to an apheresis device (1) for extracorporeal removal and preferably for selective extracorporeal removal of CRP from blood or blood plasma comprising:
  an extracorporeal circulation system (2) for blood or blood plasma, connectable to the blood circulation system of a patient,
  means (3) for generation and regulation of a flow of blood in the extracorporeal circulation system (2),
  a cell separator (7) for separation of the blood into blood plasma and cellular components,
  at least one apheresis column (4) for affinity chromatographic removal of CRP from blood or blood plasma,
  wherein the extracorporeal circulation system (2) comprises an arterial line (5) from the patient to the cell separator (7),
  a plasma line (8A) starting from the cell separator (7) for the separated blood plasma in fluidic connection with the apheresis column (4) for affinity chromatographic removal of CRP from blood,
  a plasma line (8B) starting from the apheresis column (4) for CRP-depleted plasma blood,
  a cell line (9) starting from the cell separator (7) for the separated cellular components, that runs into the plasma line (8B) at a point (P1), and
a venous line (6) from the point (P1) to the patient,
a central processing unit (10) for controlling the apheresis device (1),
two connection lines (11', 11") each for connection of at least one liquid container in fluidic connection with the extracorporeal circulation system,
characterized in that the apheresis device (1) further comprises:
a bypass line (12) that leads from a point (P2) in the plasma line (8A) to a point (P3) in the cell line (9) or to a point (P6) in the plasma line (8B),
a waste line (13) that branches off from a point (P4) in the plasma line (8B),
at least one regeneration line (14) which runs into the extracorporeal circulation system (2) within a region from point (P2) to the apheresis column (4),
and point (P4) is arranged before points (P1) and (P6) or point (P4) coincides with point (P6).

According to an embodiment of the present invention it is therefore preferred when the apheresis device (1) according to the invention has at least two connection lines (11) each for connection of at least one liquid container (F) to the arterial line (5) or the cell separator (7).

Furthermore, embodiments of the apheresis device (1) are preferred in which the apheresis device (1) has at least two connection lines (11) each for connection of at least one liquid container (F) to the arterial line (5) or the cell separator (7) and wherein there is a regeneration line (14) per liquid container (F) which goes off from the respective liquid container (F) or its connection line (11) and which each lead into the plasma line (8A) or directly into the apheresis column (4).

It is also possible that the at least two connection lines (11) merge before their junction, i.e. converge into one line. It is also possible that the regeneration lines (14) merge before their junction, i.e. converge into one line.

If it is described in the present application that a device feature lies in a region from a first position in the device to a second position in the device or runs into this region or branches off from this region, this is to be understood in such a way that both the first position and the second position and the section lying in between are enclosed by this region. This is to be illustrated by the following example: The statement that the "regeneration line (14) runs into the extracorporeal circulation system (2) in a region from point (P2) to the apheresis column (4)" means that the regeneration line (14) runs into a region of the extracorporeal circulation system (2) that includes not only the section between point (P2) and the apheresis column (4), but also includes point (P2) itself as well as the apheresis column (4). That means that the regeneration line (14) may run into point (P2), or into the apheresis column (4), or even into the section of the plasma line (8A) that lies between point (P2) and the apheresis column (4).

Point (P1) is the nodal point in the extracorporeal circulation system (2) at which the plasma line (8B) merges with the venous line (6). Point (P2) is the nodal point in the extracorporeal circulation system (2) where the bypass line (12) branches off from the plasma line (8A). The point (P3) is the nodal point in the extracorporeal circulation system (2) where the bypass line (12) runs into the cell line (9). The point (P4) is the nodal point in the extracorporeal circulation system (2) where the waste line (13) branches off from the plasma line (8B). The point (P5) is the nodal point in the extracorporeal circulation system (2) where the regeneration line (15) runs into the connection line (11). The point (P6) is the nodal point in the extracorporeal circulation system (2) at which the bypass line (12) runs into the plasma line (8B).

The present invention is also directed to an apheresis device (1) for extracorporeal removal and preferably for selective extracorporeal removal of CRP from blood or blood plasma comprising:
an extracorporeal circulation system (2) for blood or blood plasma, connectable to the blood circulation system of a patient,
means (3) for generation and regulation of a flow of blood or blood plasma in the extracorporeal circulation system (2),
a cell separator (7) for separation of the blood into blood plasma and cellular components,
at least one apheresis column (4) for affinity chromatographic removal of CRP from blood or blood plasma,
wherein the extracorporeal circulation system (2) comprises an arterial line (5) from the patient to the cell separator (7),
a plasma line (8A) starting from the cell separator (7) for the separated blood plasma in fluidic connection with the apheresis column (4) for affinity chromatographic removal of CRP,
a plasma line (8B) starting from the apheresis column (4) for CRP-depleted blood plasma,
a cell line (9) starting from the cell separator (7) for the separated cellular components, that runs into the plasma line (8B) at a point (P1),
and
a venous line (6) from the point (P1) to the patient,
a central processing unit (10) for controlling the apheresis device (1),
at least one connection line (11) for connection of at least one liquid container to the arterial line (5) or the cell separator (7),
characterized in that the apheresis device (1) further comprises:
a bypass line (12) that leads from a point (P2) in the plasma line (8A) to a point (P3) in the cell line (9) or to a point (P6) in the plasma line (8B),
a waste line (13) that branches off from a point (P4) in the plasma line (8B),
at least one regeneration line (14) which runs into the plasma line (8A) or directly into the apheresis column (4) after point (P2),
and point (P4) is arranged before the points (P1) and (P6) or point (P4) coincides with point (P6).

According to a preferred embodiment of the present invention, the connection line (11) runs into the arterial line (5). According to a further preferred embodiment of the present invention, the connection line (11) runs directly into the cell separator (7).

As already described, the apheresis device according to the invention comprises at least one line (the so-called regeneration line (14)), which enables the feeding of a regeneration solution (e.g. a citrate solution, a TRIS-glycine solution or a NaCl solution) into the extracorporeal circulation system preferably shortly before the apheresis column (4) or directly into the apheresis column (4). In this context, it is also referred to that the regeneration line (14) for connection of at least one liquid container (F) is in fluidic connection with the extracorporeal circulation system, i.e. a liquid from a liquid container can be introduced into the extracorporeal circulation system via the regeneration line.

According to a preferred embodiment of the present invention, the regeneration line (14) runs into the plasma line (8A) after point (P2), i.e. between point (P2) and the apheresis column (4). According to another preferred embodiment of the present invention, the regeneration line (14) runs into the plasma line (8A) at point (P2). According to a further preferred embodiment of the present invention, the regeneration line (14) runs directly into the apheresis column (4).

It is obvious to the skilled person that a liquid container (F) for connection to the regeneration line itself does not have to be part of the apheresis device according to the invention, since these are generally single use articles, e.g. in the form of common infusion bags, which are connected to the connection line by the operating personnel (e.g. the attending physician or a nurse) in accordance with the specific application.

According to the invention, the presence of a single regeneration line (14) for connection of a liquid container (F) is possible. Here, for example, it is conceivable that a separate liquid container, e.g. an infusion bag with NaCl solution, can be connected to the regeneration line (14). However, it is also conceivable that the end of the regeneration line (14) that enables the connection of a liquid container is located in spatial proximity to the end of a connection line (11) that enables the connection of a liquid container, so that a liquid container (with at least two connection options or a corresponding adapter) can be connected to both the connection line (11) and the regeneration line (14).

According to the invention, the presence of a single regeneration line (14) is possible and particularly preferred are 1 or 2 regeneration lines. Also, embodiments of the apheresis device according to the invention with two, three or more regeneration lines (14', 14", 14"', etc.) are possible, in which case these two, three or more regeneration lines can run into the extracorporeal circulation system (2) independently of each another in a region from the branch of the bypass line (12) at the plasma line (8A) (i.e. from point P2) to the apheresis column (4). "Independent of each other" in this context, means, for example, that in an embodiment of the apheresis device according to the invention with two regeneration lines (14', 14"), one regeneration line (14') runs into the plasma line (8A) between point (P2) and the apheresis column (4) and the other regeneration line (14") runs directly into the apheresis column (4), but also that both regeneration lines (14', 14") can runs into the plasma line (8A) between point (P2) and the apheresis column (4). It is also possible that one regeneration line (14') runs into the other regeneration line (14"). However, in the presence of two or more regeneration lines (14', 14", 14"', etc.), it is particularly preferred if all regeneration lines (14', 14", 14"', etc.) run into the extracorporeal circulation system (2) at the same point in the region from point (P2) to the apheresis column (4), even more preferably if all regeneration lines (14', 14", 14"', etc.) run into the extracorporeal circulation system (2) at point (P2).

According to the invention, it is particularly advantageous if a connection line (11) and a regeneration line (14) use the same liquid source, since this not only saves space, but also minimizes the effort required for operation and maintenance of the apheresis device according to the invention. In this way, existing apheresis systems can also be modified or supplemented without the need to connect a separate additional large-scale device. In preferred embodiments of the present invention, therefore, the regeneration line (14) branches off from the connection line (11), wherein the point in the connection line (11) from which the regeneration line (14) branches off being referred to as point (P5).

It is therefore preferred, according to some embodiments of the present invention, that the at least one regeneration line (14) leading into the plasma line (8A) or directly into the apheresis column (4) starts from a point (P5) in the at least one connection line (11).

In embodiments in which more than one connection line (11', 11", 11"' etc.) is present and a regeneration line (14) is connected to several connection lines (11', 11", 11"' etc.), the nomenclature of the branching points (P5', P5", P5"' etc.) is based on the nomenclature of the connection line (11', 11", 11"' etc.). I.e., by way of example, in the case of a regeneration line (14) that runs into or connects to two existing connection lines (11', 11"), the point at which the regeneration line (14) runs into the connection line (11') is referred to as point (P5') and the point at which the regeneration line (14) runs into the connection line (11") is referred to as point (P5").

An apheresis device (1) is preferred, wherein the apheresis device (1) has two connection lines (11', 11") each for connection of one liquid container (F1, F2) to the arterial line (5) or the cell separator (7), and wherein two regeneration lines (14', 14") go off from the two liquid containers (F1, F2) or the two connection lines (11', 11") and lead into the plasma line (8A) or directly into the apheresis column (4).

Embodiments are also conceivable in which a regeneration line (14), which leads into the plasma line (8A) or directly into the apheresis column (4) and which starts from a point (P5) in the at least one connection line (11), has at least one additional connection for a liquid container (see FIG. 7).

In embodiments with more connection lines than regeneration lines, wherein each regeneration line establishes a connection to at least one connection line, it is possible that each regeneration line is connected to one connection line and the excess connection line(s) are connected only to the arterial line or the cell separator, or that the more numerous connection lines converge on the regeneration lines, i.e. several connection lines are connected to one regeneration line. Mixed forms are also possible.

There are various possibilities to regulate the flow rates in the part of the connection line (11) after point (P5) and in the regeneration line (14). This could be done, for example, by separately controllable pumps in the part of the connection line (11) after the point (P5) and in the regeneration line (14). Another possibility would be a pump located in the connection line (11) before point (P5), wherein the distribution of flow rates after point (P5) is either fixed by the diameters of regeneration line (14) and connection line (11) or can be regulated by appropriate means (clamps, valves) (e.g. by varying the respective line diameter). The regulation of flow rates is of course particularly important when a solution (e.g. a citrate solution) has to be fed into the system via the connection line (11) (e.g. for anticoagulation of the blood) and at the same time has to enter the apheresis column via the regeneration line (14) (for regeneration). By means of such mechanisms, for example, the feed of solution via the connection line (11) can be kept constant (e.g. for constant anticoagulation), even if solution is branched off in phases for regeneration of the apheresis column via the regeneration line (14).

Compared to other systems, the apheresis device (1) works with a maximum number of 8, preferably 7, further preferably 6, and most preferably 5 pumps.

Therefore, the present invention is also directed to an apheresis device (1) for extracorporeal removal and preferably for selective extracorporeal removal of CRP from blood or blood plasma comprising:

an extracorporeal circulation system (2) for blood or blood plasma, connectable to the blood circulation system of a patient, means (3) for generation and regulation of a flow of blood or blood plasma in the extracorporeal circulation system (2), a cell separator (7) for separation of the blood into blood plasma and cellular components, at least one apheresis column (4) for affinity chromatographic removal of CRP from blood or blood plasma, wherein the extracorporeal circulation system (2) comprises an arterial line (5) from the patient to the cell separator (7), a plasma line (8A) starting from the cell separator (7) for the separated blood plasma in fluidic connection with the apheresis column (4) for affinity chromatographic removal of CRP, a plasma line (8B) starting from the apheresis column (4) for CRP-depleted blood plasma, a cell line (9) starting from the cell separator (7) for the separated cellular components, that runs into the plasma line (8B) at a point (P1), and a venous line (6) from the point (P1) to the patient, a central processing unit (10) for controlling the apheresis device (1), at least one connection line (11) for connection of at least one liquid container in fluidic connection with the extracorporeal circulation system (2), characterized in that the apheresis device (1) further comprises:

a bypass line (12) that leads from a point (P2) in the plasma line (8A) to a point (P3) in the cell line (9) or to a point (P6) in the plasma line (8B), a waste line (13) that branches off from a point (P4) in the plasma line (8B), at least one regeneration line (14) starting from a point (P5) in the at least one connection line that leads into the extracorporeal circulation system (2) in a region from point (P2) to the apheresis column (4), and point (P4) is arranged before points (P1) and (P6) or in case that the bypass line (12) runs into point (P3), the point (P1) coincides with point (P4) or in case that the bypass line (12) runs into point (P6), the point (P4) coincides with point (P6).

The present invention is also directed to an apheresis device (1) for extracorporeal removal and preferably for selective extracorporeal removal of CRP from blood or blood plasma comprising:

an extracorporeal circulation system (2) for blood or blood plasma, connectable to the blood circulation system of a patient, means (3) for generation and regulation of a flow of blood or blood plasma in the extracorporeal circulation system (2), a cell separator (7) for separation of the blood into blood plasma and cellular components, at least one apheresis column (4) for affinity chromatographic removal of CRP from blood or blood plasma, wherein the extracorporeal circulation system (2) comprises an arterial line (5) from the patient to the cell separator (7), a plasma line (8A) starting from the cell separator (7) for the separated blood plasma in fluidic connection with the apheresis column (4) for affinity chromatographic removal of CRP, a plasma line (8B) starting from the apheresis column (4) for CRP-depleted blood plasma, a cell line (9) starting from the cell separator (7) for the separated cellular components, that runs into the plasma line (8B) at a point (P1), and a venous line (6) from the point (P1) to the patient, a central processing unit (10) for controlling the apheresis device (1), at least one connection line (11) for connection of at least one liquid container to the arterial line (5) or to the cell separator (7), characterized in that the apheresis device (1) further comprises:

a bypass line (12) that leads from a point (P2) in the plasma line (8A) to a point (P3) in the cell line (9) or to a point (P6) in the plasma line (8B), a waste line (13) that branches off from a point (P4) in the plasma line (8B), at least one regeneration line (14) starting from a point (P5) in the at least one connection line and runs into the plasma line (8A) after point (P2) or directly into the apheresis column (4), and point (P4) is arranged before points (P1) and (P6) or in case that the bypass line (12) runs into point (P3), the point (P1) coincides with point (P4) or in case that the bypass line (12) runs into point (P6), the point (P4) coincides with point (P6).

In embodiments of the present invention with several connection lines (11', 11", 11''', etc.) and several regeneration lines (14', 14", 14''', etc.), it is possible that one connection line is in connection with one regeneration line in each case, which in turn runs into the plasma line (8A) or directly into apheresis column (4) after point (P2). Here, each regeneration line can run into the plasma line (8A) or directly into apheresis column (4) at a point after point (P2) independently of other regeneration lines. However, it is preferred if all regeneration lines run into the plasma line (8A) or directly into apheresis column (4) at the same point after point (P2), even more preferably directly into apheresis column (4) and most preferably at point (P2). One such exemplary embodiment may be explained with reference to FIG. 6: Here, the apheresis device (1) has a first connection line (11'), which firstly leads into the arterial line (5) and from which, secondly, a first regeneration line (14') branches off at point (P5'). The apheresis device (1) also has a second connection line (11"), which firstly leads directly into the cell separator (7) and from which secondly a second regeneration line (14") branches off at point (P5"). In this embodiment, both regeneration lines (14', 14") run into the extracorporeal circulation system (2) at point (P2).

An apheresis device (1) is therefore preferred, wherein the apheresis device (1) has two connection lines (11', 11") each for connection of at least one liquid container (F) to the arterial line (5) or the cell separator (7), and wherein the at least one regeneration line (14) leading into the plasma line (8A) or directly into the apheresis column (4) connects at one point (P5') to the connection line (11') and at one point (P5") to the connection line (11").

Thus, embodiments of the apheresis device (1) are particularly preferred, wherein the apheresis device (1) has two connection lines (11', 11") each for connection of at least one liquid container (F1, F2) to the arterial line (5) or the cell separator (7), and wherein the at least one regeneration line (14) leading into the plasma line (8A) or directly into the apheresis column (4), connects at a point (P5') to the connection line (11') and at a point (P5") to the connection line (11"), and wherein a regeneration line (14') leads from the liquid container (F1) or from the connection line (11') that goes off from the liquid container (F1) to the apheresis column (4) or to the plasma line (8A) or to the regeneration line (14'). Preferably, the liquid container (F1) contains a physiological NaCl solution and the liquid container (F2) contains a citrate solution.

Thus, it is particularly preferred if the apheresis device (1) has a connection line (11') for connection of a liquid container (F1) and a connection line (11") for connection of a liquid container (F2), and the connection line (11') runs into the arterial line (5) or into the cell separator (7), and the connection line (11") runs into the arterial line (5) or into the cell separator (7) or into the connection line (11') and therefore ultimately also into the arterial line (5) or into the cell separator (7), and a regeneration line (14') leads from the liquid container (F1) or from the connection line (11') to the apheresis column (4) or to the plasma line (8A), and a regeneration line (14") that leads from the liquid container (F2) or from the connection line (11") to the apheresis column (4) or to the plasma line (8A) or into the regeneration line (14').

Preferably, the liquid container (F1) contains a physiological NaCl solution and the liquid container (F2) contains a citrate solution.

Embodiments of the apheresis device (1) are therefore particularly preferred, in which the apheresis device (1) has a connection line (11') for connection of a liquid container (F1) to the arterial line (5) or the cell separator (7) and a connection line (11") for connection of a liquid container (F2) to the arterial line (5) or the cell separator (7), and wherein a regeneration line (14') goes off from the liquid container (F1) or the connection line (11') and runs in the direction of flow at or preferably after the branch of the bypass line (12) into the plasma line (8A) or directly into the apheresis column (4), and a regeneration line (14") goes off from the liquid container (F2) or the connection line (11") and leads in the direction of flow at or preferably after the branch of the bypass line (12) into the plasma line (8A) or into the regeneration line (14') or directly into the apheresis column (4).

Particularly preferred is therefore an apheresis device (1) for extracorporeal removal and preferably for selective extracorporeal removal of CRP from blood or blood plasma comprising:

an extracorporeal circulation system (2) for blood,
means (3) for generation and regulation of a flow of blood in the extracorporeal circulation system (2),
a cell separator (7) for separation of the blood into blood plasma and cellular components,
at least one apheresis column (4) for affinity chromatographic removal of CRP from blood,
wherein the extracorporeal circulation system (2) comprises an arterial line (5) to the cell separator (7), a plasma line (8A) from the cell separator (7) to the apheresis column (4), a plasma line (8B) for CRP-depleted blood plasma from the apheresis column (4) to a point (P1), a cell line (9) for the separated cellular components from the cell separator (7) to the point (P1), and a venous line (6) starting from the point (P1),
a central processing unit (10) for controlling the apheresis device (1),
a connection line (11') for connection of at least one liquid container (F1) to the arterial line (5) or to the cell separator (7) and a connection line (11") for connection of at least one liquid container (F2) to the arterial line (5) or to the cell separator (7), characterized in that:
a bypass line (12) branches off from the plasma line (8A) and runs the plasma line (8B),
a waste line (13) that goes off directly from the apheresis column (4) or from the plasma line (8B) in the direction of flow bevor the junction of the bypass line (12), and a regeneration line (14') goes off from the liquid container (F1) or the connection line (11') and leads in the direction of flow at or preferably after the branch of the bypass line (12) into the plasma line (8A) or directly into the apheresis column (4), and a regeneration line (14") goes off from the liquid container (F2) or the connection line (11") and leads in the direction of flow at or after preferably after the branch of the bypass line (12) into the plasma line (8A) or into the apheresis column (4) or merges with the regeneration line (14').

Preferably, the liquid container (F1) is a container for a physiological sodium chloride solution and the liquid container (F2) is a container for a citrate solution.

In other words, according to one embodiment, an apheresis device (1) is therefore preferred, wherein the apheresis device (1) has two connection lines (11', 11") each for connection of at least one liquid container to the arterial line (5) or the cell separator (7), and wherein the at least one regeneration line (14) leading into the plasma line (8A) or directly into the apheresis column (4) establishes a connection to the connection line (11') at point (P5') and to the connection line (11") at point (P5"). This is to be understood in such a way that the one regeneration line (14) represents the connecting element between the connection lines (11', 11") on the one side and the plasma line (8A) or the apheresis column (4) on the other side. A liquid from one of the liquid containers (F) connected to one of the two connection lines (11', 11") could therefore flow via the regeneration line (14) into the plasma line (8A) after point (P2) or directly into the apheresis column (4).

The present invention is therefore also directed to an apheresis device (1) for extracorporeal removal of CRP from blood or blood plasma comprising:
an extracorporeal circulation system (2) for blood or blood plasma, connectable to the blood circulation system of a patient,
means (3) for generation and regulation of a flow of blood or blood plasma in the extracorporeal circulation system (2),
a cell separator (7) for separation of the blood into blood plasma and cellular components,
at least one apheresis column (4) for affinity chromatographic removal of CRP from blood or blood plasma,
wherein the extracorporeal circulation system (2) comprises an arterial line (5) from the patient to the cell separator (7),
a plasma line (8A) starting from the cell separator (7) for the separated blood plasma in fluidic connection with the apheresis column (4) for affinity chromatographic removal of CRP,
a plasma line (8B) starting from the apheresis column (4) for CRP-depleted blood plasma,
a cell line (9) starting from the cell separator (7) for the separated cellular components, that runs into the plasma line (8B) at a point (P1), and
a venous line (6) from the point (P1) to the patient,
a central processing unit (10) for controlling the apheresis device (1), two connection lines (11', 11") each for connection of at least one liquid container in fluidic connection with the extracorporeal circulation system (2), characterized in that the apheresis device (1) further comprises:

a bypass line (12) that leads from a point (P2) in the plasma line (8A) to a point (P3) in the cell line (9) or to a point (P6) in the plasma line (8B), a waste line (13) that branches off from a point (P4) in the plasma line (8B), at least one regeneration line (14) which runs into the extracorporeal circulation system (2) within a region from point (P2) to the apheresis column (4), and which establishes a connection to the connection line (11') at point (P5') and to the connection line (11") at point (P5"), and point (P4) is arranged before points (P1) and (P6) or in case that the bypass line (12) runs into point (P3), the point (P1) coincides with point (P4) or in case that the bypass line (12) runs into point (P6), the point (P4) coincides with point (P6).

The present invention is also directed to an apheresis device (1) for extracorporeal removal of CRP from blood or blood plasma comprising:

an extracorporeal circulation system (2) for blood or blood plasma, connectable to the blood circulation system of a patient, means (3) for generation and regulation of a flow of blood or blood plasma in the extracorporeal circulation system (2), a cell separator (7) for separation of the blood into blood plasma and cellular components, at least one apheresis column (4) for affinity chromatographic removal of CRP from blood or blood plasma, wherein the extracorporeal circulation system (2) comprises an arterial line (5) from the patient to the cell separator (7), a plasma line (8A) starting from the cell separator (7) for the separated blood plasma in fluidic connection with the apheresis column (4) for affinity chromatographic removal of CRP, a plasma line (8B) starting from the apheresis column (4) for CRP-depleted blood plasma, a cell line (9) starting from the cell separator (7) for the separated cellular components, that runs into the plasma line (8B) at a point (P1), and a venous line (6) from the point (P1) to the patient, a central processing unit (10) for controlling the apheresis device (1), two connection lines (11', 11") each for connection of at least one liquid container to the arterial line (5) or the cell separator (7), characterized in that the apheresis device (1) further comprises:

a bypass line (12) that leads from a point (P2) in the plasma line (8A) to a point (P3) in the cell line (9) or to a point (P6) in the plasma line (8B), a waste line (13) that branches off from a point (P4) in the plasma line (8B), at least one regeneration line (14) which runs into the plasma line (8A) or directly into the apheresis column (4), and which establishes a connection to the connection line (11') at point (P5') and to the connection line (11") at point (P5"), and point (P4) is arranged before points (P1) and (P6) or in case that the bypass line (12) runs into point (P3), the point (P1) coincides with point (P4) or in case that the bypass line (12) runs into point (P6), the point (P4) coincides with point (P6).

According to one embodiment of the present invention, it is preferred if the apheresis device (1) according to the invention has two connection lines (11', 11"), wherein the first connection line (11') for connection of at least one liquid container (preferably a liquid container for or containing an NaCl solution) is connected (i.e., fluidically connected) to the arterial line (5) and a second connection line (11") for connection of at least one liquid container (preferably a liquid container for or containing a citrate solution) is connected (i.e. fluidically connected) directly to the cell separator (7). Additionally, it is herein preferred if the apheresis device (1) according to the invention has a single regeneration line (14) which, after the point (P2), runs into the plasma line (8A) or directly into apheresis column (4), and which, however, starts from or is connected to both the first connection line (11') and the second connection line (11") (see FIG. 5). That means that the regeneration line (14) is connected to the first connection line (11') at point (P5') and to the second connection line (11") at point (P5") and then leads into the plasma line (8A) or directly into the apheresis column (4) after point (P2). By means of appropriate valves or tube clamps, liquid can thus be led as required via the regeneration line (14) from the liquid container connected to the first connection line (11') into the apheresis column (4) or after point (P2) into the plasma line (8A), or liquid can also be led from the liquid container connected to the second connection line (11").

Such embodiments with two (or even more) connection lines are ideally suitable for using different regeneration solutions for regenerating the apheresis column (4) and successively introducing them into the apheresis column (4). For example, such a device is ideally suitable for first introducing a NaCl solution to displace the plasma contained in the apheresis column, followed by a citrate solution for efficient and rapid regeneration of the adsorber, and finally again by a NaCl solution to displace the citrate solution contained in the apheresis column, before plasma is again introduced into the apheresis column.

Therefore, a particularly preferred embodiment of the present invention relates to an apheresis device (1) for extracorporeal removal and preferably selective extracorporeal removal of CRP from blood or blood plasma comprising:

an extracorporeal circulation system (2) for blood or blood plasma, connectable to the blood circulation system of a patient, means (3) for generation and regulation of a flow of blood or blood plasma in the extracorporeal circulation system (2), a cell separator (7) for separation of the blood into blood plasma and cellular components, at least one apheresis column (4) for affinity chromatographic removal of CRP from blood or blood plasma, wherein the extracorporeal circulation system (2) comprises an arterial line (5) from the patient to the cell separator (7), a plasma line (8A) starting from the cell separator (7) for the separated blood plasma in fluidic connection with the apheresis column (4) for affinity chromatographic removal of CRP, a plasma line (8B) starting from the apheresis column (4) for CRP-depleted blood plasma, a cell line (9) starting from the cell separator (7) for the separated cellular components, that runs into the plasma line (8B) at a point (P1), and a venous line (6) from the point (P1) to the patient, a central processing unit (10) for controlling the apheresis device (1), a first connection line (11') for connection of at least one liquid container to the arterial line (5) and a second connection line (11") for connection of at least one liquid container directly to the cell separator (7)

characterized in that the apheresis device (1) further comprises:

a bypass line (12) that leads from point (P2) in the plasma line (8A) to a point (P3) in the cell line (9) or to a point (P6) in the plasma line (8B), a waste line (13) that branches off from a point (P4) in the plasma line (8B), at least one regeneration line (14) which runs into the plasma line (8A) or directly into the apheresis column (4) after the point (P2), and which establishes a connection at point (P5') to the connection line (11') and at point (P5") to the connection line (11"), and point (P4) is arranged before points (P1) and (P6).

In embodiments of the apheresis device according to the invention, in which the bypass line (12) leads to the point (P6) in the plasma line (8B), it is preferred if the point (P6) is located before (in the flow direction) the point (P1) (see FIGS. 1-3).

According to a preferred embodiment of the present invention, the connection line runs into the arterial line. According to another preferred embodiment of the present invention, the connecting line runs directly into the cell separator.

According to a preferred embodiment of the present invention, the regeneration line (14) runs into the plasma line (8A) after point (P2), i.e. between point (P2) and the apheresis column (4). According to a further preferred embodiment of the present invention, the regeneration line (14) runs directly into the apheresis column (4).

To reduce the dead volume of the system, it is particularly preferred according to the invention if, in the apheresis device (1) according to the invention, the at least one regeneration line (14) runs into the extracorporeal circulation system (2) at point (P2). In embodiments in which more than one regeneration line (14', 14", 14'", etc.) is present, it is particularly preferred if all of the present regeneration lines (14', 14", 14'", etc.) run into the extracorporeal circulation system (2) at point (P2), or run into the plasma line (8A) at point (P2).

The present invention is therefore also directed to an apheresis device (1) according to the invention, wherein the bypass line (12) leads from a point (P2) in the plasma line (8A) to a point (P6) in the plasma line (8B), and the waste line (13) leads from a point (P4) from the plasma line (8B), and the at least one regeneration line (14) runs into the plasma line (8A) at the point (P2).

To further reduce the dead volume of the system, it is even more preferred if not only the regeneration line (14) runs into the plasma line (8A) at the point (P2) where the bypass line (12) also branches off from the plasma line (8A), but also if the waste line (13) branches off from the same point in the plasma line (8B) into which the bypass line (12) also runs. In other words, it is preferred if the point (P6) at which the bypass line (12) runs into the plasma line (8B) and the point (P4) at which the waste line (13) branches off from the plasma line (8B) coincide, i.e. if P4=P6 (see also FIG. 2 and FIG. 3).

The present invention is therefore also directed to an apheresis device (1) according to the invention, wherein the bypass line (12) leads from a point (P2) in the plasma line (8A) to a point (P6) in the plasma line (8B), and the waste line (13) leads from a point (P4) in the plasma line (8B), and the at least one regeneration line (14) runs into the plasma line (8A) at the point (P2), and wherein the point (P6) and the point (P4) are identical.

In the device according to the invention, a cell separator is installed which divides the blood of the patient supplied to it (via the arterial line) into the blood plasma and the cellular components, and conveys these fractions away via the corresponding lines, i.e. the plasma line and the cell line respectively. Here, as already mentioned, it must be taken into account that the separation into blood plasma and cellular components by the cell separators used is not made completely, but only preferably 10 to 90% of the total blood plasma is separated from the cellular components. When centrifugal cell separators are used, preferably 70% to 90%, further preferably 80% to 87% of the total blood plasma is separated from the cellular components. When membrane cell separators are used, preferably 10% to 30%, more preferably 13% to 25%, still more preferably 15% to 20% of the total blood plasma is separated from the cellular components.

Possible types of cell separators that may be used in connection with the present invention comprise centrifugal cell separators, membrane cell separators such as, for example, membrane cell separators with semi-permeable membranes, and membrane cell separators with rotating membranes.

The present invention is therefore also directed to an apheresis device for extracorporeal removal of CRP from blood, wherein the cell separator (7) is either a centrifugal cell separator or a membrane cell separator.

Where in the present application the position of one or more components of the apheresis device according to the invention in relation to another component of the apheresis device according to the invention is described by the terms "before" or "after" (or "before in the direction of flow" and "after in the direction of flow"), this refers to the general direction of flow of the blood or blood plasma in the apheresis device according to the invention. "Before" in relation to a component of the device according to the invention consequently means against the general flow direction of the blood or blood plasma, and "after" in relation to a component of the device according to the invention consequently means with the general flow direction of the blood or blood plasma. It is preferred that the direction of flow in the apheresis device does not reverse or is not reversed by the means for generation and regulation of a flow.

According to the present invention, the apheresis device for extracorporeal removal of CRP from blood according to the invention comprises an apheresis column (4) for affinity chromatographic removal of CRP from blood or blood plasma, the function of which is to bind CRP which is present in the blood or blood plasma of a patient and which is passed through the apheresis column (4).

The term "affinity chromatographic" with regard to the removal of CRP, as used in the present application, means that the removal of CRP occurs by a specific binding between CRP and components of the apheresis column (4) for the removal of CRP. In this context, one may also speak of a "selective removal of CRP" or of a "selective CRP apheresis". Such specific binding between CRP and components of the apheresis column (4) are based on the structural properties of the CRP protein and include, for example, the characteristic binding of CRP to phosphocholine as well as its derivatives or the binding of CRP to antibodies directed against an epitope of CRP. Selective or molecule-specific removal of CRP involves CRP binding with higher affinity to the matrix in the apheresis column (4) than to other structures/molecules. Also, CRP binds with higher affinity to the matrix in the apheresis column (4) than other substances present in the blood, i.e., the matrix has specificity for CRP, or the matrix is specific for CRP. The matrix, preferably a solid phase modified with phosphocholine, preferably binds CRP selectively, i.e., almost exclusively CRP is bound and no other blood components such as LDL cholesterol, antibodies, or uremic toxins. Thus, "removal of CRP" as disclosed herein preferably means selective removal of CRP.

In principle, the design or construction of such an apheresis column (or cartridge or cassette) is part of the state of the art and can be taken from EP 0237659 B1, for example. The exact dimensions of the cartridge, column or cassette used in accordance with the invention (as a device for the selective removal of CRP) depends here to a large extent on the intended use of the device according to the invention. Apheresis column (4) for the affinity chromatographic removal of CRP generally comprises a housing, e.g. in the form of a cartridge or a cassette, which is in fluidic connection with the extracorporeal circulation system via at least one inlet and at least one outlet and which contains a matrix for the affinity chromatographic or adsorptive removal of CRP.

The matrix for affinity chromatographic (or adsorptive) removal of CRP comprises a matrix substrate material to which, in turn, compounds are bound that have the property of specifically binding CRP. According to a preferred embodiment of the present invention, the matrix is integrated into or immobilized in the apheresis column (4) for affinity chromatographic removal of CRP in such a way that it cannot be flushed out of the column with the blood plasma flow. Depending on the embodiment, this can be realized, for example, in the form of filters at the inlet and outlet of the device.

In principle, all inert chromatography or column materials are suitable as matrix substrate materials for preparation of the matrix, which, in particular, do not react with blood or blood plasma or alter or contaminate blood or blood plasma in such a way that the blood or blood plasma can no longer be returned to a patient after contact with the matrix. Suitable matrix substrate materials according to the invention therefore comprise, but are not limited to, Eupergite, polyvinylpyrrolidone, methacrylate, methacrylate resins, agarose, Sepharose, acrylic beads, cellulose matrices, ceramic matrices, glass beads, and/or solid-phase silica or mixtures and/or derivatives thereof. The solid-phase silica matrix can comprise virtually any form of particulate silica, including amorphous silicas such as colloidal silica, silica gels, precipitated silicas, and fumed or pyrogenic silicas; microcrystalline silicas such as diatomaceous earth; and crystalline silicas such as quartz. According to the invention, the compounds bound to the matrix substrate materials that have the property of specifically binding CRP are selected from the group comprising or consisting of lipids, lysophospholipids, lysophosphatidylcholine, peptides, peptides containing charged amino acids, peptides containing the sequence ArgProArg, polypeptides, antibodies, monoclonal antibodies, antibody fragments, engineered antibodies, phosphocholine, derivatives of phosphocholine, DNA, DNA derivatives, RNA, RNA derivatives, L-ribonucleic acid aptamers, such as Spiegelmere® (an RNA-like molecule consisting of L-ribose units) and aptamers.

$Ca^{2+}$-Dependent Ligands for CRP

As already mentioned several times, a column material containing phosphocholine and/or its derivatives is used for affinity chromatographic removal of CRP from biological fluids, e.g. from blood or blood plasma, allowing $Ca^{2+}$-dependent binding of CRP to said functionalized column material.

For this, phosphocholine and/or its derivatives are immobilized on a column material. This is usually done via an organic linker group through which the phosphocholine or its derivatives are adsorptively or even more preferably covalently linked to the column material. This results in a so-called "functionalized column material", wherein the chemical group responsible for the $Ca^{2+}$-dependent binding of CRP is exposed to the outside, so that CRP, which is in a biological fluid, also has access to said chemical group.

In other words, the term "functionalized column material" as used herein refers to a column material for affinity chromatography that has been provided with a functional chemical group. Here, the functional chemical group may be linked to the column material via adsorptive or ionic interactions but preferably via a covalent bond. Of course, it is of importance that the functional chemical group is connected to the column material in such a way that the functional group is active and exposed so that its functionality is maintained. Hereby it is possible that the group attached to the column material (here: ω-phosphonooxyalkyl ammonium group and/or ω-ammoniumalkoxy-hydroxy-phosphoryloxy group) attached to the column material can interact with or bind a ligand (here: CRP) from the sample (here: biological fluid such as blood or blood plasma).

Depending on whether the phosphocholine or its derivative is linked to the column material via the ammonium group or via the phosphate group through an organic linker, a distinction is made between a column material functionalized with a ω-phosphonooxyalkyl ammonium group (linkage via the ammonium group) and a column material functionalized with an ω-ammoniumalkoxy-hydroxy-phosphoryloxy group (linkage via the phosphate group).

The linkage to the column material (via an organic linker, if appropriate) is shown in the formulas (I) and (II) below via a dashed line at either the nitrogen atom of the ammonium group or the oxygen atom of the phosphate group.

The term "ω-phosphonooxyalkyl ammonium group" as used herein may be used synonymously with "omega-phosphonooxyalkyl ammonium" and describes compounds of the following general formula (I).

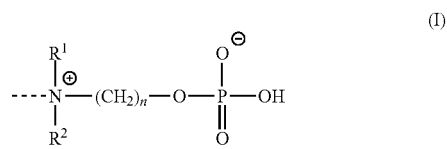

(I)

wherein n is selected from 2 and 3;

$R^1$ and $R^2$ are independently of each other selected from:
—H, —CH$_3$, —C$_2$H$_5$, —C$_3$H$_7$, —C$_4$H$_9$, —C$_5$H$_{11}$, —$C_6H_{13}$, or $R^1$ and $R^2$ together with the nitrogen atom to which they are attached can form a heterocycle selected from:

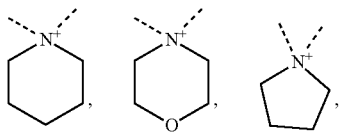

wherein one or more hydrogen atom(s) can be replaced by (a) fluor atom(s).

Preferred ω-phosphonooxyalkyl ammonium groups comprise compounds of the general formula (I)

$$\text{----}\overset{R^1}{\underset{R^2}{\overset{|\oplus}{N}}}\text{---}(CH_2)_n\text{---}O\text{---}\overset{O^\ominus}{\underset{O}{\overset{||}{P}}}\text{---}OH \qquad (I)$$

wherein
n is 2 or 3;
$R^1$ and $R^2$ are independently of each other selected from: —H, —$CH_3$, —$C_2H_5$, —$C_3H_7$ or $R^1$ and $R^2$ together with the nitrogen to which they are bound can form a heterocycle, which is selected from:

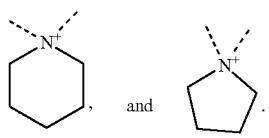

Particularly preferred ω-phosphonooxyalkyl ammonium groups comprise compounds of the general formula (I)

$$\text{----}\overset{R^1}{\underset{R^2}{\overset{|\oplus}{N}}}\text{---}(CH_2)_n\text{---}O\text{---}\overset{O^\ominus}{\underset{O}{\overset{||}{P}}}\text{---}OH \qquad (I)$$

wherein
n is 2;
$R^1$ and $R^2$ are selected from: —H, —$CH_3$, —$C_2H_5$, and particularly preferred from —$CH_3$ and —$C_2H_5$ or $R^1$ and $R^2$ together with the nitrogen atom to which they are attached can form a heterocycle selected from:

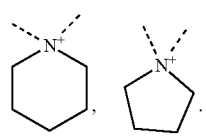

Preferred compounds containing a ω-phosphonooxyalkyl ammonium group as described above and suitable for functionalization of a corresponding column material comprise, for example:

2-[2-(2-aminoethoxy)ethyl-diethyl-ammonio]ethyl hydrogen phosphate, 2-[4-[2-(2-aminoethoxy)ethyl]morpholin-4-ium-4-yl]ethyl hydrogen phosphate, 2-[1-[2-(2-aminoethoxy)ethyl]piperidin-1-ium-1-yl]ethyl hydrogen phosphate, 2-[2-(2-aminoethoxy)ethyl-dimethyl-ammonio]ethyl hydrogen phosphate, 2-[3-aminopropyl-(dimethyl) ammonio]ethyl hydrogen phosphate, 2-[dimethyl (4-sulfanylbutyl) ammonio]ethyl hydrogen phosphate, 2-[4-azidobutyl (dimethyl) ammonio]ethyl hydrogen phosphate, 2-[dimethyl (pent-4-ynyl) ammonio]ethyl hydrogen phosphate, 2-[3-(6-aminohexanoyl-amino) propyl-diethyl-ammonio]ethyl hydrogen phosphate, 2-[1-[2-[2-(6-aminohexanoyl-amino)ethoxy]ethyl]piperidin-1-ium-1-yl]ethyl hydrogen phosphate, 2-[4-[2-[3-(6-aminohexanoylamino) propanoylamino]ethoxy]ethyl] morpholin-4-ium-4-yl]ethyl hydrogen phosphate, 2-[1-[2-[2-[6-(6-aminohexanoylamino) hexanoylamino] ethoxy]ethyl]pyrrolidin-1-ium-1-yl]ethyl hydrogen phosphate, 2-[2-allyloxyethyl (dimethyl) ammonio]ethyl hydrogen phosphate, 2-[2-allyloxyethyl (diethyl) ammonio]ethyl hydrogen phosphate, 2-[4-(2-allyloxyethyl) morpholin-4-ium-4-yl]ethyl hydrogen phosphate, 2-[1-(2-allyloxyethyl) piperidin-1-ium-1-yl]ethyl hydrogen phosphate, 2-[2-[2-(6-aminohexanoylamino)ethoxy]ethyl dimethyl-ammonio]ethyl hydrogen phosphate, 2-[2-[3-(6-aminohexanoylamino) propanoylamino]ethoxy]-ethyl-dimethyl-ammonio]ethyl hydrogen phosphate, 2-[3-azidopropyl (dimethyl) ammonio]ethyl hydrogen phosphate, 2-[dimethyl-[2-[2-(prop-2-ynoxycarbonylamino)ethoxy] ethyl]ammonio]ethyl hydrogen phosphate, 2-[2-[2-(allyloxycarbonylamino)ethoxy]ethyl dimethyl-ammonio] ethyl hydrogen phosphate, 2-[2-[2-[6-(allyloxycarbonylamino) hexanoylamino]ethoxy]ethyl dimethyl-ammonio]ethyl hydrogen phosphate, 2-[2-(6-aminohexanoylamino)ethyl-dimethyl-ammonio]ethyl hydrogen phosphate, 2-[dimethyl-[3-[6-(prop-2-ynoxycarbonylamino) hexanoylamino]propyl]ammonio]ethyl hydrogen phosphate, and 2-[3-(6-aminohexanoylamino) propyl-dimethyl-ammonio]ethyl hydrogen phosphate.

The term "ω-ammoniumalkoxy-hydroxy-phosphoryloxy groups" as used herein can be used similarly as "omega-ammoniumalkoxy-hydroxy-phosphoryloxy groups" and describes compounds of the following general formula (II)

$$\text{----}O\text{---}\overset{O^\ominus}{\underset{O}{\overset{||}{P}}}\text{---}O\text{---}(CH_2)_n\text{---}\overset{R^1}{\underset{R^2}{\overset{|\oplus}{N}}}\text{---}R^3 \qquad (II)$$

wherein
n is selected from 2 and 3;
$R^1$, $R^2$ and $R^3$ are independently of each other selected from: —H, —$CH_3$, —$C_2H_5$, —$C_3H_7$, —$C_4H_9$, —$C_5H_{11}$, —$C_6H_{13}$,
or $R^1$ and $R^2$ together with the nitrogen atom to which they are attached can form a heterocycle selected from:

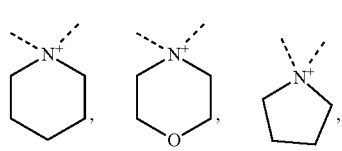

and

R³ is selected from: —H, —CH₃, —C₂H₅, —C₃H₇, —C₄H₉, —C₅H₁₁, —C₆H₁₃, and preferably —H;

wherein one or more hydrogen atom(s) can be replaced by (a) fluor atom(s).

Preferred "ω-ammoniumalkoxy-hydroxy-phosphoryloxy groups" comprise compounds of the general formula (II)

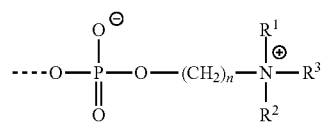

(II)

wherein n is selected from 2 and 3;

R¹, R² and R³ are independently of each other selected from: —H, —CH₃, —C₂H₅, —C₃H₇, or R¹ and R² together with the nitrogen atom to which they are attached can form a heterocycle selected from:

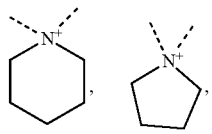

and R³ is —H.

Within the scope of the present invention, it is particularly preferred if the w-ammoniumalkoxy-hydroxy-phosphoryloxy group is an ω-trialkylammoniumalkoxy-hydroxy-phosphoryloxy group.

Therefore, particularly preferred ω-ammoniumalkoxy-hydroxy-phosphoryloxy groups comprise compounds of the general formula (II)

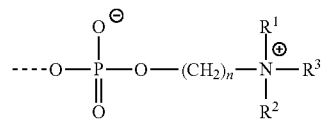

(II)

wherein n is 2;

and R¹, R² and R³ are selected from: —H, —CH₃, —C₂H₅ and particularly preferred from —CH₃ and —C₂H₅.

It is also particularly preferred if the ω-ammoniumalkoxy-hydroxy-phosphoryloxy groups are ω-trimethylammoniumethoxy-hydroxy-phosphoryloxy groups or W-trimethylammoniumpropoxy-hydroxy-phosphoryloxy groups.

Preferred compounds containing an ω-ammoniumalkoxy-hydroxy-phosphoryloxy group as described above and suitable for the functionalization of a corresponding column material comprise for example: p-aminophenylphosphocholine (APPC), 4-[hydroxy [2-(trimethylammonio)ethoxy]phosphinyl]oxy]benzenediazonium (p-diazonium phenylphosphocholine) or p-nitrophenyl-6-(O-phosphocholine) hydroxyhexanoate.

In one possible embodiment of the present invention, the ω-ammoniumalkoxy-hydroxy-phosphoryloxy group is linked via a phosphoester bond to a hydroxy group of a glycerol molecule (as an organic linker), wherein the resulting glycerol ester is then linked to the column material via a second hydroxy group of the glycerol. In such an embodiment, it is also possible that the remaining third hydroxy group of the glycerol is either esterified with a fatty acid or esterified with a second ω-ammoniumalkoxy-hydroxy-phosphoryloxy group. Moreover, the position of the respective esterification on the glycerol molecule can vary. Suitable fatty acids are common saturated, monoolefinic, polyolefinic, monoacetylenic, unsaturated linear and/or branched fatty acids having 8 to 28 carbon atoms. Preferred fatty acid residues are palmitic acid, arachidonic acid, oxovaleric acid, glutaric acid, epoxyisoprostane and stearic acid.

Column Material

For the preparation of the column material functionalized with ω-phosphonooxyalkyl ammonium groups and/or with ω-ammoniumalkoxy-hydroxy-phosphoryloxy groups, in principle, all inert chromatography or column materials are suitable as materials which, in particular, do not react with blood or blood plasma, or alter or contaminate the blood or blood plasma such that the blood or blood plasma after contact with the column material can no longer be injected into a patient. The column materials suitable according to the invention therefore comprise, but are not limited to: Eupergite®, polyvinylpyrrolidone (PVP), polysulfone (PS), polyethersulfone (PES), polyarylethersulfone (PAES), polyacrylate, methacrylate, methacrylate resins such as poly(methyl methacrylate) (PMMA) and poly(glycidyl methacrylate) (PGMA), poly(hydroxy methacrylate), polystyrene (PS), polytetrafluoroethylene (PTFE), polyacrylamide, polyacrolein, acrylonitrile butadiene styrene (ABS), polyacrylonitrile (PAN), polyurethane (PU), Sepharose®, acrylic beads, agarose, cellulose matrices, polyethylene glycol (PEG), alginate, carrageenan, chitin, starch, nitrocellulose, ceramic matrices, glass beads and/or solid phase silicas or mixtures and/or derivatives of these substances. The solid-phase silica matrix can comprise almost any form of particulate silica, including amorphous silica, such as colloidal silica, silica gel, precipitated silica, and fumed or pyrogenic silica; microcrystalline silicas such as diatomaceous earth; and crystalline silicas such as quartz. The silica has a particle size in the range of about 45 to 120 mesh (approximately 345 μm to 125 μm), preferably in the range of about 45 to 60 mesh (approximately 345 μm to 212 μm).

Often, for the functionalization with ω-phosphonooxyalkyl ammonium groups and/or with ω-ammoniumalkoxy-hydroxy-phosphoryloxy groups, a column material is used which has already been "pre-functionalized", i.e. has been provided with a chemical group which then in turn allows the covalent attachment of the ω-phosphonooxyalkyl ammonium groups and/or the ω-ammoniumalkoxy-hydroxy-phosphoryloxy groups.

Such a "pre-functionalization" of a column material is achieved by methods well known to a skilled person in the art (*Chin J Chem* 2012, 30, 2473; Polym Int 2013, 62, 991). In addition, some already "pre-functionalized" column materials are commercially available such as Toyopearl® AF-epoxy, Toyopearl® AF-amino, Toyopearl® AF-tresyl, TSKgel® tresyl, epoxy-activated Sepharose® 6B (GE Healthcare Life Sciences), CNBr-activated Sepharose® 4 fast flow (GE Healthcare Life Sciences), ECH Sepharose® 4B (GE Healthcare Life Sciences), NHS-activated Sepharose® 4 fast flow (GE Healthcare Life Sciences), terminal vinylsulfone activated Sepharose® 4 fast flow (Affiland), aldehyde Separopore® (Agarose) 4B, ECH Separopore® (Agarose) 4B (Separopore), agaroses from Sterogene Bio-separations, Inc., e.g. Epoxy-Ultraflow-4 Agarose (Sterogene Bioseparations, Inc.), Epoxy-Ultraflow-6 Agarose (Sterogene Bioseparations, Inc.), agaroses from emp Biotech GmbH, Epoxy-Ultraflow-4 Agarose (emp Biotech GmbH), Epoxy-Ultraflow-6 Agarose (emp Biotech GmbH), activated agaroses with any degree of cross-linking. In principle, columns for the selective removal of cholesterol (LDL cholesterol) and anti-factor VII or IX antibodies are not suitable and cannot be used for the affinity chromatographic removal of CRP and, in particular, for the selective affinity chromatographic removal of CRP from blood.

Columns consisting of protein A bound to a matrix substrate material are suitable for affinity chromatographic purification of antibodies, i.e. the column is specific for antibodies but not for CRP.

A well-known example of a matrix for the affinity chromatographic removal of LDL cholesterol are polyacrylamide beads with polyacrylic acid covalently bound to their surface (also known under the trade names Dali beads, where DALI stands for "direct adsorption of lipids"). Only the small proteins (lipoproteins such as LDL with a diameter of 25 nm) diffuse through the pores (diameter 100-200 nm) into the interior of the sponge-like structure of the beads as a result of their size.

Pumps

According to the present invention, in the apheresis device for extracorporeal removal of CRP from blood according to the invention, means are provided for generation and regulation of a flow of the blood (or blood plasma) in the extracorporeal circulation system. For this, one or more pumps or pump systems are generally used, which enable a controllable flow of the blood (or blood plasma or also the regeneration solution or anticoagulation solution) through the extracorporeal circulation system and the components of the device according to the invention which are fluidically connected thereto.

According to the invention, the preferred direction of flow within the extracorporeal circulation system and the components of the device according to the invention that are fluidically connected to it passes from the access on the patient through which the blood enters the device according to the invention, via the arterial line of the extracorporeal circulation system to the venous line of the extracorporeal circulation system and to the access on the patient at which the treated blood is returned to the patient.

The means used according to the invention for generation and regulation of a flow in the extracorporeal circulation system are preferably pumps in the form of peristaltic pumps (also referred to as hose pumps), piston pumps, pneumatic pumps, hydraulic pumps or other types of pumps known to the skilled person. Consequently, the term "means for generation and regulation of a flow" and the term "pump" may be used synonymously herein.

According to the invention, it is preferred if the means used for generation and regulation of a flow of blood (or blood plasma or also the regeneration solution or anticoagulation solution) in the extracorporeal circulation system have no direct physical contact with the blood (or blood plasma or also the regeneration solution or anticoagulation solution) in the device according to the invention. This is particularly advantageous for hygienic reasons and prevents contamination of complex mechanical components such as a pump by blood as well as, of course, of the blood by the means for flow generation used.

In a particularly preferred embodiment of the present invention, the means for generation and regulation of a flow in the extracorporeal circulation system is therefore one or more peristaltic pump(s).

The exact location of the means for generation and regulation of a flow in the extracorporeal circulation system, i.e., the one or more pump(s), is not essential to the present invention. Embodiments of the present invention using only one pump are possible, in which the pump is located in the arterial line region of the apheresis device according to the invention for extracorporeal removal of CRP from blood, i.e., before the cell separator. According to the invention, if several means for generation and regulation of a flow in the extracorporeal circulation system are provided, i.e. several pumps, it is preferred if these can be controlled and regulated independently of each other (e.g. by the CPU). Depending on the specific application, different flow rates within the extracorporeal circulation system may be desired or required. It is also conceivable that different flow rates are desired in different components of the device according to the invention during a specific application.

According to the invention, several means for generation and regulation of a flow (i.e. pumps) can also be integrated in the apheresis device according to the invention. Thus, it is possible that means for generation and regulation of a flow are located in the arterial line (5) and/or in the plasma line (8A) and/or in the plasma line (8B) and/or in the venous line (6) and/or in the bypass line (12) and/or in the cell line (9) and/or in the connection line (11) and/or in the connection lines (11', 11", 11''', etc.) and/or in the regeneration line (14) or the regeneration lines (14', 14", 14''', etc.). As indicated above, according to an embodiment of the present invention in which the regeneration line (14) branches off from the connection line (11) at point (P5), it is preferred that a means for generation and regulation a flow (of inorganic salt solutions) is provided in the connection line (11) before point (P5).

According to a further embodiment of the present invention, in which the regeneration line (14) branches off from the connection line (11) at point (P5), it is preferred that a means for generation and regulation of a flow is provided in the connection line (11) after point (P5) and a means for generation and regulation of a flow is provided in the regeneration line (14).

Furthermore, the apheresis device (1) preferably has at least one particle filter which is provided behind of the apheresis column (4) in the plasma line (8B) or the venous line (6).

Furthermore, the apheresis device (1) preferably has at least one bubble catcher provided behind of the apheresis column (4) in the plasma line (8B) or the venous line (6).

In the case of a centrifuge as cell separator (7), the apheresis device (1) preferably has at least one plasma reservoir provided after the centrifuge (7) and before the apheresis column (4) in the plasma line (8A).

In further embodiments, the apheresis device according to the invention for extracorporeal removal of CRP from blood or blood plasma may comprise one or more pressure sensors that serve to measure or monitor the pressure in a specific section of the device according to the invention. This not only serves to monitor and adjust the operating parameters of the apheresis device according to the invention but is also advantageous in that in the event of a malfunction (e.g., a blockage of a tube or filter of the device), operation can be stopped to avoid harmful consequences for the patient. The exact mode of operation and installation position in the device according to the invention is part of the prior art and is known to the person skilled in the art. In a preferred embodiment of the present invention, at least one pressure sensor is arranged in the arterial line of the apheresis device according to the invention as wells as at least one pressure sensor is arranged in the venous line of the apheresis device according to the invention. In a further preferred embodiment of the present invention, such pressure sensors are integrated in the means used for generation and regulation of a flow in the extracorporeal circulation system of the apheresis device according to the invention.

In order to be able to control the direction of flow in the system at the nodal points of the extracorporeal circulation system, i.e. at the points where several lines converge or diverge from each other, means are preferably provided which determine the flow of the solution (e.g. blood, plasma or regeneration solution). These may be valves, multi-way valves, clamps, or valves in the form of stop valves, check valves, pressure valves, directional valves, or other types of valves known to those skilled in the art, which release the flow in a certain direction and block it in another direction. Preferably, such means for flow regulation (e.g. valves) are located at point (P1) and/or at point (P2) and/or at point (P3) and/or at point (P4) and/or at point (P5) and/or at point (P6). In addition, it is possible that e.g. at one point two or more valves are connected in series to enable a more complex flow regulation.

It is also particularly preferred if the means for flow regulation (e.g. valves) can be controlled electronically, i.e. their position can be effected by the central processing unit (10).

The present invention is therefore also directed to an apheresis device for extracorporeal removal of CRP from blood, wherein electronically controlled valves are provided at points (P1), (P2), (P4), (P5), (P6), (P7), and (P8).

It is also conceivable and in accordance with the invention if valves are not located directly at the branching points (P1, P2, P4, P5, P6, P7 and P8), but are located in the upstream and/or downstream lines, and thus control the flow of solutions in the extracorporeal circulation system. Hose clamps can also be used for this purpose. It is particularly preferred if these valves or hose clamps are electronically controlled.

Another advantage of the present invention, which is related to the fact that the apheresis and the regeneration of the apheresis column are implemented in a single device, is that the entire device can be controlled via a single central processing unit (CPU) only. Thus, the different programs during an apheresis session, for example, normal operation, in which the blood plasma is passed through the apheresis column, and regeneration operation, in which the blood plasma is bypassing the apheresis column through the bypass line and the apheresis column is rinsed with regeneration solution, can be controlled by a single processing unit or software located on it. This facilitates the automation of many processes and thus reduces the scope for operator error by the personnel. In prior art devices, on the other hand, different complex systems (primary system for blood separation into plasma and cellular components; and secondary system for apheresis and regeneration) must be combined, with each system controlled separately.

The present invention is therefore also directed to an apheresis device for extracorporeal removal of CRP from blood, wherein the entire device is controlled only by means of the one central processing unit (10).

A further aspect of the present invention relates to an apheresis device, wherein a second apheresis column (4") is connected to the bypass line or the bypass line comprises a second apheresis column. Preferably, the second apheresis column (4") is contained in the bypass line. Thus, the apheresis devices of the invention described herein for extracorporeal removal of CRP from blood may contain a second apheresis column (4"), wherein the second apheresis column (4") is contained in the bypass line. An apheresis column (4") is contained in the bypass line when a section of the bypass line (12') of the bypass line (12) runs into the second apheresis column (4") and another section of the bypass line (12") of the bypass line (12) leads away from the outlet of the apheresis column (4").

Therefore, a further aspect of the present invention is apheresis device (II) for extracorporeal removal and preferably for selective extracorporeal removal of CRP from blood comprising:
  an extracorporeal circulation system (2) for blood,
  a means (3) for generation and regulation of a flow of blood in the extracorporeal circulation system (2),
  a cell separator (7) for separation of the blood into blood plasma and cellular components, two apheresis columns (4', 4") for affinity chromatographic removal of CRP from blood plasma,
  wherein the extracorporeal circulation system (2) comprises an arterial line (5) to the cell separator (7), a plasma line (8A) from the cell separator (7) to the apheresis column (4'), a plasma line (8B) for CRP-depleted blood plasma from the apheresis column (4') to a point (P1), a cell line (9) for the separated cellular components from the cell separator (7) to the point (P1) and a venous line (6) starting from the point (P1),
  a central processing unit (10) for controlling the apheresis device (1),
  a connection line (11) for connection of at least one liquid container (F) to the arterial line (5) or the cell separator (7),
characterized in that
  a bypass line (12) branches off from the plasma line (8A) and runs into the plasma line (8B), and the bypass line (12) comprises the second apheresis column (4"),
  a waste line (13) goes off directly from the apheresis column (4') or from the plasma line (8B) in the direction of flow before the junction of the bypass line (12), and
  at least one regeneration line (14) which goes off from the at least one liquid container (F) or from the at least one connection line (11) and leads to the plasma line (8A) in the direction of flow at or after the branch of the bypass line (12) or runs directly into the apheresis column (4'), and
  wherein a second apheresis column (4") is connected in parallel to the first apheresis column (4') and both apheresis columns (4', 4") can only be operated alternately, i.e. cannot be used simultaneously for CRP removal.

The above-mentioned embodiments of the apheresis device (1) according to the invention are to be transferred to the apheresis device (II) according to the invention.

With the aid of this apheresis device (II) according to the invention, it is possible to remove CRP from blood more efficiently than with prior art devices for the same treatment time. By using two apheresis columns connected in parallel, which can only be used alternately for CRP removal, one apheresis column can be used by means of the apheresis device according to the invention for the removal of CRP from the blood, while the second apheresis column can either be replaced by another apheresis column or the second apheresis column can be regenerated during the ongoing apheresis session. Thus, a high clinic throughput can also be achieved using an apheresis device. Furthermore, the use of the apheresis device according to the invention is not limited by the dead volume. Typically, oversized apheresis columns but also apheresis columns connected in series are severely limited in their use for apheresis by their large dead volume. In addition, the volume of an apheresis device and thus the volume or number of apheresis columns connected in series is dictated by the human blood flow rate. Also, apheresis devices with apheresis columns connected in parallel and used simultaneously cannot be used efficiently for the removal of CRP from blood without risk to the patient due to the large dead volume. Accordingly, the bypass line (12) can be used as a plasma line.

An apheresis device (II) according to the invention described herein is characterized in that a second apheresis column is connected in parallel to a first apheresis column (4'). "Parallel" in this context means that various circulations are present side by side within the extracorporeal circulation system (2), i.e., that e.g. a first apheresis column (4') with the plasma line (8A) for the separated plasma and with the plasma line (8B) for the CRP-depleted plasma represents a first circulation system of the extracorporeal circulation system (2), and a second apheresis column (4") with the bypass line section (12') of the bypass line (12) and the bypass line section (12") of the bypass line (12) represents a second circulation system of the extracorporeal circulation system (2). "Parallel" also means that the two apheresis columns are not connected in series, i.e., not one after the other, that the outflow of the first apheresis column is introduced into the second apheresis column. Due to the parallel arrangement of the apheresis columns their capacities also do not add up.

To be distinguished from this is the serial connection of the apheresis columns, which is not according to the invention. "Serial" means that several apheresis columns are only in one circulation of the extracorporeal circulation system (2), i.e., that, for example, the first apheresis column (4') and the second apheresis column (4") together with the plasma line (8A) and the plasma line (8B) form only one circulation of the extracorporeal circulation system (2), i.e., would be connected or arranged in series.

According to the invention, the two apheresis columns (4', 4") connected in parallel to each other or arranged in parallel can only be operated alternately. "Alternately" means that the separated blood plasma is passed either through the apheresis column (4') or through the apheresis column (4") but not simultaneously through both apheresis columns (4', 4"). "Alternately" operated in this context means therapeutic CRP removal. Both apheresis columns (4' and 4") are not usable simultaneously for CRP removal. Of course, one of the two apheresis columns can be regenerated while the other is used for CRP removal at the same time. Only the simultaneous therapeutic operation for CRP removal of both apheresis columns is excluded.

The following conditions are therefore possible. Blood plasma is passed through one apheresis column to remove CRP. At the same time, the second apheresis column is ready for use and the plasma flow can be redirected to this second apheresis column as soon as the capacity of the first apheresis column is exhausted or other problems occur with the first apheresis column, or the second apheresis column has already been used for CRP removal and must be replaced or regenerated, or the second apheresis column is regenerated while the first one is removing CRP.

In embodiments of the present invention, the apheresis device (II) with two apheresis columns is therefore designed such that the apheresis columns are only alternately operable.

Thus, according to an embodiment of the apheresis device (II) according to the invention, the blood plasma can be passed either only through the first apheresis column (4') or only through the second apheresis column (4") at the same time. In further embodiments of the device according to the invention, the apheresis device is thus designed in such a way that the blood plasma is passable either only through the first apheresis column (4') or only through the second apheresis column (4") at the same time.

An embodiment of the present invention is therefore directed to an apheresis device (II) for extracorporeal removal and preferably for selective extracorporeal removal of CRP from blood comprising:

an extracorporeal circulation system (2) for blood,
a means (3) for generation and regulation of a flow of blood in the extracorporeal circulation system (2),
a cell separator (7) for separation of the blood into blood plasma and cellular components, two apheresis columns (4', 4") for affinity chromatographic removal of CRP from blood plasma,
wherein the extracorporeal circulation system (2) comprises an arterial line (5) to the cell separator (7), a plasma line (8A) from the cell separator (7) to the apheresis column (4'), a plasma line (8B) for CRP-depleted blood plasma from the apheresis column (4') to a point (P1), a cell line (9) for the separated cellular components from the cell separator (7) to the point (P1) and a venous line (6) starting from the point (P1),
a central processing unit (10) for controlling the apheresis device (1),
a connection line (11) for connection of at least one liquid container (F) to the arterial line (5) or the cell separator (7),
characterized in that
a bypass line (12) branches off from the plasma line (8A) and runs into the plasma line (8B), and the bypass line (12) comprises the second apheresis column (4"),
a waste line (13) goes off directly from the apheresis column (4') or from the plasma line (8B) in the direction of flow before the junction of the bypass line (12), and
at least one regeneration line (14) which goes off from the at least one liquid container (F) or from the at least one connection line (11) and leads to the plasma line (8A) in the direction of flow at or after the branch of the bypass line (12) or runs directly into the apheresis column (4'), and
wherein a second apheresis column (4") is connected in parallel to the first apheresis column (4') and both apheresis columns (4', 4") can only be operated alternately for CRP removal, and wherein the blood plasma is passable either only through the first apheresis column (4') or only through the second apheresis column (4") at the same time.

During alternate operation of the two apheresis columns (4', 4"), no blood plasma is passed either through the apheresis column (4') or through the apheresis column (4"). This results in the possibility of replacing one of the two apheresis columns from the apheresis device during operation of the apheresis device. "Replacing" in this context means replacing one of the two apheresis columns with a new apheresis column or regenerating one of the two apheresis columns. Regeneration of one of the two apheresis columns can be done, for example, by rinsing with a citrate solution. The use of a citrate solution is preferred for the regeneration of the apheresis columns. "During operation" in this context means that the removal of CRP from the blood continues.

An embodiment of the apheresis devices (II) of the invention as described herein therefore relates to an apheresis device in which a first apheresis column (4') is replaceable during operation of a second apheresis column (4") and the second apheresis column (4") is replaceable during operation of the first apheresis column (4').

Embodiments are also conceivable wherein a first apheresis column (4') is regenerable during operation of a second apheresis column (4") and the second apheresis column (4") is regenerable during operation of the first apheresis column (4').

Thus, in an embodiment of the present invention, the apheresis apparatus (II) is designed such that a first apheresis column (4') is replaceable or regenerable during operation of a second apheresis column (4") and the second apheresis column (4") is replaceable or regenerable during operation of the first apheresis column (4').

An embodiment of the present invention therefore relates to an apheresis device (II) for extracorporeal removal and preferably for selective extracorporeal removal of CRP from blood comprising:

an extracorporeal circulation system (2) for blood,
a means (3) for generation and regulation of a flow of blood in the extracorporeal circulation system (2),
a cell separator (7) for separation of the blood into blood plasma and cellular components, two apheresis columns (4', 4") for affinity chromatographic removal of CRP from blood plasma,
wherein the extracorporeal circulation system (2) comprises an arterial line (5) to the cell separator (7), a plasma line (8A) from the cell separator (7) to the apheresis column (4'), a plasma line (8B) for CRP-depleted blood plasma from the apheresis column (4') to a point (P1), a cell line (9) for the separated cellular components from the cell separator (7) to the point (P1) and a venous line (6) starting from the point (P1),
a central processing unit (10) for controlling the apheresis device (1),
a connection line (11) for connection of at least one liquid container (F) to the arterial line (5) or the cell separator (7),
characterized in that
a bypass line (12) branches off from the plasma line (8A) and runs into the plasma line (8B), and the bypass line (12) comprises the second apheresis column (4"),
a waste line (13) goes off directly from the apheresis column (4') or from the plasma line (8B) in the direction of flow before the junction of the bypass line (12), and
at least one regeneration line (14) which goes off from the at least one liquid container (F) or from the at least one connection line (11) and leads to the plasma line (8A) in the direction of flow at or after the branch of the bypass line (12) or runs directly into the apheresis column (4'), and
wherein a second apheresis column (4") is connected in parallel to the first apheresis column (4') and both apheresis columns (4', 4") can be operated only alternately at the same time and wherein the first apheresis column (4') is replaceable or regenerable during operation of the second apheresis column (4") and the second apheresis column (4") is replaceable or regenerable during operation of the first apheresis column (4').

The present invention further relates to an apheresis device (II) for extracorporeal removal of CRP from blood comprising:

an extracorporeal circulation system (2) for blood,
a means (3) for generation and regulation of a flow of blood in the extracorporeal circulation system (2),
a cell separator (7) for separation of the blood into blood plasma and cellular components, two apheresis columns (4', 4") for affinity chromatographic removal of CRP from blood plasma,
wherein the extracorporeal circulation system (2) comprises an arterial line (5) to the cell separator (7), a plasma line (8A) from the cell separator (7) to the apheresis column (4'), a plasma line (8B) for CRP-depleted blood plasma from the apheresis column (4') to a point (P1), a cell line (9) for the separated cellular components from the cell separator (7) to the point (P1) and a venous line (6) starting from the point (P1),
a central processing unit (10) for controlling the apheresis device (1),
a connection line (11) for connection of at least one liquid container (F) to the arterial line (5) or the cell separator (7),
characterized in that
a bypass line (12) branches off from the plasma line (8A) and runs into the plasma line (8B), and the bypass line (12) comprises the second apheresis column (4"),
a waste line (13) goes off directly from the apheresis column (4') or from the plasma line (8B) in the direction of flow before the junction of the bypass line (12), and
at least one regeneration line (14) which goes off from the at least one liquid container (F) or from the at least one connection line (11) and leads to the plasma line (8A) in the direction of flow at or after the branch of the bypass line (12) or runs directly into the apheresis column (4'), and
wherein a second apheresis column (4") is connected in parallel to the first apheresis column (4') and both apheresis columns (4', 4") are not usable simultaneously for CRP removal, and wherein one of the apheresis columns (4', 4") can be regenerated simultaneously to the removal of CRP by the other apheresis column.

Therefore, according to an embodiment of the present invention, the apheresis device (II) is designed such that the first apheresis column (4') is replaceable during operation of the second apheresis column (4") and the apheresis column is designed such that it is regenerable and the second apheresis column (4") is replaceable during operation of the first apheresis column (4') and the apheresis column (4") is designed such that the apheresis column (4") is regenerable.

The second apheresis column (4") connected in parallel to the first apheresis column (4') can be integrated in the bypass line, i.e. the bypass line (12) is composed of a bypass line section (12') and a bypass line section (12"), with the second apheresis column (4") located between said bypass line sections.

The present invention therefore also relates to an apheresis device (II) for extracorporeal removal of CRP from blood comprising:

an extracorporeal circulation system (2) for blood,
a means (3) for generation and regulation of a flow of blood in the extracorporeal circulation system (2),
a cell separator (7) for separation of the blood into blood plasma and cellular components, two apheresis columns (4', 4") for affinity chromatographic removal of CRP from blood plasma,
wherein the extracorporeal circulation system (2) comprises an arterial line (5) to the cell separator (7), a plasma line (8A) from the cell separator (7) to the apheresis column (4'), a plasma line (8B) for CRP-depleted blood plasma from the apheresis column (4') to a point (P1),
a cell line (9) for the separated cellular components from the cell separator (7) to the point (P1) and a venous line (6) starting from the point (P1),
a central processing unit (10) for controlling the apheresis device (1),
a connection line (11) for connection of at least one liquid container (F) to the arterial line (5) or the cell separator (7),
characterized in that
a bypass line section (12') of the bypass line (12) branches off from the plasma line (8A) and runs into the second apheresis column (4") and the bypass line section (12") of the bypass line (12) starting from the apheresis column (4") runs into the plasma line (8B),
a waste line (13) goes off directly from the apheresis column (4') or from the plasma line (8B) in the direction of flow before the junction of the bypass line (12), and
at least one regeneration line (14) which goes off from the at least one liquid container (F) or from the at least one connection line (11) and leads to the plasma line (8A) in the direction of flow at or after the branch of the bypass line (12) or runs directly into the apheresis column (4'), and
wherein a second apheresis column (4") is connected in parallel to the first apheresis column (4') and both apheresis columns (4', 4") cannot be used simultaneously for CRP removal.

An embodiment of the present invention therefore relates to an apheresis device (II) for extracorporeal removal and preferably for selective extracorporeal removal of CRP from blood comprising:
an extracorporeal circulation system (2) for blood,
a means (3) for generation and regulation of a flow of blood in the extracorporeal circulation system (2),
a cell separator (7) for separation of the blood into blood plasma and cellular components, two apheresis columns (4', 4") for affinity chromatographic removal of CRP from the blood plasma,
wherein the extracorporeal circulation system (2) comprises an arterial line (5) to the cell separator (7), a plasma line (8A) from the cell separator (7) to the apheresis column (4'), a plasma line (8B) for CRP-depleted blood plasma from the apheresis column (4') to a point (P1), a cell line (9) for the separated cellular components from the cell separator (7) to the point (P1) and a venous line (6) starting from the point (P1),
a central processing unit (10) for controlling the apheresis device (1),
two connection lines (11) for connection of at least one liquid container (F) to the arterial line (5) or the cell separator (7),
characterized in that
a bypass line (12) branches off from the plasma line (8A) and runs into the plasma line (8B), and the bypass line (12) comprises the second apheresis column (4")
a waste line (13) goes off directly from the apheresis column (4') or from the plasma line (8B) in the direction of flow before the junction of the bypass line (12), and
at least one regeneration line (14) which goes off from the at least one liquid container (F) or from the at least two connection lines (11) and leads to the plasma line (8A) in the direction of flow at or after the branch of the bypass line (12) or runs directly into the apheresis column (4'), and
wherein a second apheresis column (4") is connected in parallel to the first apheresis column (4') and both apheresis columns (4', 4") cannot be used simultaneously for CRP removal (i.e. are only operable alternately).

According to an embodiment of the present invention, it is particularly preferred if the apheresis device (II) according to the invention has two connection lines (11',11") each for connection of at least one liquid container (F), wherein the connection lines (11', 11") run independently of each other into the arterial line (5) or directly into the cell separator (7). Consequently, both connection lines (11', 11") run into the arterial line (5) or both connection lines (11', 11") run directly into the cell separator (7) or, particularly preferably, one connection line (11') runs into the arterial line (5) and the other connection line (11") runs directly into the cell separator (7). This allows the two connection lines (11', 11") to be connected to different liquid containers. It is particularly preferred if one of the two connection lines (e.g. 11') is connected to a liquid container containing a physiological salt solution (e.g. NaCl solution), while the second of the two connection lines (e.g. 11") is connected to a liquid container containing a citrate solution.

A further embodiment of the present invention is an apheresis device (II) for extracorporeal removal and preferably for selective extracorporeal removal of CRP from blood comprising:
an extracorporeal circulation system (2) for blood,
a means (3) for generation and regulation of a flow of blood in the extracorporeal circulation system (2),
a cell separator (7) for separation of the blood into blood plasma and cellular components, two apheresis columns (4', 4") for affinity chromatographic removal of CRP from the blood plasma,
wherein the extracorporeal circulation system (2) comprises an arterial line (5) to the cell separator (7), a plasma line (8A) from the cell separator (7) to the apheresis column (4'), a plasma line (8B) for CRP-depleted blood plasma from the apheresis column (4') to a point (P1), a cell line (9) for the separated cellular components from the cell separator (7) to the point (P1) and a venous line (6) starting from the point (P1),
a central processing unit (10) for controlling the apheresis device (1),
two connection lines (11',11") each for connection of at least one liquid container (F) to the arterial line (5) or the cell separator (7),
characterized in that
a bypass line (12) branches off from the plasma line (8A) and runs into the plasma line (8B), and the bypass line (12) comprises the second apheresis column (4"),
a waste line (13) goes off directly from the apheresis column (4') or from the plasma line (8B) in the direction of flow before the junction of the bypass line (12), and
at least one regeneration line (14) which goes off from the at least one liquid container (F) or from the at least one connection line (11) and leads to the plasma line (8A) in the direction of flow at or after the branch of the bypass line (12) or runs directly into the apheresis column (4'), and
wherein a second apheresis column (4") is connected in parallel to the first apheresis column (4') and both apheresis columns (4', 4") cannot be used simultaneously for CRP removal, i.e. are only operable alternately.

According to a further embodiment of the present invention, the apheresis device (II) comprises a waste line (13') which goes off directly from apheresis column (4') or goes off from plasma line (8B) in the direction of flow before the junction of the bypass line section (12") of the bypass line in the plasma line (8B) and a waste line (13"), which directly goes off from the apheresis column (4") or from the bypass line section (12") in the direction of flow before the junction in the plasma line (8B).

The present invention thus also relates to an apheresis device (II) for extracorporeal removal and preferably for selective extracorporeal removal of CRP from blood comprising:
- an extracorporeal circulation system (2) for blood,
- a means (3) for generation and regulation of a flow of blood in the extracorporeal circulation system (2),
- a cell separator (7) for separation of the blood into blood plasma and cellular components,
- two apheresis columns (4', 4") for affinity chromatographic removal of CRP from the blood plasma,
- wherein the extracorporeal circulation system (2) comprises an arterial line (5) to the cell separator (7), a plasma line (8A) from the cell separator (7) to the apheresis column (4'), a plasma line (8B) for CRP-depleted blood plasma from the apheresis column (4') to a point (P1),
- a cell line (9) for the separated cellular components from the cell separator (7) to the point (P1) and a venous line (6) starting from the point (P1),
- a central processing unit (10) for controlling the apheresis device (1),
- a connection line (11) for connection of at least one liquid container (F) to the arterial line (5) or the cell separator (7),
- characterized in that
- a bypass line section (12') of the bypass line (12) branches off from the plasma line (8A) and runs into the second apheresis column (4") and the bypass line section (12") of the bypass line (12) starting from the apheresis column (4") runs into the plasma line (8B),
- a waste line (13') which goes off directly from apheresis column (4') or goes off from plasma line (8B) in the direction of flow before the junction of the bypass line section (12") of the bypass line in the plasma line (8B) and a waste line (13"), which goes off directly from the apheresis column (4") or from the bypass line section (12") of the bypass line (12) in the direction of flow before the junction in the plasma line (8B),
- and
- at least one regeneration line (14) which goes off from the at least one liquid container (F) or from the at least one connection line (11) and leads to the plasma line (8A) or to the bypass line section (12') in the direction of flow at or after the branch of the bypass line section (12') of the bypass line (12) or runs directly into the apheresis column (4') or into the apheresis column (4"), and
- wherein a second apheresis column (4") is connected in parallel to the first apheresis column (4') and both apheresis columns (4', 4") cannot be used simultaneously for CRP removal, i.e. are only operable alternately.

According to a further embodiment of the present invention, the apheresis device (II) further contains at least one regeneration line (14) that goes off from the at least one liquid container (F) or the at least one connection line (11) and leads into the plasma line (8A) or into the bypass line section (12') of the bypass line (12) or leads directly into the apheresis column (4') or leads directly into the apheresis column (4"). According to a further embodiment of the present invention, the apheresis device (II) further contains at least one regeneration line (14) that runs into the bypass line section (12') in a region from the point (P2) and the apheresis column (4') or into the plasma line (8A) in a region from the point (P2) and the apheresis column (4") or runs directly into the apheresis column (4') or directly into the apheresis column (4").

In a particularly preferred embodiment of the present invention, the apheresis device (II) comprises a waste line (13') which goes off directly from the apheresis column (4') or goes off from the plasma line (8B) in the direction of flow before the junction of the bypass line section (12") of the bypass line (12) and at least one regeneration line (14), which goes off from the at least one liquid container (F) or the at least one connection line (11) and leads into the bypass line section (12') or into the plasma line (8A) or runs directly into the apheresis column (4') or directly into the apheresis column (4").

Particularly preferred is an apheresis device (II) for extracorporeal removal and preferably for selective extracorporeal removal of CRP from blood comprising:
- an extracorporeal circulation system (2) for blood,
- a means (3) for generation and regulation of a flow of blood in the extracorporeal circulation system (2),
- a cell separator (7) for separation of the blood into blood plasma and cellular components, two apheresis columns (4', 4") for affinity chromatographic removal of CRP from the blood plasma,
- wherein the extracorporeal circulation system (2) comprises an arterial line (5) to the cell separator (7), a plasma line (8A) from the cell separator (7) to the apheresis column (4'), a plasma line (8B) for CRP-depleted blood plasma from the apheresis column (4') to a point (P1), a cell line (9) for the separated cellular components from the cell separator (7) to the point (P1) and a venous line (6) starting from the point (P1),
- a central processing unit (10) for controlling the apheresis device (1),
- a connection line (11) for connection of at least one liquid container (F) to the arterial line (5) or the cell separator (7),
- a bypass line section (12') of the bypass line (12) branches off from the plasma line (8A) and runs into the second apheresis column (4") and the bypass line section (12") of the bypass line (12) starting from the apheresis column (4") runs into the plasma line (8B),
- a waste line (13) which goes off directly from apheresis column (4') or goes off from plasma line (8B) in the direction of flow before the junction of the bypass line (12), and
- at least one regeneration line (14) which goes off from the at least one liquid container (F) or from the at least one connection line (11) and leads to the plasma line (8A) in the direction of flow at or after the branch of the bypass line section (12') of the bypass line (12) or into the bypass line section (12') of the bypass line (12) or runs directly into the apheresis column (4') or into the apheresis column (4"), and wherein a second apheresis column (4") is connected in parallel to the first apheresis column (4') and both apheresis columns (4', 4") cannot be used simultaneously for CRP removal.

In a particularly preferred embodiment of the present invention, the apheresis device (II) comprises a waste line (12') which goes off directly from the apheresis column (4') or goes off from the plasma line (8B) in the direction of flow before the junction of the bypass line section (12") of the bypass line, a waste line (13") which goes off directly from the apheresis column (4") or which goes off from the bypass line section (12") of the bypass line (12) in the direction of flow before the junction of the bypass line section (12') of the bypass line, and at least one regeneration line (14) which goes off from the at least one liquid container (F) or the at least one connection line (11) and leads into the plasma line (8A) or into the bypass line section (12') of the bypass line (12) or runs directly into the apheresis column (4') or directly into the apheresis column (4").

A particularly preferred embodiment of the underlying invention relates to an apheresis device (II) for extracorporeal removal and preferably for selective extracorporeal removal of CRP from blood comprising:
an extracorporeal circulation system (2) for blood,
a means (3) for generation and regulation of a flow of blood in the extracorporeal circulation system (2),
a cell separator (7) for separation of the blood into blood plasma and cellular components,
two apheresis columns (4', 4") for affinity chromatographic removal of CRP from the blood plasma,
wherein the extracorporeal circulation system (2) comprises an arterial line (5) to the cell separator (7), a plasma line (8A) from the cell separator (7) to the apheresis column (4'), a plasma line (8B) for CRP-depleted blood plasma from the apheresis column (4') to a point (P1),
a cell line (9) for the separated cellular components from the cell separator (7) to the point (P1) and a venous line (6) starting from the point (P1),
a central processing unit (10) for controlling the apheresis device (1),
a connection line (11) for connection of at least one liquid container (F) to the arterial line (5) or the cell separator (7),
characterized in that
a bypass line section (12') of the bypass line (12) branches off from the plasma line (8A) and runs into the second apheresis column (4") and the bypass line section (12") of the bypass line (12) starting from the apheresis column (4") runs into the plasma line (8B),
a waste line (13') which goes off directly from apheresis column (4') or goes off from plasma line (8B) in the direction of flow before the junction of the bypass line section (12') of the bypass line (12), a waste line (13") which goes off directly from apheresis column (14") or from the bypass line section (12") of the bypass line (12) in the direction of flow before the junction of the bypass line section (12') of the bypass line (12),
and
at least one regeneration line (14) which goes off from the at least one liquid container (F) or from the at least one connection line (11) and leads to the plasma line (8A) in the direction of flow at or after the branch of the bypass line section (12') of the bypass line (12) or to the bypass line section (12') of the bypass line (12) or runs directly into the apheresis column (4') or into the apheresis column (4"),
and
wherein a second apheresis column (4") is connected in parallel to the first apheresis column (4') and both apheresis columns (4', 4") cannot be used simultaneously for CRP removal.

Furthermore, embodiments of the apheresis device (II) according to the invention are possible, wherein the at least one regeneration line (13) runs to a point (P7) and from the point (P7) a line (14') leads to the point (P2) or runs into the plasma line (8A) and from the point (P7) a line (14") leads into plasma line (8A) (see FIG. 11).

In the case that the at least one regeneration line (14) for the rinsing solution runs into the plasma line (8A) between the point (P2) and the apheresis column (4') or in the case, that the at least one regeneration line (14) runs into the bypass line section (12') of the bypass line (12) between the point (P2) and the apheresis column (4"), the rinsing solution can be used either for the apheresis column (4') only or for the apheresis column (4"). The regeneration line (14) is thus either selective to the apheresis column (4') or selective to the apheresis column (4").

Embodiments of the apheresis device (II) according to the invention with two, three or more regeneration lines (14'. 14", 14'", etc.) are also possible, wherein in these cases these two, three or more regeneration lines run independently of each other into the plasma line (8A) [i.e., from the point (P2) to the apheresis column (4')] or into the bypass line section (12') [i.e., from the point (P2) to the apheresis column (4")] or into the apheresis column (4') or into the apheresis column (4"). "Independent of each other" in this context means, for example, that in an embodiment of the apheresis devices according to the invention with two regeneration lines (14', 14"), one regeneration line (14') runs into the plasma line (8A) between the point (P2) and the apheresis column (4') and the other regeneration line (14") runs directly into the apheresis column (4"), but also that both regeneration lines (14', 14") can run into the plasma line (8A) between the point (P2) and the apheresis column (4'). A further possibility is that one regeneration line (14') runs into the extracorporeal circulation system (2) at the point (P2) and the other regeneration line (14") runs into the bypass line section (12') of the bypass line (12) between the point (P2) and the apheresis column (4"). It is also conceivable that one regeneration line (14') runs into the extracorporeal circulation system at the point (P2) and the other regeneration line (14") runs into the apheresis column (4"). It is also possible that one regeneration line (14') runs into the other regeneration line (14"). However, in the presence of two or more regeneration lines (14', 14", 14'", etc.), it is preferred that all regeneration lines (14',14", 14'", etc.) run into the extracorporeal circulation system (2) at point (P2).

It is further preferred if one regeneration line (14') runs into the bypass line section (12') of the bypass line (12) between the point (P2) and the apheresis column (4') and the other regeneration line (14") runs into the bypass line section (12') of the bypass line (12) between the point P2 and the apheresis column (4"). It is further preferred if the regeneration line (14') runs into the apheresis column (4') and the other regeneration line (14") runs into the apheresis column (4"). Here, the regeneration line (14') is selective to the first apheresis column (4') and the regeneration line is selective to the second apheresis column (4").

According to a particularly preferred embodiment of the present invention, the apheresis device (II) therefore further comprises a regeneration line (14') for a rinsing solution selective to the first apheresis column (4') and/or further comprises a regeneration line (14") for a rinsing solution selective to the second apheresis column (4").

An embodiment of the present invention therefore relates to an apheresis device (II) for extracorporeal removal and preferably for selective extracorporeal removal of CRP from blood comprising:
- an extracorporeal circulation system (2) for blood,
- a means (3) for generation and regulation of a flow of blood in the extracorporeal circulation system (2),
- a cell separator (7) for separation of the blood into blood plasma and cellular components,
- two apheresis columns (4', 4") for affinity chromatographic removal of CRP from the blood plasma,
- wherein the extracorporeal circulation system (2) comprises an arterial line (5) to the cell separator (7), a plasma line (8A) from the cell separator (7) to the apheresis column (4'), a plasma line (8B) for CRP-depleted blood plasma from the apheresis column (4') to a point (P1), a cell line (9) for the separated cellular components from the cell separator (7) to the point (P1) and a venous line (6) starting from the point (P1),
- a central processing unit (10) for controlling the apheresis device (1),
- a connection line (11) for connection of at least one liquid container (F) to the arterial line (5) or the cell separator (7),
- characterized in that
- a bypass line (12) branches off from the plasma line (8A) and runs into the plasma line (8B), and the bypass line (12) comprises the second apheresis column (4"),
- a waste line (13') which goes off directly from apheresis column (4') or goes off from plasma line (8B) in the direction of flow before the junction of the bypass line (12), and
- a regeneration line (14') for a rinsing solution selective to the first apheresis column (4') and/or a regeneration line (14") for a rinsing solution selective to the second apheresis column (4"),
- and
- wherein a second apheresis column (4") is connected in parallel to the first apheresis column (4') and both apheresis columns (4', 4") cannot be used simultaneously for CRP removal, i.e. are only operable alternately.

As mentioned above, the regeneration solution required for the regeneration of the apheresis columns can be fed into the extracorporeal circulation system (2) via the regeneration line (14), and thus a regeneration solution (e.g. a citrate solution, a TRIS-glycine solution, or a sodium chloride solution) can also be used in addition to the rinsing solution. The rinsing solution can, but does not have to, serve to regenerate the first apheresis column (4') and/or apheresis column (4"), but in addition to the above-mentioned function, has the task of displacing the blood plasma from the plasma line (8A) in the region from point (P2) to the apheresis column (4') as well as from the plasma line (8B) from the apheresis column (4') to point (P8) or displacing the blood plasma from the bypass line section (12') of the bypass line (12) in the region from point (P2) to the apheresis column (4") as well as from the bypass line section (12") of the bypass line (12) from the apheresis column (4") to the point (P8) and thus leading back into the blood circulation of the patient, before the regeneration solution is introduced, which after flowing through one of the two apheresis columns (4', 4") is then discarded via the drain line (13', 13").

Thus, it is conceivable that the apheresis columns (4', 4") connected in parallel can not only be operated alternately, but are also regenerated alternately.

In apheresis devices (II) according to the invention as described herein, the first apheresis column (4') may be replaceable or regenerable during operation of the second apheresis column (4") and the second apheresis column (4") may be replaceable or regenerable during operation of the first apheresis column (4').

An embodiment of the present invention therefore directed to an apheresis device (II) for extracorporeal removal and preferably for selective extracorporeal removal of CRP from blood or blood plasma comprising:
- an extracorporeal circulation system (2) for blood,
- a means (3) for generation and regulation of a flow of blood in the extracorporeal circulation system (2),
- a cell separator (7) for separation of the blood into blood plasma and cellular components,
- two apheresis columns (4', 4") for affinity chromatographic removal of CRP from the blood plasma,
- wherein the extracorporeal circulation system (2) comprises an arterial line (5) to the cell separator (7), a plasma line (8A) from the cell separator (7) to the apheresis column (4'), a plasma line (8B) for CRP-depleted blood plasma from the apheresis column (4') to a point (P1),
- a cell line (9) for the separated cellular components from the cell separator (7) to the point (P1) and a venous line (6) starting from the point (P1),
- a central processing unit (10) for controlling the apheresis device (II),
- a connection line (11) for connection of at least one liquid container (F) to the arterial line (5) or the cell separator (7),
- characterized in that
- a bypass line section (12') of the bypass line (12) branches off from the plasma line (8A) and runs into the second apheresis column (4') and the bypass line section (12") of the bypass line (12) starting from the apheresis column (4") runs into the plasma line (8B),
- a waste line (13') which goes off directly from apheresis column (4') or goes off from plasma line (8B) in the direction of flow before the junction of the bypass line section (12') of the bypass line (12), a waste line (13") which goes off directly from apheresis column (14") or from the bypass line section (12") of the bypass line (12) in the direction of flow before the junction of the bypass line section (12') of the bypass line (12),
- and
- at least one regeneration line (14) which goes off from the at least one liquid container (F) or from the at least one connection line (11) and leads to the plasma line (8A) in the direction of flow at or after the branch of the bypass line section (12') of the bypass line (12) or to the bypass line section (12') of the bypass line (12) or runs directly into the apheresis column (4') or into the apheresis column (4"),
- wherein a second apheresis column (4") is connected in parallel to the first apheresis column (4') and both apheresis columns (4', 4") are only operable alternately, and wherein the first apheresis column (4') is replaceable or regenerable during operation of the second apheresis column (4") and the second apheresis column (4") is replaceable or regenerable during operation of the first apheresis column (4').

Furthermore, embodiments of the present invention are conceivable in which the apheresis device has a regeneration line (14) per liquid container (F), which go off from the respective liquid container (F) or its connection line (11) and which each lead into the plasma line (8A) or into the bypass line section (12') of the bypass line (12) or directly into the apheresis column (4') or directly into the apheresis column (4").

A particularly preferred embodiment of the present invention relates to an apheresis device (II) for extracorporeal removal and preferably for selective extracorporeal removal of CRP from blood comprising:

an extracorporeal circulation system (2) for blood,
a means (3) for generation and regulation of a flow of blood in the extracorporeal circulation system (2),
a cell separator (7) for separation of the blood into blood plasma and cellular components,
two apheresis columns (4', 4") for affinity chromatographic removal of CRP from the blood plasma,
wherein the extracorporeal circulation system (2) comprises an arterial line (5) to the cell separator (7), a plasma line (8A) from the cell separator (7) to the apheresis column (4'), a plasma line (8B) for CRP-depleted blood plasma from the apheresis column (4') to a point (P1),
a cell line (9) for the separated cellular components from the cell separator (7) to the point (P1) and a venous line (6) starting from the point (P1),
a central processing unit (10) for controlling the apheresis device (II),
a connection line (11) for connection of at least one liquid container (F) to the arterial line (5) or the cell separator (7),
characterized in that
a bypass line section (12') of the bypass line (12) branches off from the plasma line (8A) and runs into the second apheresis column (4') and the bypass line section (12") of the bypass line (12) starting from the apheresis column (4") runs into the plasma line (8B),
a waste line (13') which goes off directly from apheresis column (4') or goes off from plasma line (8B) in the direction of flow before the junction of the bypass line section (12') of the bypass line (12), a waste line (13") which goes off directly from apheresis column (14") or from the bypass line section (12") of the bypass line (12) in the direction of flow before the junction of the bypass line section (12') of the bypass line (12),
and a regeneration line (14) is contained per liquid container (F), which go off from the respective liquid container (F) or from its connection line (11) and lead to the plasma line (8A) in the direction of flow at or after the branch of the bypass line section (12') of the bypass line (12) or to the bypass line section (12') of the bypass line (12) or run directly into the apheresis column (4') or into the apheresis column (4"),
wherein a second apheresis column (4") is connected in parallel to the first apheresis column (4') and both apheresis columns (4', 4") cannot be used simultaneously for CRP removal.

Furthermore, embodiments of the apheresis device (II) are preferred in which the apheresis device (II) has at least two connection lines (11) each for connection of at least one liquid container (F) to the arterial line (5) or the cell separator (7), and wherein there is a regeneration line (13) per liquid container (F), which go off from the respective liquid container (F) or its connection line (11) and which each lead into the plasma line (8A) or into the bypass line section (12') of the bypass line (12) or directly into the apheresis column (4') or directly into the apheresis column (4").

According to some embodiments of the present invention, preferably that the at least one regeneration line (14) leading into the plasma line (8A) or into the bypass line section (12') of the bypass line (12), or leading directly into the apheresis column (4') or leading directly into the apheresis column (4"), starts from a point (P5) in the at least one connection line (11).

The present invention therefore also relates to an apheresis device (II) for extracorporeal removal and preferably for selective extracorporeal removal of CRP from blood comprising:

an extracorporeal circulation system (2) for blood,
a means (3) for generation and regulation of a flow of blood in the extracorporeal circulation system (2),
a cell separator (7) for separation of the blood into blood plasma and cellular components,
two apheresis columns (4', 4") for affinity chromatographic removal of CRP from the blood plasma,
wherein the extracorporeal circulation system (2) comprises an arterial line (5) to the cell separator (7), a plasma line (8A) from the cell separator (7) to the apheresis column (4'), a plasma line (8B) for CRP-depleted blood plasma from the apheresis column (4') to a point (P1),
a cell line (9) for the separated cellular components from the cell separator (7) to the point (P1) and a venous line (6) starting from the point (P1),
a central processing unit (10) for controlling the apheresis device (II),
a connection line (11) for connection of at least one liquid container (F) to the arterial line (5) or the cell separator (7),
characterized in that
a bypass line section (12') of the bypass line (12) branches off from the plasma line (8A) and runs into the second apheresis column (4') and the bypass line section (12") of the bypass line (12) starting from the apheresis column (4") runs into the plasma line (8B),
a waste line (13) which goes off directly from apheresis column (4') or goes off from plasma line (8B) in the direction of flow before the junction of the bypass line (12), and
at least one regeneration line (14) which goes off from a point (P5) in the at least one connection line (11) for connection of at least one liquid container (F) to the arterial line (5) or the cell separator (7) and leads to the plasma line (8A) in the direction of flow at or after the branch of the bypass line section (12') of the bypass line (12) or to the bypass line section (12') of the bypass line (12) or runs directly into the apheresis column (4') or into the apheresis column (4"),
and
wherein a second apheresis column (4") is connected in parallel to the first apheresis column (4') and both apheresis columns (4', 4") cannot be used simultaneously for CRP removal.

An apheresis device (II) is preferred, wherein the apheresis device (II) has two connection lines (11', 11') each for connection of one liquid container (F1, F2) to the arterial line (5) or the cell separator (7), and two regeneration lines (14', 14") that go off from two liquid containers (F1, F2) or the two connection lines (11', 11") and lead into the plasma line (8A) or into the bypass line section (12') of the bypass line (12) or directly into apheresis column (4') or directly the apheresis column (4").

A particularly preferred embodiment of the underlying invention therefore is directed to an apheresis device (II) for extracorporeal removal and preferably for selective extracorporeal removal of CRP from blood comprising:
- an extracorporeal circulation system (2) for blood,
- a means (3) for generation and regulation of a flow of blood in the extracorporeal circulation system (2),
- a cell separator (7) for separation of the blood into blood plasma and cellular components,
- two apheresis columns (4', 4") for affinity chromatographic removal of CRP from the blood plasma,
- wherein the extracorporeal circulation system (2) comprises an arterial line (5) to the cell separator (7), a plasma line (8A) from the cell separator (7) to the apheresis column (4'), a plasma line (8B) for CRP-depleted blood plasma from the apheresis column (4') to a point (P1),
- a cell line (9) for the separated cellular components from the cell separator (7) to the point (P1) and a venous line (6) starting from the point (P1),
- a central processing unit (10) for controlling the apheresis device (II),
- two connection lines (11', 11") for connection of two liquid containers (F1, F2) to the arterial line (5) or the cell separator (7),
- characterized in that
- a bypass line section (12') of the bypass line (12) branches off from the plasma line (8A) and runs into the second apheresis column (4') and the bypass line section (12") of the bypass line (12) starting from the apheresis column (4") runs into the plasma line (8B),
- a waste line (13') which goes off directly from apheresis column (4') or goes off from plasma line (8B) in the direction of flow before the junction of the bypass line section (12') of the bypass line (12), a waste line (13") which goes off directly from apheresis column (14") or from the bypass line section (12") of the bypass line (12) in the direction of flow before the junction of the bypass line section (12') of the bypass line (12),
- and
- two regeneration lines (14', 14") which go off from the two liquid containers (F1, F2) or the two connection lines (11', 11") and leads to the plasma line (8A) in the direction of flow at or after the branch of the bypass line section (12') of the bypass line (12) or to the bypass line section (12') of the bypass line (12) or runs directly into the apheresis column (4') or into the apheresis column (4"),
- and
- wherein the second apheresis column (4") is connected in parallel to the first apheresis column (4') and both apheresis columns (4', 4") cannot be used simultaneously for CRP removal, i.e. are only operable alternately.

Embodiments are also conceivable in which a regeneration line (14), which leads into the plasma line (8A) or into the bypass line section (12') of the bypass line (12) or directly into the apheresis column (4') or directly into the apheresis column (4") and which starts from a point (P5) in the at least one connection line (11), has at least one additional connection for a liquid container (FIG. 16).

In embodiments of the present invention with various of connection lines (11', 11", 11"', etc.) and various regeneration lines (14', 14", etc.), it is possible that one connection line is in communication with one regeneration line at a time, which in turn runs after the point (P2) into the plasma line (8A) or into the bypass line section (12') of the bypass line (12) or directly into apheresis column (4') or directly into the apheresis column (4"). Here, each regeneration line can run into the plasma line (8A) or into the bypass line section (12') of the bypass line (12) or directly into apheresis column (4') or directly into apheresis column (4") independently of the other regeneration lines. However, it is preferred if all regeneration lines run directly into the apheresis columns (4'; 4"), preferably at point (P2) in the extracorporeal circulation system (2). One such exemplary embodiment is explained with reference to FIG. 7. Herein, the apheresis device (II) has a first connection line (11'), which firstly leads into the arterial line (5) and from which secondly a first regeneration line (14') branches off at point (P5'). The apheresis device (II) also has a second connection line (11"), which firstly leads directly into the cell separator (7) and from which secondly a second regeneration line (14") branches off at point (P5"). In this embodiment, both regeneration lines run into the extracorporeal circulation system (2) at point (P2).

An apheresis device (II) is therefore preferred, which comprises two connection lines (11', 11") each for connection at least one liquid container (F) to the arterial line (5) or the cell separator (7), and wherein the at least one regeneration line (14), which leads into the plasma line (8A) or into the bypass line section (12') of the bypass line (12) or directly into the apheresis column (4') or directly into the apheresis column (4"), connects at a point (P5') to the connection line (11') and at a point (P5") to the connection line (11").

A preferred embodiment of the underlying invention therefore relates to an apheresis device (II) for extracorporeal removal and preferably for selective extracorporeal removal of CRP from blood comprising:
- an extracorporeal circulation system (2) for blood,
- a means (3) for generation and regulation of a flow of blood in the extracorporeal circulation system (2),
- a cell separator (7) for separation of the blood into blood plasma and cellular components,
- two apheresis columns (4', 4") for affinity chromatographic removal of CRP from the blood plasma,
- wherein the extracorporeal circulation system (2) comprises an arterial line (5) to the cell separator (7), a plasma line (8A) from the cell separator (7) to the apheresis column (4'), a plasma line (8B) for CRP-depleted blood plasma from the apheresis column (4') to a point (P1),
- a cell line (9) for the separated cellular components from the cell separator (7) to the point (P1) and a venous line (6) starting from the point (P1),
- a central processing unit (10) for controlling the apheresis device (II),
- two connection lines (11', 11") each for connection of at least one liquid container (F) to the arterial line (5) or the cell separator (7),
- characterized in that
- a bypass line section (12') of the bypass line (12) branches off from the plasma line (8A) and runs into the second apheresis column (4') and the bypass line section (12") of the bypass line (12) starting from the apheresis column (4") runs into the plasma line (8B),
- a waste line (13') which goes off directly from apheresis column (4') or goes off from plasma line (8B) in the direction of flow before the junction of the bypass line section (12') of the bypass line (12), a waste line (13")

which goes off directly from apheresis column (14") or from the bypass line section (12") of the bypass line (12) in the direction of flow before the junction of the bypass line section (12') of the bypass line (12), and at least one regeneration line (14), which leads into to the plasma line (8A) or the bypass line section (12') of the bypass line (12) or runs directly into the apheresis column (4') or into the apheresis column (4"), connects to the connection line (11') at a point (P5') and to the connection line (11") at a point (P5").

which goes off from the at least liquid container (F) or the at least one connection line (11) and leads into the plasma line (8A) tin the direction of flow at or preferably after the branch of the bypass line section (12') of the bypass line (12) or to the bypass line section (12') of the bypass line (12) or runs directly into the apheresis column (4') or into the apheresis column (4"), and wherein a second apheresis column (4") is connected in parallel to the first apheresis column (4') and both apheresis columns (4', 4") cannot be used simultaneously for CRP removal.

Thus, embodiments of the apheresis device are particularly preferred, wherein the apheresis device (II) comprises two connection lines (11', 11") each for connection of one liquid container (F1, F2) to the arterial line (5) or the cell separator (7), and wherein the at least one regeneration line (14) leads into the plasma line (8A) or into the bypass line section (12') of the bypass line (12) or directly into the apheresis column (4') or directly into the apheresis column (4"), connects at a point (P5') to the connection line (11') and at a point (P5") to the connection line (11"), and wherein a regeneration line (14') leads from the liquid container (F1) or from the connection line (11') leaving the liquid container (F1) to the apheresis column (4') or to the apheresis column (4") or to the plasma line (8A') or to the plasma line (8A") and a regeneration line (14") leads from the liquid container (F2) or the connection line (11") leaving the liquid container (F2) to the apheresis column (4') or to the apheresis column (4") or to the plasma line (8A) or to the bypass line section (12') of the bypass line (12) or to the regeneration line (14').

Preferably, the liquid container (F1) contains a physiological solution, and the liquid container (F2) contains a citrate solution.

Thus, it is particularly preferred if the apheresis device (II) has a connection line (11') for connection of a liquid container (F1) and a connection line (11") for connection of a liquid container (F2), and the connection line (11') runs into the arterial line (5) or into the cell separator (7), and the connection line (11") runs into the arterial line (5) or into the cell separator (7) or into the connection line (11') and thus ultimately also into the arterial line (5) or into the cell separator (7), and a regeneration line (14') leads from the liquid container (F1) or from the connection line (11') to the apheresis column (4') or to the apheresis column (4") or to the plasma line (8A) or to the plasma line (8A") and a regeneration line (14") leads from the liquid container (F2) or from the connection line (11") to the apheresis column (4') or to the apheresis column (4") or to the plasma line (8A') or to the bypass line section (12') of the bypass line section (12') or in the regeneration line (14').

Embodiments of the apheresis device (II) are therefore particularly preferred, in which the apheresis device (II) has a connection line (11') for connection of a liquid container (F1) to the arterial line (5) or the cell separator (7) and a connection line (11") for connection of a liquid container (F2) to the arterial line (5) or the cell separator (7), and wherein a regeneration line (14') goes off from the liquid container (F1) or the connection line (11') and leads into the plasma line (8A) or the bypass line section (12') of the bypass line (12) or directly into the apheresis column (4') or directly into the apheresis column (4") and a regeneration line (14") goes off from a liquid container (F2) or the connection line (11") and leads into the plasma line (8A) or into the bypass line section (12') of the bypass line (12) or into the regeneration line (14') or directly into the apheresis column (4') or directly into the apheresis column (4").

A preferred embodiment of the underlying invention relates to an apheresis device (II) for extracorporeal removal and preferably for selective extracorporeal removal of CRP from blood comprising:

an extracorporeal circulation system (2) for blood, a means (3) for generation and regulation of a flow of blood in the extracorporeal circulation system (2), a cell separator (7) for separation of the blood into blood plasma and cellular components, two apheresis columns (4', 4") for affinity chromatographic removal of CRP from the blood plasma, wherein the extracorporeal circulation system (2) comprises an arterial line (5) to the cell separator (7), a plasma line (8A) from the cell separator (7) to the apheresis column (4'), a plasma line (8B) for CRP-depleted blood plasma from the apheresis column (4') to a point (P1), a cell line (9) for the separated cellular components from the cell separator (7) to the point (P1) and a venous line (6) starting from the point (P1), a central processing unit (10) for controlling the apheresis device (II), a connection line (11') for connection of a liquid container (F1) to the arterial line (5) or the cell separator (7), and a connection line (11") for connection of a liquid container (F2) to the arterial line (5) or the cell separator (7), characterized in that a bypass line section (12') of the bypass line (12) branches off from the plasma line (8A) and runs into the second apheresis column (4') and the bypass line section (12") of the bypass line (12) starting from the apheresis column (4") runs into the plasma line (8B), a waste line (13') which goes off directly from apheresis column (4') or goes off from plasma line (8B) in the direction of flow before the junction of the bypass line section (12') of the bypass line (12), a waste line (13") which goes off directly from apheresis column (14") or from the bypass line section (12") of the bypass line (12) in the direction of flow before the junction of the bypass line section (12') of the bypass line (12), and a regeneration line (14') goes off from the liquid container (F1) or the connection line (11') and leads in the direction of flow at or preferably after the branch of the bypass line section (12') of the bypass line (12) to the plasma line (8A) or to the bypass line section (12') of the bypass line (12) or runs directly into the apheresis column (4') or directly into the apheresis column (4") and a regeneration line (14") goes off from a liquid container (F2) or the connection line (11") and leads in the direction of flow at or preferably after the branch of the bypass line section (12') of the bypass line (12) to the plasma line (8A) or to the bypass line section (12')

of the bypass line (12) or runs directly into the apheresis column (4') or directly into the apheresis column (4").

wherein a second apheresis column (4") is connected in parallel to the first apheresis column (4') and both apheresis columns (4', 4") cannot be used simultaneously for CRP removal.

Preferably, the liquid container (F1) is a container for a physiological sodium chloride solution and the liquid container (F2) is a container for a citrate solution.

Therefore, the present invention is also directed to an apheresis device (II) according to the invention, wherein the plasma line (8A) and the bypass line section (12') of the bypass line (12) diverge from a point (P2), and the plasma line (8B) and the bypass line section (12") of the bypass line (12) plasma line (8B) converge at the point (P6), and the waste line (13') goes off from the plasma line (8B) from a point (P4) and the waste line (13") goes off from the bypass line section (12") of the bypass line (12) from a point (P8), and the at least one regeneration line (14) runs into the extracorporeal circulation system (2) at the point (P2).

A preferred embodiment of the underlying invention relates to an apheresis device (II) for extracorporeal removal and preferably for selective extracorporeal removal of CRP from blood comprising:

an extracorporeal circulation system (2) for blood,
a means (3) for generation and regulation of a flow of blood in the extracorporeal circulation system (2),
a cell separator (7) for separation of the blood into blood plasma and cellular components,
two apheresis columns (4', 4") for affinity chromatographic removal of CRP from the blood plasma,
wherein the extracorporeal circulation system (2) comprises an arterial line (5) to the cell separator (7), a plasma line (8A) from the cell separator (7) to the apheresis column (4'), a plasma line (8B) for CRP-depleted blood plasma from the apheresis column (4') to a point (P1),
a cell line (9) for the separated cellular components from the cell separator (7) to the point (P1) and a venous line (6) starting from the point (P1),
a central processing unit (10) for controlling the apheresis device (II),
a connection line (11') for connection of at least one liquid container (F) to the arterial line (5) or the cell separator (7),
characterized in that
a bypass line section (12') of the bypass line (12) branches off from the plasma line (8A) and runs into the second apheresis column (4') and the bypass line section (12") of the bypass line (12") starting from the apheresis column (4") runs into the plasma line (8B),
a waste line (13') which goes off directly from apheresis column (4') or goes off from plasma line (8B) in the direction of flow before the junction of the bypass line section (12') of the bypass line (12), a waste line (13") which goes off directly from apheresis column (14") or from the bypass line section (12") of the bypass line (12) in the direction of flow before the junction of the bypass line section (12') of the bypass line (12), wherein the plasma line (8A) and the bypass line section (12') of the bypass line (12) diverge from a point (P2), and the plasma line (8B) and the bypass line section (12") of the bypass line (12) converge at a point (P6), and
at least one regeneration line (14) which goes off from the at least one liquid container (F) or the at least one connection line (11) and leads in the direction of flow at or preferably after the branch of the bypass line section (12') of the bypass line (12) to the plasma line (8A) or to the bypass line section (12') of the bypass line (12) or runs directly into the apheresis column (4') or directly into the apheresis column (4"), and the waste line (13') goes off directly from a point (P4) from the plasma line (8B) and the waste line (13") goes off from a point (P8) from the bypass line section (12") of the bypass line (12), and the at least one regeneration line (14) runs into the extracorporeal circulation system (2) at point (P2), and wherein a second apheresis column (4") is connected in parallel to the first apheresis column (4') and both apheresis columns (4', 4") are not usable simultaneously for CRP removal, i.e. are only usable alternately.

To further reduce the dead volume of the system, it is even further preferred if not only the regeneration line (14) runs into the extracorporeal circulation system at the point (P2) where the plasma line (8A) and the bypass line section (12') of the bypass line (12) diverge, but when the drain lines (13', 13") also branch off from the same point (P6) where the plasma line (8B) and the bypass line section (12") of the bypass line (12) converge. In other words, it is preferred when the point (P6) where the plasma lines (8B) and the bypass line section (12") of the bypass line (12) converge, the point (P8) where the waste line (13") branches off and the point (P4) where waste line (13') branches off coincide, i.e., when P8=P4=P6 (see FIG. 12 and FIG. 13).

Therefore, the present invention is also directed to an apheresis device (II) according to the present invention, wherein the plasma line (8B) and the bypass line section (12") of the bypass line (12) converge at a point (P6), and the waste line (13") goes off from a point (P8) from the bypass line section (12") of the bypass line (12) and the waste line (13') goes off from a point (P4) from the plasma line (8B), and the at least one regeneration line (14) runs into the extracorporeal circulation system (2) at the point (P2), and wherein the point (P6), the point (P4) and the point (P8) are identical.

According to the present invention, an embodiment of the apheresis device (II) for extracorporeal removal of CRP from blood according to the present invention comprises two apheresis columns (4', 4") for affinity chromatographic removal of CRP from blood or blood plasma, the function of which is to bind CRP which is present in the blood or blood plasma of a patient and which is passed through the apheresis column (4') or (4").

Method

The present invention also relates to a method for regeneration of an apheresis column (4) for affinity chromatographic removal of CRP in an apheresis device (1), the method enabling regeneration during operation and being characterized by the following steps:

(A) starting redirection of the separated plasma from the plasma line (8A) into the bypass line (12), thereby stopping the introduction of the separated plasma from the plasma line (8A) into the apheresis column (4), (B) starting introduction of regeneration solution via the at least one regeneration line (14) into the plasma line (8A) or directly into the apheresis column (4), (C) starting redirection of the liquid flow exiting the apheresis column (4) from the plasma line (8B) into the waste line (13), (D) stopping the introduction of regeneration solution and stopping the redirection of the separated plasma from the plasma line (8A) into the bypass line (12), thereby introducing the separated plasma from the plasma line (8A) into the apheresis column (4), (E) closing the waste line (13) and forwarding the liquid flow exiting the apheresis column (4) into the venous line (6).

The term "stopping the introduction of the separated plasma" according to step (A) may be understood to mean, depending on the embodiment of the present invention, the use of hose clamps, control elements, valves and/or peristaltic pumps to prevent the further flow of blood plasma into the plasma line (8A) or into the bypass line section (12') of the bypass line (12) or into the apheresis column (4') or (4").

The term "stopping the introduction of regeneration solution" according to step (D) may be understood to mean, depending on the embodiment of the present invention, the use of hose clamps, control elements, valves and/or peristaltic pumps to prevent the further flow of regeneration solution into the plasma line (8A) or into the apheresis column (4). Here, it is to be understood that in embodiments where only one regeneration solution is used, the introduction of the same is stopped. In embodiments in which several regeneration solutions are successively introduced, this means that the introduction of the last regeneration solution used is stopped and thus also that the introduction of any regeneration solution is stopped.

The term "closing the waste line (13)" according to step (E) may be understood to mean, depending on the embodiment of the present invention, the use of hose clamps, control elements, valves and/or peristaltic pumps to prevent further flow of the liquid flow exiting the apheresis column (4). Here, it is to be understood that in embodiments in which only one regeneration solution is used, the introduction of the same is stopped. In embodiments in which several regeneration solutions are successively introduced, this means that the introduction of the last regeneration solution used is stopped and thus also that the introduction of any regeneration solution is stopped.

By "forwarding the liquid flow exiting the apheresis column (4)" according to step (E), the separated plasma henceforth flows back into the plasma line (8B) after passing through the apheresis column (4) and from there further through the venous line (6) back to the patient. Depending on the embodiment of the present invention, hose clamps, control elements, valves and/or peristaltic pumps may be used to change the direction of flow of the liquid flow exiting the apheresis column (4).

The present invention further relates to a method for regeneration of an apheresis column (4) for affinity chromatographic removal of CRP in an apheresis apparatus (1) as described herein, the method enabling regeneration during operation by switching from an apheresis mode to a regeneration mode, wherein in the apheresis mode, plasma separated from blood by means of the cell separator (7) is directed into the apheresis column (4) via the plasma line (8A), and the liquid flow exiting the apheresis column (4) is directed into the venous line (6) via the plasma line (8B);

and wherein the regeneration mode is characterized by the following steps:

(A) starting redirection of the separated plasma from the plasma line (8A) into the bypass line (12), thereby stopping the introduction of the separated plasma from the plasma line (8A) into the apheresis column (4), (B) starting introduction of regeneration solution via the at least one regeneration line (14) into the plasma line (8A) or directly into the apheresis column (4), (C) starting redirection of the liquid flow exiting the apheresis column (4) from the plasma line (8B) into the waste line (13), (D) stopping the introduction of regeneration solution and stopping the redirection of the separated plasma from the plasma line (8A) into the bypass line (12), thereby introducing the separated plasma from the plasma line (8A) into the apheresis column (4), (E) closing the waste line (13) and forwarding the liquid flow exiting the apheresis column (4) into the venous line (6) and thus switching again to the apheresis mode.

With regard to the two aforementioned methods, the regeneration solution is preferably a saline solution or physiological NaCl solution.

Furthermore, methods are preferred in which step (C) is initiated after a total volume X of regeneration solution(s) has been introduced into the plasma line (8A) and/or directly into the apheresis column (4), wherein X corresponds to at least 75% of the volume of the device between the point at which the regeneration line (14) runs into the extracorporeal circulation system (2) in the direction of flow at or preferably after the branch of the bypass line (12) and the point at which the waste line (13) starts from the extracorporeal circulation system (2). Here, the regeneration solution is, for example, a saline solution or a physiological saline solution.

Furthermore, methods are preferred in which step (E) is initiated after a volume Y of plasma has been introduced into the plasma line (8A) or directly into the apheresis column (4), wherein Y corresponds to at least 90% of the volume of the device between the point, at which the regeneration line (14) runs into the extracorporeal circulation system (2) in the direction of flow at or preferably after the branch of the bypass line (12) and the point at which the waste line (13) starts from the extracorporeal circulation system (2).

"During operation", as used herein, means that in order to carry out the method for regeneration of an apheresis column (4) according to the invention, the blood collection and supply as well as the operation of the cell separator do not have to be stopped. In other words, during the method for regeneration of an apheresis column (4) according to the invention, the continuously collected plasma is combined with the cell components via the bypass line (12), thereby bypassing the apheresis column (4), and is supplied to the patient. During the time in which the plasma redirection occurs via the bypass line (12), the apheresis column (4), which is usually reduced in capacity, is regenerated. Thus, the patient's circulation is not stressed because the continuously withdrawn blood is returned to the patient without delay.

"During operation" as used herein accordingly does not mean that continuous plasma collection must be interrupted in order to carry out the method of the invention for regeneration of an apheresis column (4). Furthermore, it also does not mean that CRP depletion takes place during regeneration of the apheresis column.

Thus, in both of the foregoing methods and the methods generally disclosed herein, it is preferred that the introduction of regeneration solution comprise the introduction of a single regeneration solution or the successive introduction of several regeneration solutions.

For the skilled person it is absolutely clear that an initial rinsing operation of the adsorber or of the entire system must have occurred before the execution of the method according to the invention. This is associated with a pre-filling of the entire tube system. For this, further connections may be present on the system under certain circumstances, which enable the entire system to be flushed. After the patient has been separated from the tube system, there is the possibility of preserving the adsorber so that it can be used again for further treatment on the same patient.

In other words, the present invention also relates to a method according to the invention for regeneration of an apheresis column (4) for affinity chromatographic removal of CRP in the apheresis device (1), wherein the method enables regeneration during operation and being characterized by the following steps:
- (A) redirection of the separated plasma from the plasma line (8A) into the bypass line (12),
- (B) introduction of regeneration solution from a liquid container at the connection line (11) via the regeneration line (14) into the plasma line (8A) or directly into the apheresis column (4),
- (C) redirection of the liquid flow exiting the apheresis column (4) from the plasma line (8B) into the waste line (13),
- (D) redirection of the separated plasma from the plasma line (8A) into the apheresis column (4) and stopping introduction of regeneration solution,
- (E) closing the waste line (13) and forwarding the liquid flow exiting the apheresis column (4) into the venous line (6).

The term "redirection" as used herein refers to a change in the direction of flow of the respective liquid. During the treatment mode, the separated plasma flows through the plasma line (8A) into the apheresis column (4). After leaving the apheresis column (4), the depleted plasma flows through the plasma line (8B) into the venous line (6).

By "redirection" of the flow direction of the separated plasma according to step (A), the separated plasma henceforth no longer flows through the apheresis column (4), but bypasses it by being redirected into the bypass line (12).

The term "introduction" as used herein according to step (B) may be understood to mean, depending on the embodiment of the present invention, the feeding of at least one regeneration solution (using or actuating hose clamps, control elements, valves and/or peristaltic pumps) into the plasma line (8A) or into the apheresis column (4).

By "redirection" of the flow direction of the liquid flow exiting the apheresis column (4) according to step (C), the exiting liquid henceforth no longer flows into the plasma line (8B) but directly into the waste line (13). According to the invention, it is preferred that the waste line (13) branches off directly or immediately from or after the apheresis column (4), in order to minimize the volume of regeneration solution required to regenerate the apheresis column (4). In accordance with the invention, the waste line (13) can also branch off from the plasma line (8B) and thus does not have to branch off directly from the apheresis column.

By "redirection" of the direction of flow of the separated plasma according to step (D), the separated plasma henceforth flows back through the apheresis column (4) and no longer into the bypass line (12). In certain embodiments, a pump is provided in the bypass line (12), wherein the plasma present in the bypass line (12) is pumped into the plasma line (8B) and into the patient via the venous line (6) after redirection according to step (D). Here, preferably, the plasma present in the bypass line is displaced by a NaCl solution from the regeneration line (14). Preferably, this is a 0.9% NaCl solution. It would also be conceivable that a separate liquid container can be connected to the bypass line (12), through which said NaCl solution is provided for displacement.

Therefore, a particularly preferred embodiment of the present invention relates to a method according to the invention for regeneration of an apheresis column (4) for the affinity chromatographic removal of CRP in the apheresis device (1), wherein the method enables regeneration during operation and being characterized by the steps disclosed in the following method.

Particularly preferred is therefore a method for regeneration of an apheresis column (4) for affinity chromatographic removal and preferably for selective extracorporeal removal of CRP in an apheresis device (1), wherein the method is characterized by the following steps:
- (A) starting redirection of the separated plasma from the plasma line (8A) into the bypass line (12), thereby stopping the introduction of the separated plasma from the plasma line (8A) into the apheresis column (4),
- (B) starting introduction of rinsing solution via the at least one regeneration line (14) into the plasma line (8A) or directly into the apheresis column (4),
- (C) starting the redirection of the liquid flow exiting the apheresis column (4) from the plasma line (8B) into the waste line (13),
- (D) stopping the introduction of rinsing solution and transition to the introduction of a regeneration solution via the at least one regeneration line (14) into the plasma line (8A) or directly into the apheresis column (4),
- (E) stopping the introduction of regeneration solution and transition to the introduction of a rinsing solution via the at least one regeneration line (14) into the plasma line (8A) or directly into the apheresis column (4),
- (F) stopping the introduction of rinsing solution and stopping the redirection of the separated plasma from the plasma line (8A) into the bypass line (12), thereby directing the separated plasma from the plasma line (8A) into the apheresis column (4).
- (G) closing the waste line (13) and forwarding the liquid flow exiting the apheresis column (4) into the venous line (6).

Alternatively, particularly preferred is also a method for regeneration of an apheresis column (4) for affinity chromatographic removal and preferably for selective affinity chromatographic removal of CRP in an apheresis device (1), wherein the method is characterized by the following steps:
- (A) starting redirection of the separated plasma from the plasma line (8A) into the bypass line (12), thereby stopping the introduction of the separated plasma from the plasma line (8A) into the apheresis column (4),
- (B) starting introduction of rinsing solution via the at least one regeneration line (14) into the plasma line (8A) or directly into the apheresis column (4),
- (C) stopping the introduction of rinsing solution and transition to the introduction of a regeneration solution via the at least one regeneration line (14) into the plasma line (8A) or directly into the apheresis column (4),
- (D) starting the redirection of the liquid flow exiting the apheresis column (4) from the plasma line (8B) into the waste line (13),
- (E) stopping the introduction of regeneration solution and transition to the introduction of the rinsing solution via the at least one regeneration line (14) into the plasma line (8A) or directly into the apheresis column (4),
- (F) closing the waste line (13) and forwarding the liquid flow exiting the apheresis column (4) into the venous line (6), (G) stopping the introduction of rinsing solution and stopping the redirection of the separated plasma from the plasma line (8A) into the bypass line (12), thereby directing the separated plasma from the plasma line (8A) into the apheresis column (4).

In both of the above aforementioned methods, a rinsing solution is used in addition to the regeneration solution. The rinsing solution is preferably physiologically acceptable and serves primarily to displace the blood plasma from the plasma line (8A) from point P2, from the apheresis column (4) and from the plasma line (8B) to point P4. The rinsing solution serves less or not at all for the regeneration of the apheresis column (4). The rinsing solution therefore minimizes or even completely prevents plasma loss. Only when the blood plasma has been largely to completely displaced from the section of the apheresis device (1) to be flushed with regeneration solution, the regeneration solution is introduced to regenerate the apheresis column (4). After regeneration has taken place, rinsing solution is then first led again into the section of the apheresis device (1) that has been flushed with regeneration solution (i.e. in the direction of flow from point P2 through the apheresis column (4) to point P4) until the regeneration solution has been completely disposed of through the waste line (13). Only then is the bypass line (12) closed and blood plasma again passed through the apheresis column (4). In the two aforementioned method, steps (C) and (D) can be interchanged, i.e., can be performed in any order and also simultaneously, and can also be combined in one step. However, execution of step (D) before step (C) is preferred.

In this method, the rinsing solution is preferably a physiological NaCl solution and the regeneration solution is a citrate solution.

The preferred embodiment of the method according to the invention serves to carry out the method more efficiently without loss of blood plasma. Due to the simultaneous redirection of the separated plasma and the parallel introduction of the rinsing solution into the apheresis column (4), there is no loss or no significant loss of blood plasma. Furthermore, an advantage of the preferred embodiment is that mixing of regeneration solution and blood plasma is completely avoided. This ensures that no regeneration solution enters the patient, and, on the other hand, no loss of blood plasma occurs for the patient.

This is ensured by the sequential order of steps (B) to (E). Dilution of the blood plasma takes place, if at all, only through rinsing solution. On the other hand, mixing of blood plasma with regeneration solution is completely avoided.

The volume of rinsing solution according to step (B) preferably corresponds to 3 to 4 times the volume of the matrix of the apheresis column (4).

At a minimum, the volume of rinsing solution according to step (B) corresponds to the volume of the plasma line (8A) from point P2 to the apheresis column (4) plus the volume of the matrix of the apheresis column (4) and plus the volume of the plasma line (8B) from the apheresis column (4) to point P4.

The volume of regeneration solution according to step (C) preferably corresponds to 2 to 100 times the volume of the matrix of the apheresis column (4).

The volume of rinsing solution according to step (E) preferably corresponds to 2 to 4 times the volume of the matrix of the apheresis column (4).

At least the volume of rinsing solution according to step (E) corresponds to the volume of the plasma line (8A) from point P2 to the apheresis column (4) plus the volume of the matrix of the apheresis column (4) and plus the volume of the plasma line (8B) from the apheresis column (4) to point P4.

According to this even more preferred embodiment, dilution of the plasma is largely avoided and mixing with regeneration solution is completely prevented. The user is not confronted with too much complexity regarding the use of the apheresis device (1). In an alternative embodiment, the method steps can thus also be operated manually without appearing or being too complex for the user.

The "volume of the matrix of the apheresis column" as used herein means the volume of the solid phase within the column, which in turn comprises a matrix substrate material and compounds bound thereto that have the property of specifically binding CRP. To be distinguished from this is the "dead volume of the apheresis column," i.e., the space within the column available to the mobile phase (e.g., plasma). The "dead volume of the apheresis column" is the difference between the volume enclosed by the apheresis column housing and the volume occupied by the swollen matrix (i.e. the "volume of the matrix of the apheresis column").

Another aspect of the present invention is directed to a method for regeneration of an apheresis column (4') for affinity chromatographic removal and preferably for selective affinity chromatographic removal of CRP during operation of a second apheresis column (4") in an apheresis apparatus (II) comprising the following steps:

(A) beginning with the flow of blood plasma through the apheresis column (4"), starting introduction of the separated plasma from the plasma line (8A) into the apheresis column (4') and directing the CRP-depleted blood plasma into the venous line (6), thereby stopping the introduction of the separated plasma via the bypass line section (12') of the bypass line (12) into the apheresis column (4"), (B) starting the introduction of regeneration solution via the at least one regeneration line (14) into the bypass line section (12') of the bypass line (12) or directly into the apheresis column (4"), (C) starting redirection of the liquid flow exiting the apheresis column (4") from the bypass line section (12') of the bypass line (12) into the waste line (13"), (D) starting introduction of the separated plasma via the bypass line section (12') of the bypass line (12) into the apheresis column (4") and directing the CRP-depleted blood plasma into the venous line (6), thereby stopping the introduction of the separated plasma via the plasma line (8A) into the apheresis column (4'), (E) closing the waste line (13") and starting redirection of the liquid flow exiting the apheresis column (4') from the plasma line (8B) into the waste line (13').

With regard to the two aforementioned methods, the regeneration solution is preferably a saline solution or physiological NaCl solution.

"During operation", as used in this context, means that in order to carry out the method according to the invention for regeneration of an apheresis column (4') or regeneration of an apheresis column (4"), the blood sampling and supply and the operation of the cell separator do not have to be stopped. Thus, the patient's circulation is not stressed because the continuously drawn blood is returned to the patient without delay.

In other words, in an embodiment the present invention relates to a method for regeneration of an apheresis column (4') for affinity chromatographic removal and preferably for selective affinity chromatographic removal of CRP during operation of a second apheresis column (4") in an apheresis apparatus (II), comprising the following steps:

(A) beginning with the flow of blood plasma through the apheresis column (4"), introduction of the separated plasma from the plasma line (8A) into the apheresis column (4') and directing the CRP-depleted blood plasma into the venous line (6), thereby stopping the introduction of the separated plasma via the bypass line section (12') of the bypass line (12) into the apheresis column (4"), (B) introduction of regeneration solution via the at least one regeneration line (14) into the bypass line section (12') of the bypass line (12) or directly into the apheresis column (4"), (C) redirection of the liquid flow exiting the apheresis column (4") from the bypass line section (12') of the bypass line (12) into the waste line (13"), (D) introduction of the separated plasma via the bypass line section (12') of the bypass line (12) into the apheresis column (4") and directing the CRP-depleted blood plasma into the venous line (6), thereby stopping the introduction of the separated plasma via the plasma line (8A) into the apheresis column (4'), (E) closing the waste line (13") and starting redirection of the liquid flow exiting the apheresis column (4') from the plasma line (8B) into the waste line (13').

Furthermore, the present invention relates to a method for regeneration of two apheresis columns (4',4") for affinity chromatographic removal and preferably for selective affinity chromatographic removal of CRP in an apheresis device (II), the method enabling regeneration during operation and being characterized by the following steps:

(A) beginning with the flow of blood plasma through the apheresis column (4"), starting introduction of the separated plasma from the plasma line (8A) into the apheresis column (4') and directing the CRP-depleted blood plasma into the venous line (6), thereby stopping the introduction of the separated plasma via the bypass line section (12') of the bypass line (12) into the apheresis column (4"), (B) starting the introduction of rinsing solution via the at least one regeneration line (14) into the bypass line section (12') of the bypass line (12) or directly into the apheresis column (4"), (C) starting redirection of the liquid flow exiting the apheresis column (4") from the bypass line section (12') of the bypass line (12) into the waste line (13"), (D) stopping the introduction of rinsing solution and transition to the introduction of a regeneration solution via the at least one regeneration line (14) into the bypass line section (12') of the bypass line (12) or directly into the apheresis column (4"), (E) stopping the introduction of regeneration solution and transition to the introduction of a rinsing solution via the at least one regeneration line (14) into the bypass line section (12') of the bypass line (12) or directly into the apheresis column (4"), (F) starting the introduction of rinsing solution into the plasma line (8A) via the apheresis column (4'), thereby starting introduction of the separated plasma via the bypass line section (12') of the bypass line (12) into the apheresis column (4"), (G) closing the waste line (13") and forwarding the liquid flow exiting the apheresis column (4") into the venous line (6), (H) starting redirection of the liquid flow exiting the apheresis column (4') from the plasma line (8B) into the waste line (13'), (I) stopping the introduction of rinsing solution and transition to the introduction of a regeneration solution via the at least one regeneration line (14) into the plasma line (8A) or directly into the apheresis column (4').

(J) stopping the introduction of regeneration solution and transition to the introduction of a rinsing solution via the at least one regeneration line (14) into the plasma line (8A) or directly into the apheresis column (4').

In both of the aforementioned methods, a rinsing solution is used in addition to the regeneration solution. The rinsing solution is preferably physiologically acceptable and serves primarily to displace the blood plasma from the plasma line (8A) or the bypass line section (12') of the bypass line (12) from point P2, from the apheresis column (4') or apheresis column (4") as well as from the bypass line section (12") of the bypass line (12) up to point P3 and the plasma line (8B) up to point P4. The rinsing solution serves less or not to regenerate the apheresis column (4') or the apheresis column (4"). The rinsing solution therefore minimizes or even completely prevents plasma loss. Only when the blood plasma has been largely to completely displaced from the section of the apheresis device (II) to be flushed with regeneration solution, the regeneration solution is introduced to regenerate the apheresis column (4') or the apheresis column (4"). After regeneration has taken place, rinsing solution is then first led again into the section of the apheresis device (II) that has been flushed with regeneration solution (i.e. in the direction of flow from point P2 through the apheresis column (4") to point P8) or through the apheresis column (4') to point P4) until the regeneration solution has been completely disposed of through the waste lines (13', 13").

In this method, the rinsing solution is preferably a physiological NaCl solution and the regeneration solution is a citrate solution.

The preferred embodiment of the method according to the invention serves to carry out the method more efficiently without loss of blood plasma. Due to the simultaneous redirection of the separated plasma and the parallel introduction of the rinsing solution into the apheresis column (4"), there is no loss or no significant loss of blood plasma. Furthermore, an advantage of the preferred embodiment is that mixing of regeneration solution and blood plasma is completely avoided. This ensures that no regeneration solution enters the patient and, on the other hand, no loss of blood plasma occurs for the patient.

This ensures that no regeneration solution enters the patient and, on the other hand, no loss of blood plasma occurs for the patient.

This is ensured by the sequential order of steps (B) to (E). Dilution of the blood plasma takes place, if at all, only through rinsing solution. In contrast, mixing of blood plasma with regeneration solution is completely avoided.

The volume of rinsing solution according to step (B) preferably corresponds to 3 to 4 times the volume of the matrix of the apheresis column (4"). Minimally, the volume of rinsing solution according to step (B) corresponds to the volume of the bypass line section (12') of the bypass line (12) from point P2 to the apheresis column (4") plus the volume of the matrix of the apheresis column (4") and plus the volume of the bypass line section (12') of the bypass line (12) from the apheresis column (4") to point (P3).

The volume of rinsing solution according to step (F) preferably corresponds to 3 to 4 times the volume of the matrix of the apheresis column (4'). Minimally, the volume of rinsing solution according to step (B) corresponds to the volume of the plasma line (8A') from point (P2) to the apheresis column (4') plus the volume of the matrix of the apheresis column (4') and plus the volume of the plasma line (8B) from the apheresis column to point (P4).

The volume of regeneration solution according to step (D) preferably corresponds to 2 to 100 times the volume of the matrix of the apheresis column (4").

The volume of regeneration solution according to step (I) preferably corresponds to the 2 to 100 times the volume of the matrix of the apheresis column (4').

The volume of rinsing solution according to step (E) preferably corresponds to 2 to 4 times the volume of the matrix of the apheresis column (4").

At least the volume of rinsing solution according to step (E) corresponds to the volume of the bypass line section (12') of the bypass line (12) from point P2 to the apheresis column (4") plus the volume of the matrix of the apheresis column (4") and plus the volume of the bypass line section (12') of the bypass line (12) from the apheresis column (4') to point P3.

The volume of rinsing solution according to step (J) preferably corresponds to 2 to 4 times the volume of the matrix of the apheresis column (4').

At least the volume of rinsing solution according to step (E) corresponds to the volume of the plasma line (8A) from point P2 to the apheresis column (4') plus the volume of the matrix of the apheresis column (4') and plus the volume of the plasma line (8B) from the apheresis column (4') to point P4.

Regeneration Solution

Particularly, the regeneration solution is a citrate solution, a TRIS-glycine solution, a NaCl solution, a full electrolyte solution or an EDTA solution, preferably a citrate solution, a TRIS-glycine solution or a NaCl solution, further preferably a citrate solution or a NaCl solution and most preferably a citrate solution.

The present invention therefore also relates to a method according to the invention for regeneration of an apheresis column, wherein the regeneration solution is selected from the group comprising or consisting of: NaCl solution, NaCl solution with addition of citrate, citrate solution alone, TRIS-glycine solution, and EDTA solution.

According to this embodiment, the anticoagulation solution already present in the system can be used as the regeneration solution. Consequently, regeneration can be operated without additional liquids.

The term "citrate solution" as used herein comprises aqueous solutions containing at least one citrate compound.

The term "citrate" as used herein refers to the citrate anion, i.e., the salt of citric acid, or in other words, an organic tricarboxylate of the following chemical formula:

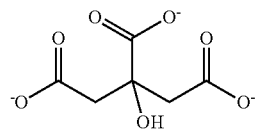

The citrate can occur in various forms (or compounds), e.g. as citric acid (in one to three times protonated form), as a salt of citric acid in combination with other (other than H+) inorganic cations (e.g. as a metal salt together with metal cations or as an ammonium salt together with ammonium ions), but also as partial citrate ester. In this context, the term "citrate compound" is also used herein.

If the salt of citric acid, i.e. the citrate anion, is complexed with an inorganic cation, the term "citrate salt" is also used herein as a special form of citrate compound. Thus, the term "citrate compound" as used herein comprises both citric acid and its salts.

According to the invention, it is preferred if the citrate solution contains at least one of the citrate compounds selected from the group comprising or consisting of citric acid, sodium dihydrogen citrate, disodium hydrogen citrate, trisodium citrate, trisodium citrate dihydrate, potassium dihydrogen citrate, dipotassium hydrogen citrate, tripotassium citrate, lithium dihydrogen citrate, dilithium hydrogen citrate, trilithium citrate, ammonium dihydrogen citrate, diammonium hydrogen citrate, triammonium citrate, tricalcium dicitrate (calcium citrate), trimagnesium dicitrate (magnesium citrate) and/or partial citrate esters.

Where the rather general term "sodium citrate" is used in this application, this term comprises the various protonated forms of sodium citrate, i.e. both the unprotonated (trisodium citrate) and the singly protonated (disodium hydrogen citrate) or doubly protonated form (sodium dihydrogen citrate). Where the rather general term "potassium citrate" is used in this application, this term comprises the various protonated forms of potassium citrate, i.e., both the unprotonated (tripotassium citrate) and the singly protonated (dipotassium hydrogen citrate) or the doubly protonated form (potassium dihydrogen citrate). Where the rather general term "lithium citrate" is used in this application, this term comprises the various protonated forms of lithium citrate, i.e., both the unprotonated (trilithium citrate) and the singly protonated (dilithium hydrogen citrate) or the doubly protonated form (lithium dihydrogen citrate). Where the rather general term "ammonium citrate" is used in this application, this term comprises the various protonated forms of ammonium citrate, i.e. both the unprotonated (triammonium citrate) and the singly protonated (diammonium hydrogen citrate) or the doubly protonated form (ammonium dihydrogen citrate).

A citrate solution consisting of citric acid, trisodium citrate, D-glucose and water is also referred to as "acid citrate dextrose solution (ACD solution)". Preferred variants of the citrate solution used according to the invention relate to ACD solutions containing between 22.9 mM and 38.0 mM citric acid, between 44.9 mM and 74.8 mM trisodium citrate, between 74.2 mM and 123.6 mM D-glucose and water. A particularly preferred variant of the citrate solution used according to the invention relates to an ACD solution containing 38 mM citric acid, 74.8 mM trisodium citrate, 123.6 mM D glucose and water. This is also referred to as "ACD-A solution."

A citrate solution consisting of citric acid, trisodium citrate, sodium hydrogen phosphate, D-glucose and water is also referred to as a "citrate-phosphate-dextrose solution (CPD)". A preferred variant of the citrate solution used according to the invention relates to a CPD solution containing 15.6 mM citric acid, 89.4 mM trisodium citrate, 128.7 mM D glucose, 16.1 mM sodium hydrogen phosphate and water. A citrate solution consisting of citric acid, trisodium citrate, sodium hydrogen phosphate, D-glucose, adenine and water is also referred to as "citrate phosphate dextrose solution with adenine (CPDA)". A preferred variant of the citrate solution used according to the invention relates to a CPDA solution containing 15.6 mM citric acid, 89.4 mM trisodium citrate, between 128.7 mM and 160.9 mM D glucose, 16.1 mM sodium hydrogen phosphate, 2 mM adenine and water. A preferred variant of the citrate solution used according to the invention relates to a CPDA solution containing 15.6 mM citric acid, 89.4 mM trisodium citrate, between 128.7 mM D glucose, 16.1 mM sodium hydrogen phosphate, 2 mM adenine and water. A particularly preferred variant of the citrate solution used according to the invention relates to a CPDA solution containing 15.6 mM citric acid, 89.4 mM trisodium citrate, 160.9 mM D glucose, 16.1 mM sodium hydrogen phosphate, 2 mM adenine and water.

The term "NaCl solution" as used herein comprises aqueous solutions containing sodium chloride (i.e., NaCl, also referred to as table salt) as a main ingredient. "Main ingredient" as used herein means that the molar concentration of sodium chloride in the NaCl solution is greater than the respective molar concentration of all other compounds within the NaCl solution excluding water. Preferably, the NaCl solution comprises 0.1 to 5 wt. % sodium chloride, particularly preferably 0.9 wt. %. Preferably, the rinsing solution is such a NaCl solution.

The term "TRIS-glycine solution" as used herein comprises aqueous solutions containing tris(hydroxymethyl) aminomethane (2-amino-2-(hydroxymethyl) propane-1,3-diol; TRIS) and glycine. Preferably, a "TRIS-glycine solution" is a TRIS-glycine buffer. Particularly preferably, the tri-glycine solution is a TRIS-glycine buffer with a pH of 8.3 of TRIS (25 mM) and glycine (192 mM). Further preferably, the tri-glycine solution is a TRIS-glycine buffer with a pH of 8.3 from TRIS (25 mM), glycine (192 mM) and SDS (sodium lauryl sulfate) (0.1% m/V). Preferably, the pH value corresponds to the pH value at 25° C.

In a preferred specific embodiment, the rinsing solution is a saline solution or a physiological saline solution or a PBS solution (phosphate buffered saline) or a combination of saline solution and PBS solution successively or simultaneously, and the regeneration solution is a citrate solution.

Thus, a preferred specific embodiment relates to a method for regeneration of an apheresis column (4) for affinity chromatographic removal and preferably for selective affinity chromatographic removal of CRP in an apheresis device (1), the method being characterized by the following steps:
(A) starting redirection of the separated plasma from the plasma line (8A) into the bypass line (12), thereby stopping the introduction of the separated plasma from the plasma line (8A) into the apheresis column (4),
(B) starting introduction of a saline solution via the at least one regeneration line (14) into the plasma line (8A) or directly into the apheresis column (4),
(C) starting redirection of the liquid flow exiting the apheresis column (4) from the plasma line (8B) into the waste line (13),
(D) stopping the introduction of the saline solution and transition to the introduction of a citrate solution via the at least one regeneration line (14) into the plasma line (8A) or directly into the apheresis column (4),
(E) stopping the introduction of citrate solution and stopping the redirection of the separated plasma from the plasma line (8A) into the bypass line (12), thereby introducing the separated plasma from the plasma line (8A) into the apheresis column (4),
(F) closing the waste line (13) and forwarding the liquid flow exiting the apheresis column (4) into the venous line (6).

Alternatively, the preferred specific embodiment relates to a method for regeneration of an apheresis column (4) for affinity chromatographic removal and preferably for selective affinity chromatographic removal of CRP in an apheresis device (1), the method being characterized by the following steps:
(A) starting redirection of the separated plasma from the plasma line (8A) into the bypass line (12), thereby stopping the introduction of the separated plasma from the plasma line (8A) into the apheresis column (4),
(B) starting introduction of a saline solution via the at least one regeneration line (14) into the plasma line (8A) or directly into the apheresis column (4),
(C) stopping the introduction of saline solution and transition to the introduction of a citrate solution via the at least one regeneration line (14) into the plasma line (8A) or directly into the apheresis column (4),
(D) starting redirection of the liquid flow exiting the apheresis column (4) from the plasma line (8B) into the waste line (13),
(E) stopping the introduction of citrate solution and transition to the introduction of a saline solution via the at least one regeneration line (14) into the plasma line (8A) or directly into the apheresis column (4),
(F) closing the waste line (13) and forwarding the liquid flow exiting the apheresis column (4) into the venous line (6);
(G) stopping the introduction of saline solution and stopping the redirection of the separated plasma from the plasma line (8A) into the bypass line (12), thereby introducing the separated plasma from the plasma line (8A) into the apheresis column (4).

In the two aforementioned methods, steps (C) and (D) are interchangeable, i.e., they can be performed in any order and also simultaneously and can also be combined in one step.

Preferably, the regeneration methods according to the invention are carried out in such a way that first the plasma is displaced from the apheresis column (4) with a rinsing solution, such as a saline solution or physiological saline solution, and is fed back into the patient to the point that almost only saline solution is fed back. Only then the saline is introduced into the waste line (13) and regeneration solution, such as a citrate solution, is introduced into the plasma line (8A) in the direction of flow at or preferably after the bypass line (12), which displaces the saline, regenerates the apheresis column (4), is completely introduced into the waste line (13) and discarded. After the apheresis column (4) has been regenerated with several apheresis column volumes of regeneration solution, a rinsing solution, such as a saline solution or physiological saline solution, is again introduced until the regeneration solution is completely displaced from the apheresis device (1) and is discarded. Only then, the waste line (13) is closed, the rinsing solution returned to the patient, the bypass line (12) closed, and plasma reintroduced through the plasma line (8A) into the apheresis column (4) simultaneously or immediately one after the other, wherein the order of the steps can be interchanged.

A further preferred specific embodiment relates to a method for regeneration of an apheresis column (4) for affinity chromatographic removal and preferably for selective affinity chromatographic removal of CRP in an apheresis device (1), the method being characterized by the following steps:
(A) starting redirection of the separated plasma from the plasma line (8A) into the bypass line (12), thereby stopping the introduction of the separated plasma from the plasma line (8A) into the apheresis column (4), (B) starting introduction of a saline solution via the at least one regeneration line (14) into the plasma line (8A) or directly into the apheresis column (4),
(C) starting redirection of the liquid flow exiting the apheresis column (4) from the plasma line (8B) into the waste line (13),
(D) stopping the introduction of saline solution and transition to the introduction of a citrate solution via the at least one regeneration line (14) into the plasma line (8A) or directly into the apheresis column (4),
(E1) stopping the introduction of citrate solution and transition to the introduction of a saline solution via the at least one regeneration line (14) into the plasma line (8A) or directly into the apheresis column (4),
(E2) stopping the introduction of saline solution and transition to the introduction of a PBS solution via the at least one regeneration line (14) into the plasma line (8A) or directly into the apheresis column (4),
(E3) stopping the introduction of PBS solution and transition to the introduction of a saline solution via the at least one regeneration line (14) into the plasma line (8A) or directly into the apheresis column (4),
(F) stopping the introduction of saline solution and stopping the redirection of the separated plasma from the plasma line (8A) into the bypass line (12), thereby introducing the separated plasma from the plasma line (8A) into the apheresis column (4);
(G) closing the waste line (13) and forwarding the liquid flow exiting the apheresis column (4) into the venous line (6).

An alternative preferred specific embodiment relates to a method for regeneration of an apheresis column (4) for affinity chromatographic removal and preferably for selective affinity chromatographic removal of CRP in an apheresis device (1), the method being characterized by the following steps:
(A) starting redirection of the separated plasma from the plasma line (8A) into the bypass line (12), thereby stopping the introduction of the separated plasma from the plasma line (8A) into the apheresis column (4),
(B) starting introduction of a saline solution via the at least one regeneration line (14) into the plasma line (8A) or directly into the apheresis column (4),
(C) stopping the introduction of saline solution and transition to the introduction of a citrate solution via the at least one regeneration line (14) into the plasma line (8A) or directly into the apheresis column (4),
(D) starting redirection of the liquid flow exiting the apheresis column (4) from the plasma line (8B) into the waste line (13),
(E1) stopping the introduction of citrate solution and transition to the introduction of a saline solution via the at least one regeneration line (14) into the plasma line (8A) or directly into the apheresis column (4),
(E2) stopping the introduction of saline solution and transition to the introduction of a PBS solution via the at least one regeneration line (14) into the plasma line (8A) or directly into the apheresis column (4),
(E3) stopping the introduction of PBS solution and transition to the introduction of a saline solution via the at least one regeneration line (14) into the plasma line (8A) or directly into the apheresis column (4),
(F) closing the waste line (13) and forwarding the liquid flow exiting the apheresis column (4) into the venous line (6);
(G) stopping the introduction of saline solution and stopping the redirection of the separated plasma from the plasma line (8A) into the bypass line (12), thereby introducing the separated plasma from the plasma line (8A) into the apheresis column (4).

In the two aforementioned methods, steps (C) and (D) are interchangeable, i.e. can be performed in any order and also simultaneously, and can also be combined in one step.

Thus, the present invention relates to a method for regeneration of two apheresis columns (4',4") for affinity chromatographic removal and preferably for selective affinity chromatographic removal of CRP in an apheresis device (II), the method enabling regeneration during operation and being characterized by the following steps:
(A) beginning with the flow of blood plasma through the apheresis column (4"), starting introduction of the separated plasma from the plasma line (8A) into the apheresis column (4') and directing the CRP-depleted blood plasma into the venous line (6), thereby stopping the introduction of the separated plasma via the bypass line section (12') of the bypass line (12) into the apheresis column (4"),
(B) starting the introduction of saline solution via the at least one regeneration line (14) into the bypass line section (12') of the bypass line (12) or directly into the apheresis column (4"),
(C) starting redirection of the liquid flow exiting the apheresis column (4") from the bypass line section (12') of the bypass line (12) into the waste line (13"),
(D) stopping the introduction of saline solution and transition to the introduction of a citrate solution via the at least one regeneration line (14) into the bypass line section (12') of the bypass line (12) or directly into the apheresis column (4"),
(E) stopping the introduction of citrate solution and transition to the introduction of a saline solution via the at least one regeneration line (14) into the bypass line section (12') of the bypass line (12) or directly into the apheresis column (4"),
(F) starting the introduction of saline solution into the plasma line (8A) via the apheresis column (4'), and thereby introduction of the separated plasma via the bypass line section (12') of the bypass line (12) into the apheresis column (4")
(G) closing the waste line (13") and forwarding of the liquid flow exiting the apheresis column (4") into the venous line (6),
(H) starting redirection of the liquid flow exiting the apheresis column (4') from the plasma line (8B) into the waste line (13').
(I) stopping the introduction of rinsing solution and transition to the introduction of a citrate solution via the at least one regeneration line (13) into the plasma line (8A) or directly into the apheresis column (4'),
(J) stopping the introduction of citrate solution and transition to the introduction of a saline solution via the at least one regeneration line (13) into the plasma line (8A) or directly into the apheresis column (4').

Preferably, the regeneration methods according to the invention are carried out such that the plasma is first displaced from the apheresis column (4") with a rinsing solution, such as a saline solution or physiological saline solution, and fed back into the patient up to the point that almost only saline solution is fed back. Only then, the saline solution is introduced into the waste line (13") and regeneration solution, such as a citrate solution, is introduced into the bypass section (12') of the bypass line (12) in the direction of flow at point P2, which displaces the saline solution, regenerates the apheresis column (4"), is completely introduced into the waste line (13″) and discarded. After the apheresis column (4″) has been regenerated with several apheresis column volumes of regeneration solution, a rinsing solution, such as a saline solution or physiological saline solution, is again introduced until the regeneration solution is completely displaced from the apheresis device (II) and discarded. Only then, the plasma line (8A) is closed, the rinsing solution led back to the patient, and plasma reintroduced through the bypass line section (12′) of the bypass line (12) into the apheresis column (4″) simultaneously or directly one after the other.

Another preferred specific embodiment relates to a method for regeneration of two apheresis columns (4′,4″) for affinity chromatographic removal and preferably for selective affinity chromatographic removal of CRP in an apheresis device (II), the method enabling regeneration during operation and being characterized by the following steps:

(A) beginning with the flow of blood plasma through the apheresis column (4″), starting introduction of the separated plasma from the plasma line (8A) into the apheresis column (4′) and directing the CRP-depleted blood plasma into the venous line (6), thereby stopping the introduction of the separated plasma via the bypass line section (12′) of the bypass line (12) into the apheresis column (4″), (B) starting the introduction of saline solution via the at least one regeneration line (14) into the bypass line section (12′) of the bypass line (12) or directly into the apheresis column (4″), (C) starting redirection of the liquid flow exiting the apheresis column (4″) from the bypass line section (12′) of the bypass line (12) into the waste line (13″), (D) stopping the introduction of saline solution and transition to the introduction of a citrate solution via the at least one regeneration line (14) into the bypass line section (12′) of the bypass line (12) or directly into the apheresis column (4″), (E1) stopping the introduction of citrate solution and transition to the introduction of a saline solution via the at least one regeneration line (14) into the bypass line section (12′) of the bypass line (12) or directly into the apheresis column (4″), (E2) stopping the introduction of saline solution and transition to the introduction of a PBS solution via the at least one regeneration line (14) into the bypass line section (12′) of the bypass line (12) or directly into the apheresis column (4″), (E3) stopping the introduction of PBS solution and transition to the introduction of a saline solution via the at least one regeneration line (14) into the bypass line section (12′) of the bypass line (12) or directly into the apheresis column (4″), (F) starting the introduction of saline solution into the plasma line (8A) via the apheresis column (4′), and thereby introduction of the separated plasma via the bypass line section (12′) of the bypass line (12) into the apheresis column (4″)

(G) closing the waste line (13″) and forwarding of the liquid flow exiting the apheresis column (4″) into the venous line (6), (H) starting redirection of the liquid flow exiting the apheresis column (4′) from the plasma line (8B) into the waste line (13′), (I) stopping the introduction of rinsing solution and transition to the introduction of a citrate solution via the at least one regeneration line (14) into the plasma line (8A) or directly into the apheresis column (4′), (J) stopping the introduction of citrate solution and transition to the introduction of a saline solution via the at least one regeneration line (14) into the plasma line (8A) or directly into the apheresis column (4′).

EXAMPLES

Application Example

The term "matrix volume" (also abbreviated as MV), as used herein, refers to the volume of the matrix contained within the adsorber.

The term "adsorber volume" (also abbreviated as AV), as used herein, refers to the volume of the adsorber housing.

Example 1: Apheresis with a Bypass Line and an Apheresis Column

Preparation:

A suitable tubing system is inserted into the apheresis device (1) for extracorporeal removal of CRP from blood of a patient as shown in FIG. 3, with a plasma centrifuge as cell separator (7). A 5 L bag of 0.9% NaCl solution and a 500 ml bag of ACD-A solution are connected to the connection line. Two 3 L waste bags are connected to the waste line (13) (e.g. via a 3-way valve).

The arterial (5) and venous (6) lines are connected to each other with an adapter. The plasma lines (8A and 8B) before and after the adsorber are also connected with an adapter (without adsorber in between) to form a closed system.

The entire system is filled with NaCl solution by pre-rinsing with 1 L of 0.9% NaCl solution (200 ml/min); the air present is displaced into the first waste bag. A shaken CRP adsorber (MV 20 ml, AV 30 ml) is then inserted into the plasma line (8A and 8B) instead of the adapter. The adsorber is pre-rinsed with 1 L NaCl solution (100 ml/min). The NaCl is also directed into the first waste bag.

As the last step of preparation, the plasma centrifuge is pre-filled with 0.9% NaCl solution and 1:15 diluted ACD-A solution. The required volume is composed of the volume of the tubing system in the plasma centrifuge (7), the connection line (11) up to the plasma centrifuge and the plasma line between the plasma centrifuge and P2. The displaced NaCl is directed into the first waste bag via P4/P6.

Apheresis:

1. After completed preparation, it is switched to the second waste bag. The patient is connected to the arterial (5) and venous (6) lines. At the start of apheresis, the blood is directed into the centrifuge (60-80 ml/min). Throughout the treatment, ACD-A is mixed into the blood at a ratio of 1:15 (1 ml ACD-A to 15 ml blood) via the connection line (11).

The NaCl thereby displaced is directed to the second waste bag via P2, the bypass line (12) and P4/P6. When plasma separation begins, after a volume corresponding to the tubing from the plasma centrifuge to point P4/6, the system switches so that the plasma flows into the venous line (6), and thus back to the patient. After a constant plasma flow of approx. 30 ml/min has been achieved for 3 minutes, the first cycle can begin.

2. The bypass line (12) is closed and the plasma is passed over the adsorber (loading). Thereby, the NaCl present in the plasma line (8A and 8B) and the adsorber is passed via P4/P6 into the second waste bag up to a volume consisting of the volume of the plasma line (8A and 8B) plus the AV. The adsorber is then loaded with 50-100 MV (1000 to 2000 ml) of plasma. Regeneration then begins.

3. For this, the plasma is returned to the patient via the bypass line (12).

The adsorber is now rinsed with 0.9% NaCl (30 ml/min) via the regeneration line (14) and the plasma line (8A and 8B). The volume required for this is calculated from the AV and the volume of the plasma line (8A and 8B). The plasma in the plasma line (8A and 8B) and the adsorber is also returned to the patient up to a volume consisting of the AV and 75% of the volume of the plasma line (8A and 8B). Subsequently, P4/P6 is switched to direct the solutions into the second waste bag.

In the next step it is regenerated with 3 MV (60 ml) of 0.9% NaCl followed by 1:15 ACD-A solution (100 ml/min). Afterwards, it is rinsed with 0.9% NaCl (100 ml/min). The volume required for this is calculated from the AV, the volume of the regeneration line (14) and the plasma line (8A and 8B).

Then step 2 (loading) can be performed again, followed by step 3. If necessary, the bag with ACD-A solution must be replaced.

4. After the last loading, a final regeneration is performed. At the same time, the arterial line (5) is closed. Using 0.9% NaCl (30 ml/min), the blood from the plasma centrifuge (7) is displaced via the cell line (9) as well as the remaining plasma from the plasma line to P2 and the bypass line (12) and led back to the patient via the connection line (11). The volume required for this is composed of the volume of the plasma centrifuge (7), the volume of the plasma line up to P2, bypass line (12), the cell line (9) and the arterial line (6). The patient can then be separated from the apheresis device.

5. If desired, the NaCl bag can now be replaced by a bag with preservation solution (e.g. PBS with sodium azide). The adsorber is rinsed with 10 MV preservation solution via the regeneration line (into the second waste bag). The adsorber is then removed, sealed and stored. The tubing system is removed from the apheresis device and is disposed.

Example 2: Alternating Use of the Apheresis Column Connected in Parallel

Preparation:

A suitable tubing system is inserted into the apheresis device (II) for extracorporeal removal of CRP from blood of a patient as shown in FIG. 13, with a plasma centrifuge as cell separator (7). A 5 L bag of 0.9% NaCl solution and a 500 ml bag of ACD-A solution are connected to the connection line. Two 3 L waste bags are connected to the waste line (13) (e.g. via a 3-way valve).

The arterial (5) and venous (6) lines are connected to each other with an adapter. Similarly, the plasma lines (8A and 8B) before and after the adsorber are connected with an adapter (without adsorber in between) and the bypass line sections (12' and 12") of the bypass line (12) before and after the adsorber are connected with an adapter (without adsorber in between) to form a closed system.

The entire system is filled with NaCl solution by pre-rinsing with 1 L 0.9% NaCl solution (200 ml/min); the air present is displaced into the first waste bag. A shaken CRP adsorber (MV 20 ml, AV 30 ml) is then inserted into the bypass line sections (12' and 12") and into the plasma line (8A and 8B) instead of the adapter. The adsorber is pre-rinsed with 1 L NaCl solution (100 ml/min). The NaCl is also directed into the first waste bag.

As the last step of the preparation, the plasma centrifuge is pre-filled with 0.9% NaCl solution and 1:15 diluted ACD-A solution. The required volume is composed of the volume of the tubing system in the plasma centrifuge (7), the connection line (11) up to the plasma centrifuge and the plasma line between the plasma centrifuge and P2. The displaced sodium chloride is directed into the first waste bag via P8/P4/P6.

Apheresis:

1. After completed preparation, it is switched over to the second waste bag. The patient is connected to the arterial (5) and venous (6) lines. At the start of apheresis, the blood is directed into the centrifuge (60-80 ml/min). Throughout the treatment, ACD-A is mixed into the blood at a ratio of 1:15 (1 ml ACD-A to 15 ml blood) via the connection line (11). The NaCl thereby displaced is directed to the second waste bag via P2, the bypass line section 12' and P8/P4/P6. When plasma separation begins, after a volume equal to the tubing from the plasma centrifuge to the P8/P4/P6 point, the system switches so that the plasma flows back into the venous line (6), and thus to the patient. After a constant plasma flow of approx. 30 ml/min has been achieved for 3 minutes, the first cycle can begin.

2. The plasma line (8A) in the region between the nodal point (P2) and the adsorber (4') is closed and the plasma is passed over the adsorber (4") (loading). Thereby, the NaCl present in the bypass line sections (12' and 12") and the adsorber (4") is directed into the second waste bag via P3/P4/P6 up to a volume consisting of the volume of the bypass line sections (12' and 12") plus the AV. The adsorber (4") is then loaded with 50-100 MV (1000 to 2000 ml) of plasma. The blood plasma is then displaced from the adsorber (4") with the sodium chloride solution.

3. It is switched over to the second adsorber and the bypass line section (12') is closed into the region between the nodal point (P2) and the adsorber (4"). The plasma is directed over the adsorber (4') (loading). In this process, the sodium chloride solution present in the bypass line sections (12' and 12") and the adsorber (4') is passed into the second waste bag via P8/P4/P6 up to a volume consisting of the volume of the plasma line (8A and 8B) plus the AV. The adsorber (4') is then loaded with 50-100 MV (1000 to 2000 ml) of plasma. The blood plasma is then displaced from the adsorber (4') with the sodium chloride solution and fed to the patient.

Step 2 (loading) can then be performed again, followed by step 3. If necessary, the bag with ACD-A solution must be replaced.

4. After the last loading, a final regeneration is performed. At the same time, the arterial line (5) is closed. Using 0.9% NaCl (30 ml/min), the blood is displaced from the plasma centrifuge (7) via the cell line (9) and led back to the patient via the connection line (11). The volume required for this is composed of the volume of the plasma centrifuge (7) and the volume of the cell line (9) and the arterial line (6). The patient can then be separated from the apheresis device.

5. If desired, the sodium chloride solution bag can now be replaced by a bag with preservation solution (e.g. PBS with Na-azide). The adsorber is rinsed with 10 MV preservation solution via the regeneration line (into the second waste bag). The adsorber is then removed, sealed and stored. The tubing system is removed from the apheresis device and is disposed.

Example 3: Alternating Use of Apheresis Columns Connected in Parallel (4', 4") and Regeneration During Operation Preparation:

A suitable tubing system is inserted into the apheresis device (II) for extracorporeal removal of CRP from blood of a patient as shown in FIG. 5, with a plasma centrifuge as cell separator (7). A 5 L bag of 0.9% NaCl solution and a 500 ml bag of ACD-A solution are connected to the connection line. Two 3 L waste bags are connected to the waste line (13) (e.g. via a 3-way valve).

The arterial (5) and venous (6) lines are connected with an adapter. Similarly, the bypass line sections (12' and 12") before and after the adsorber are connected with an adapter (without adsorber in between) and the plasma lines (8A and 8B) before and after the adsorber are connected with an adapter (without adsorber in between) to form a closed system.

The entire system is filled with NaCl solution by pre-rinsing with 1 L of 0.9% NaCl solution (200 ml/min); the air present is displaced into the first waste bag. A shaken CRP adsorber (MV 20 ml, AV 30 ml) is then inserted into the bypass line sections (12' and 12") and into the plasma line (8A and 8B) instead of the adapter. The adsorber is pre-rinsed with 1 L NaCl solution (100 ml/min). The NaCl is also directed into the first waste bag.

As the last step of the preparation, the plasma centrifuge is pre-filled with 0.9% NaCl solution and 1:15 diluted ACD-A solution. The required volume is composed of the volume of the tubing system in the plasma centrifuge (7), the connection line (11) up to the plasma centrifuge and the plasma line between the plasma centrifuge and P2. The displaced sodium chloride is directed into the first waste bag via P8/P4/P6.

Apheresis:

1. After completed preparation, it is switched to the second waste bag. The patient is connected to the arterial (5) and venous (6) lines. At the start of apheresis, the blood is directed into the centrifuge (60-80 ml/min). Throughout the treatment, ACD-A is mixed into the blood at a ratio of 1:15 (1 ml ACD-A to 15 ml blood) via the connection line (11). The NaCl thereby displaced is directed to the second waste bag via P2, the bypass line section (12') and P8/P4/P6. When plasma separation begins, after a volume equal to the tubing from the plasma centrifuge to the P8/P4/6 point, it is switched so that plasma flows into the venous line (6), and thus back to the patient. After a constant plasma flow of approx. 30 ml/min has been achieved for 3 minutes, the first cycle can begin.
2. The plasma line (8A) is closed and the plasma is directed over the adsorber (4") (loading). Thereby, the NaCl present in the bypass line sections (12' and 12") and the adsorber (4") is directed into the second waste bag via P8/P4/P6 up to a volume consisting of the volume of the bypass line sections (12' and 12") plus the AV. The adsorber is then loaded with 50-100 MV (1000 to 2000 ml) of plasma. The blood plasma is then displaced from the adsorber (4") with the sodium chloride solution.
3. It is switched over to the second adsorber and the bypass line section (12') is closed in the region between the nodal point (P2) and the adsorber (4"). The plasma is directed over the adsorber (4') (loading). In this process, the sodium chloride solution present in the bypass line sections (12' and 12") and the adsorber (4") is directed into the second waste bag via P8/P4/P6 up to a volume consisting of the volume of the plasma line (8A and 8B) plus the AV. The adsorber (4') is then loaded with 50-100 MV (1000 to 2000 ml) of plasma. The blood plasma is then displaced from the adsorber (4') with the sodium chloride solution and fed to the patient.

At the same time, the adsorber (4") is rinsed (30 ml/min) with 0.9% NaCl via the regeneration line (14) and the bypass line sections (12' and 12"). The volume required for this is calculated from the AV and the volume of the bypass line sections (12' and 12"). The plasma present in the bypass line sections (12' and 12") and the adsorber (4") is also redirected to the patient up to a volume consisting of the AV and 75% of the volume of the plasma line (8A and 8B). Subsequently, P4/P6 is switched to direct the solutions into the second waste bag.

In the next step, it is regenerated with 3 MV (60 ml) 0.9% NaCl and then with 1:15 ACD-A solution (100 ml/min). Afterwards, it is rinsed with 0.9% NaCl (100 ml/min). The volume required for this is calculated from the AV, the volume of the regeneration line (14) and the plasma line (8A and 8B).

Step 2 (loading) can then be carried out again, followed by step 3. If necessary, the bag with ACD-A solution must be replaced.
4. After the last loading, a final regeneration is performed. At the same time, the arterial line (5) is closed. Using 0.9% NaCl (30 ml/min), the blood is displaced from the plasma centrifuge (7) via the cell line (9) and led back to the patient via the connection line (11). The volume required for this is composed of the volume of the plasma centrifuge (7) and the volume of the cell line (9) and the arterial line (6). The patient can then be separated from the apheresis device.
5. If desired, the sodium chloride solution bag can now be replaced by a bag with preservation solution (e.g. PBS with sodium azide). The adsorber is rinsed with 10 MV preservation solution via the regeneration line (into the second waste bag). The adsorber is then removed, sealed and stored. The tubing system is removed from the apheresis device and disposed of.

DESCRIPTION OF THE FIGURES

FIG. 11: Schematic illustration of an embodiment of the apheresis device according to the invention for extracorporeal removal of CRP from blood. The arterial line (5), in which there is a means (3) for generation and regulation of a flow of blood (e.g. peristaltic pump), leads the blood of a patient to the cell separator (7, e.g. a centrifugal cell separator). From this, the plasma line (8A) leads to the apheresis column (4') for affinity chromatographic removal of CRP. The bypass line section (12') of the bypass line (12) branches off from the plasma line (8A), leads to the apheresis column (4") for affinity chromatographic removal of CRP from blood. From the apheresis column (4"), the bypass line section (12") of the bypass line (12) for CRP-depleted blood plasma leads to the nodal point (P1), and from the apheresis column (4'), the plasma line (8B) for CRP-depleted blood plasma leads to the nodal point (P1). Another line, the cell line (9), leads from the cell separator (7) to the nodal point (P1). The venous line (6), which leads the treated blood back to the patient, also goes off from the nodal point (P1). In addition, there is a connection line (11) for connection of a liquid container (F1), which runs into the arterial line (5) or alternatively leads directly into the cell separator (7) (dashed line). The bypass line section (12') of the bypass line (12) and the plasma line (8A) diverge at the nodal point (P2) and at the nodal point (P6) the bypass line section (12") of the bypass line (12) and the plasma line (8B) converge. The waste line (13") branches off from the bypass line section (12") of the bypass line (12) at the nodal point (P8), and the waste line (13') branches off from the plasma line (8B) at the nodal point (P4). In addition, the regeneration line (14) for connection of a liquid container (F2) leads to the nodal point (P7). Two lines (15', 15") branch off at the nodal point (P7). The line (15') runs into the extracorporeal circulation system (2) at the nodal point (P2) and the line (15") runs into the region between the nodal point (P2) and the apheresis column (4"). For improved clarity, the central processing unit (10), which is also part of the apheresis apparatus according to the invention, is not shown.

FIG. 12: Schematic illustration of an embodiment of the apheresis device according to the invention for extracorporeal removal of CRP from blood. The arterial line (5), in which there is a means (3) for generation and regulation of a flow of blood (e.g. peristaltic pump), leads the blood of a patient to the cell separator (7, e.g. a centrifugal cell separator). From this, the plasma line (8A) leads to the apheresis column (4') for affinity chromatographic removal of CRP. The bypass line section (12') of the bypass line (12) branches off from the plasma line (8A), leads to the apheresis column (4") for affinity chromatographic removal of CRP from blood. From the apheresis column (4"), the bypass line section (12") of the bypass line (12) for CRP-depleted blood plasma leads to the nodal point (P1), and from the apheresis column (4'), the plasma line (8B) for CRP-depleted blood plasma leads to the nodal point (P1). Another line, the cell line (9), leads from the cell separator (7) to the nodal point (P1). The venous line (6), which leads the treated blood back to the patient, also goes off from the nodal point (P1). In addition, there is a connection line (11) for connection of a liquid container (F1), which runs into the arterial line (5) or alternatively leads directly into the cell separator (7) (dashed line). The bypass line section (12') of the bypass line (12) and the plasma line (8A") diverge at the nodal point (P2) and at the nodal point (P6) the bypass line section (12") of the bypass line (12) and the plasma line (8B") converge. The waste line (13) branches off from the extracorporeal circulation system (2) at the nodal point (P6). In addition, the regeneration line (14) for connection of a liquid container (F2) runs into the extracorporeal circulation system (2) at the nodal point (P2). For improved clarity, the central processing unit (10), which is also part of the apheresis apparatus according to the invention, is not shown.

LIST OF REFERENCES

Figure 1:
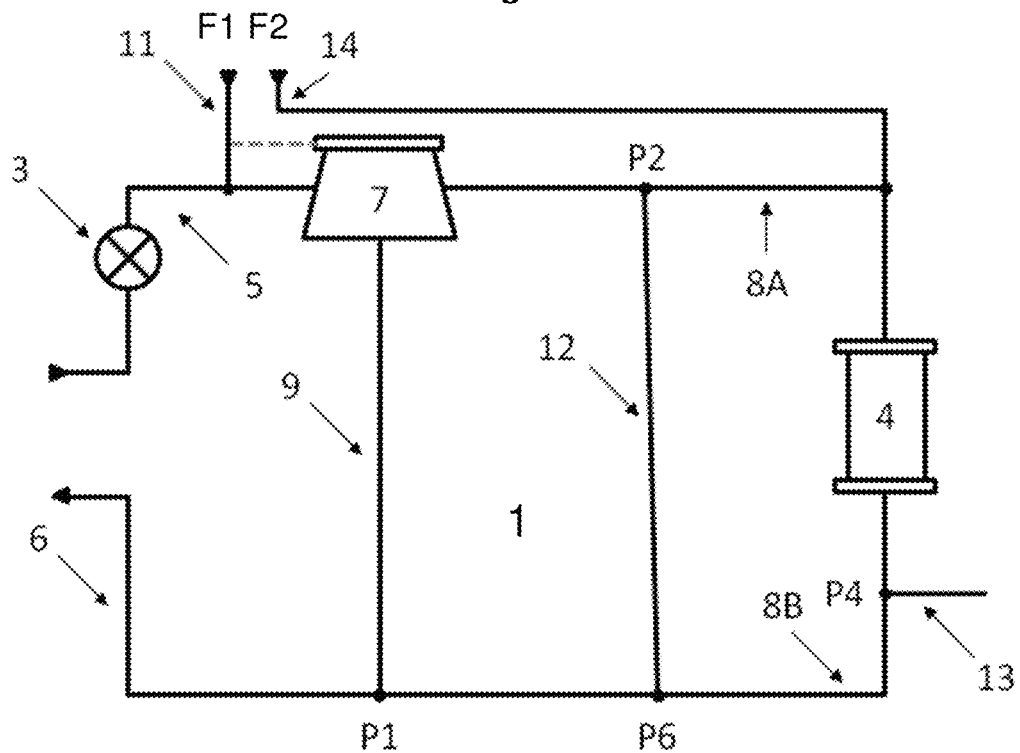
FIG. 1: Schematic illustration of an embodiment of the apheresis device (1) according to the invention for extracorporeal removal of CRP from blood. The arterial line (5), in which there is a means (3) for generation and regulation of a flow of blood (e.g. a peristaltic pump), leads the blood of a patient to the cell separator (7, e.g. a centrifugal cell separator). From this, the plasma line (8A) leads to the apheresis column (4) for affinity chromatographic removal of CRP from the blood. From this, the plasma line (8B) leads to the nodal point (P1). Another line, the cell line (9), leads from the cell separator (7) to the nodal point (P1). The venous line (6), which leads the treated blood back to the patient, also goes off from the nodal point (P1). In addition, there is a connection line (11) for connection of a liquid container (F1), which runs into the arterial line (5) or alternatively runs directly into the cell separator (7) (dashed line). The bypass line (12) branches off from the plasma line (8A) at the nodal point (P2) and runs into the plasma line (8B) at the nodal point (P6). The waste line (13) branches off from the plasma line (8B) at the nodal point (P4). In addition, the regeneration line (14) for connection of a liquid container (F2) runs into the plasma line (8A) in a region between the nodal point (P2) and the apheresis column (4). Alternatively, the regeneration line (14) can also lead directly into the apheresis column (4) (not shown). For improved clarity, the central processing unit (10), which is also part of the apheresis device according to the invention, is not shown.
Figure 2:
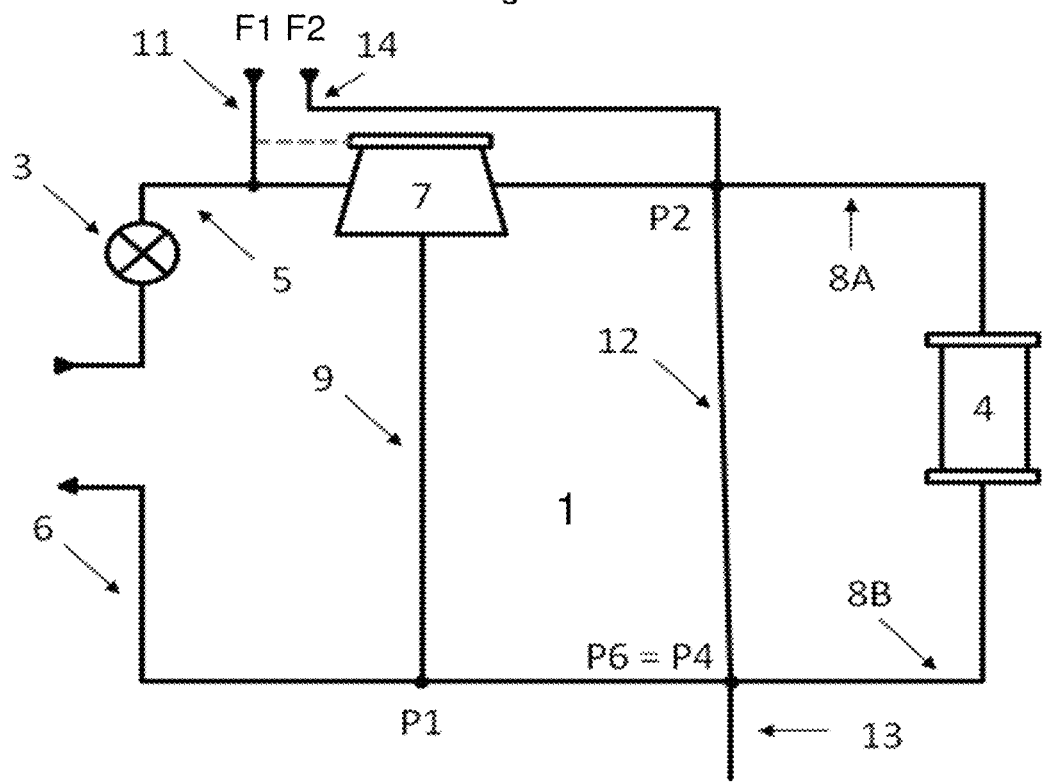
FIG. 2: Schematic illustration of an embodiment of the apheresis device according to the invention for extracorporeal removal of CRP from blood. The arterial line (5), in which there is a means (3) for generation and regulation of a flow of the blood (e.g. a peristaltic pump), leads the blood of a patient to the cell separator (7, e.g. a centrifugal cell separator). From this, the plasma line (8A) leads to the apheresis column (4) for affinity chromatographic removal of CRP from the blood. From this, the plasma line (8B) leads to the nodal point (P1). Another line, the cell line (9), leads from the cell separator (7) to the nodal point (P1). The venous line (6), which leads the treated blood back to the patient, also goes off from the nodal point (P1). In addition, there is a connection line (11) that runs into the arterial line (5) or alternatively runs directly into the cell separator (7) (dashed line). The bypass line (12) branches off from the plasma line (8A) at the nodal point (P2) and runs into the plasma line (8B) at the nodal point (P6). The waste line (13) branches off from the plasma line (8B) at the nodal point (P6). In addition, the regeneration line (14) runs into the plasma line (8A) at the nodal point (P2). For improved clarity, the central processing unit (10), which is also part of the apheresis device according to the invention, is not shown.
Figure 3:
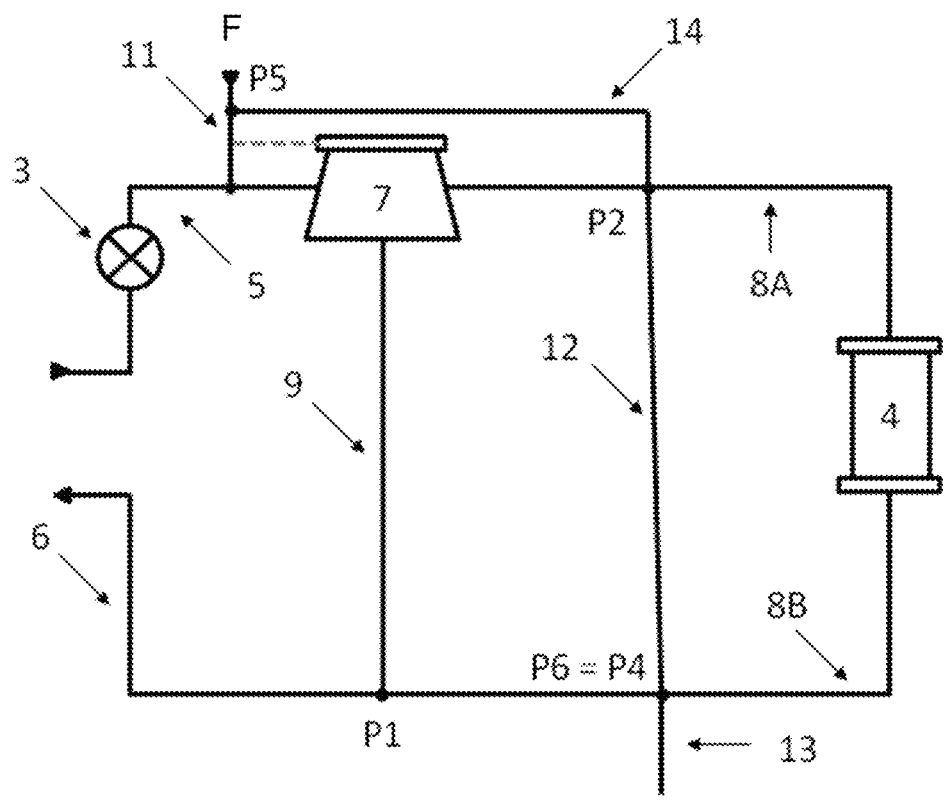
FIG. 3: Schematic illustration of an embodiment of the apheresis device according to the invention for extracorporeal removal of CRP from blood. The arterial line (5), in which there is a means (3) for generation and regulation of a flow of the blood (e.g. a peristaltic pump), leads the blood of a patient to the cell separator (7, e.g. a centrifugal cell separator). From this, the plasma line (8A) leads to the apheresis column (4) for affinity chromatographic removal of CRP from the blood. From this, the plasma line (8B) leads to the nodal point (P1). Another line, the cell line (9), leads from the cell separator (7) to the nodal point (P1). The venous line (6), which leads the treated blood back to the patient, also goes off from the nodal point (P1). In addition, there is a connection line (11) for connection of a liquid container (F), which runs into the arterial line (5) or alternatively runs directly into the cell separator (7) (dashed line). The bypass line (12) branches off from the plasma line (8A) at the nodal point (P2) and runs into the plasma line (8B) at the nodal point (P6). The waste line (13) branches off from the plasma line (8B) at the nodal point (P6). In addition, the regeneration line (14), which branches off from the connection line (11) at the point (P5), runs into the plasma line (8A) at the nodal point (P2). For improved clarity, the central processing unit (10), which is also part of the apheresis device according to the invention, is not shown.
Figure 4:
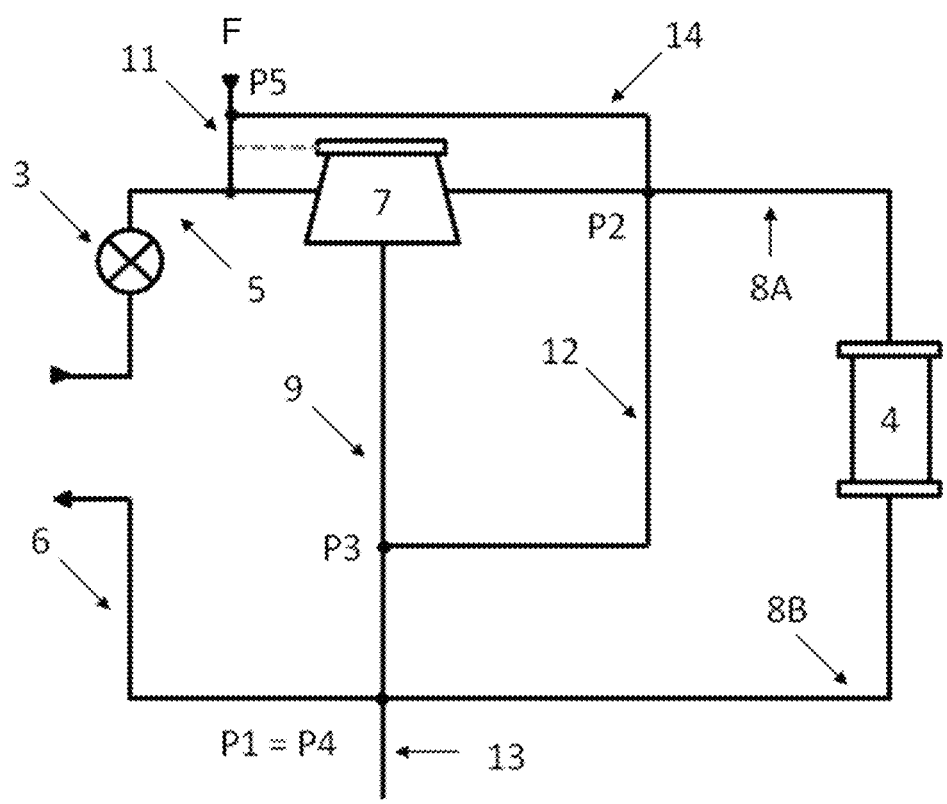
FIG. 4: Schematic illustration of an embodiment of the apheresis device according to the invention for extracorporeal removal of CRP from blood. The arterial line (5), in which there is a means (3) for generation and regulation of a flow of the blood (e.g. a peristaltic pump), leads the blood of a patient to the cell separator (7, e.g. a centrifugal cell separator). From this, the plasma line (8A) leads to the apheresis column (4) for affinity chromatographic removal of CRP from the blood. From this, the plasma line (8B) leads to the nodal point (P1). Another line, the cell line (9), leads from the cell separator (7) to the nodal point (P1). The venous line (6), which leads the treated blood back to the patient, also goes off from the nodal point (P1). In addition, there is a connection line (11) which runs into the arterial line (5) or alternatively leads directly into the cell separator (7) (dashed line). The bypass line (12) branches off from the plasma line (8A) at the nodal point (P2) and runs into the cell line (9) at the nodal point (P3). The waste line (13) branches off from the plasma line (8B) at the nodal point (P1). In addition, the regeneration line (14), which branches off from the connection line (11) at the point (P5), runs into the plasma line (8A) at the nodal point (P2). For improved clarity, the central processing unit (10), which is also part of the apheresis device according to the invention, is not shown.
Figure 5:
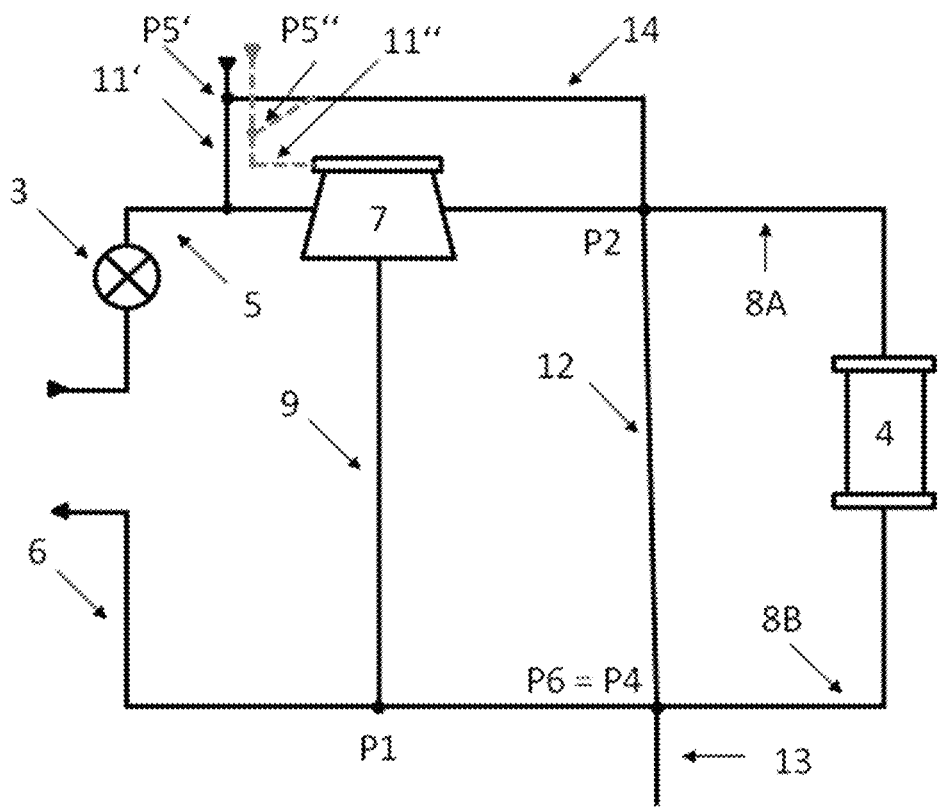
FIG. 5: Schematic illustration of an embodiment of the apheresis device according to the invention for extracorporeal removal of CRP from blood. The arterial line (5), in which there is a means (3) for generation and regulation of a flow of the blood (e.g. a peristaltic pump), leads the blood of a patient to the cell separator (7, e.g. a centrifugal cell separator). From this, the plasma line (8A) leads to the apheresis column (4) for affinity chromatographic removal of CRP from the blood. From this, the plasma line (8B) leads to the nodal point (P1). Another line, the cell line (9), leads from the cell separator (7) to the nodal point (P1). The venous line (6), which leads the treated blood back to the patient, also goes off from the nodal point (P1). In addition, there is a connection line (11') which runs into the arterial line (5) but could also have run directly into the cell separator (7), as well as a connection line (11") which runs into the cell separator (7) but could also have run into the arterial line (5). The bypass line (12) branches off from the plasma line (8A) at the nodal point (P2) and runs into the plasma line (8B) at the nodal point (P6). The waste line (13) branches off from the plasma line (8B) at the nodal point (P6). In addition, the regeneration line (14), which is in communication with the connection line (11') at the point (P5') and is in communication with the connection line (11") at the point (P5'), runs into the plasma line (8A) at the nodal point (P2). For improved clarity, the central processing unit (10), which is also part of the apheresis device according to the invention, is not shown.
Figure 6:
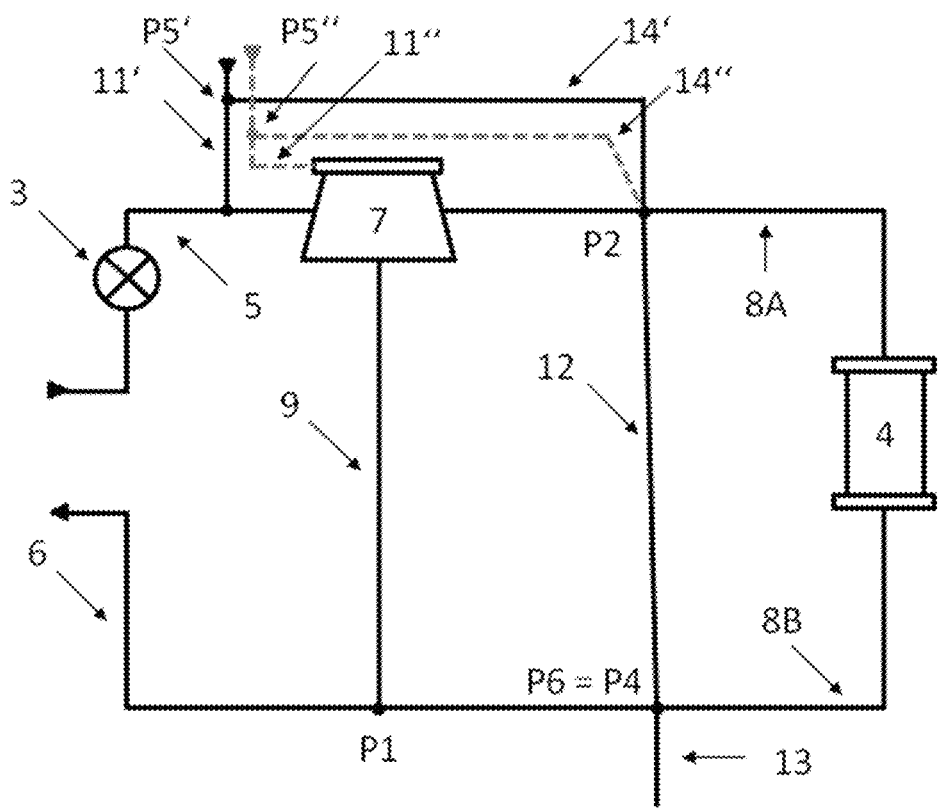
FIG. 6: Schematic illustration of an embodiment of the apheresis device according to the invention for extracorporeal removal of CRP from blood. The arterial line (5), in which there is a means (3) for generation and regulation of a flow of the blood (e.g. a peristaltic pump), leads the blood of a patient to the cell separator (7, e.g. a centrifugal cell separator). From this, the plasma line (8A) leads to the apheresis column (4) for affinity chromatographic removal of CRP from the blood. From this, the plasma line (8B) leads to the nodal point (P1). Another line, the cell line (9), leads from the cell separator (7) to the nodal point (P1). The venous line (6), which leads the treated blood back to the patient, also goes off from the nodal point (P1). In addition, there is a connection line (11') which runs into the arterial line (5) but could also have run directly into the cell separator (7), as well as a connection line (11") which runs into the cell separator (7) but could also have run into the arterial line (5). The bypass line (12) branches off from the plasma line (8A) at the nodal point (P2) and runs into the plasma line (8B) at the nodal point (P6). The waste line (13) branches off from the plasma line (8B) at the nodal point (P6). In addition, a first regeneration line (14'), which branches off from the connection line (11') at the point (P5'), and a second regeneration line (14"), which branches off from the connection line (11") at the point (P5"), both run into the plasma line (8A) at the nodal point (P2). For improved clarity, the central processing unit (10), which is also part of the apheresis device according to the invention, is not shown.
Figure 7:
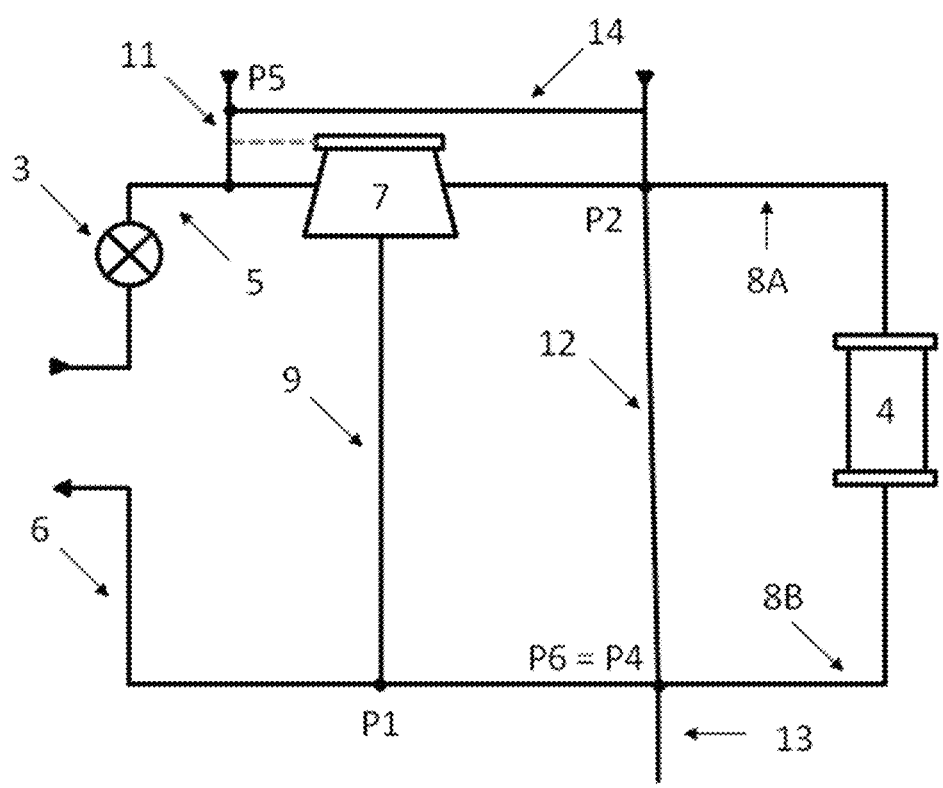
FIG. 7: Schematic illustration of an embodiment of the apheresis device according to the invention for extracorporeal removal of CRP from blood as described in FIG. 3, with the difference that there is an additional connection for a liquid container from the regeneration line (14). The connection line (11) runs into the arterial line (5) and could, however, also lead directly into the cell separator (7), which is indicated by the dashed line. This time, the regeneration line (14) has an additional connection for a liquid container, wherein this connection is located after the cell separator (7) in the direction of flow, so that liquid from this additional liquid container cannot be fed into the cell separator (7) and cannot be fed into the arterial line (5) before the cell separator (7), but only into the plasma line (8A) in the direction of flow after the cell separator (7) or directly into the apheresis column (4).
Figure 8:
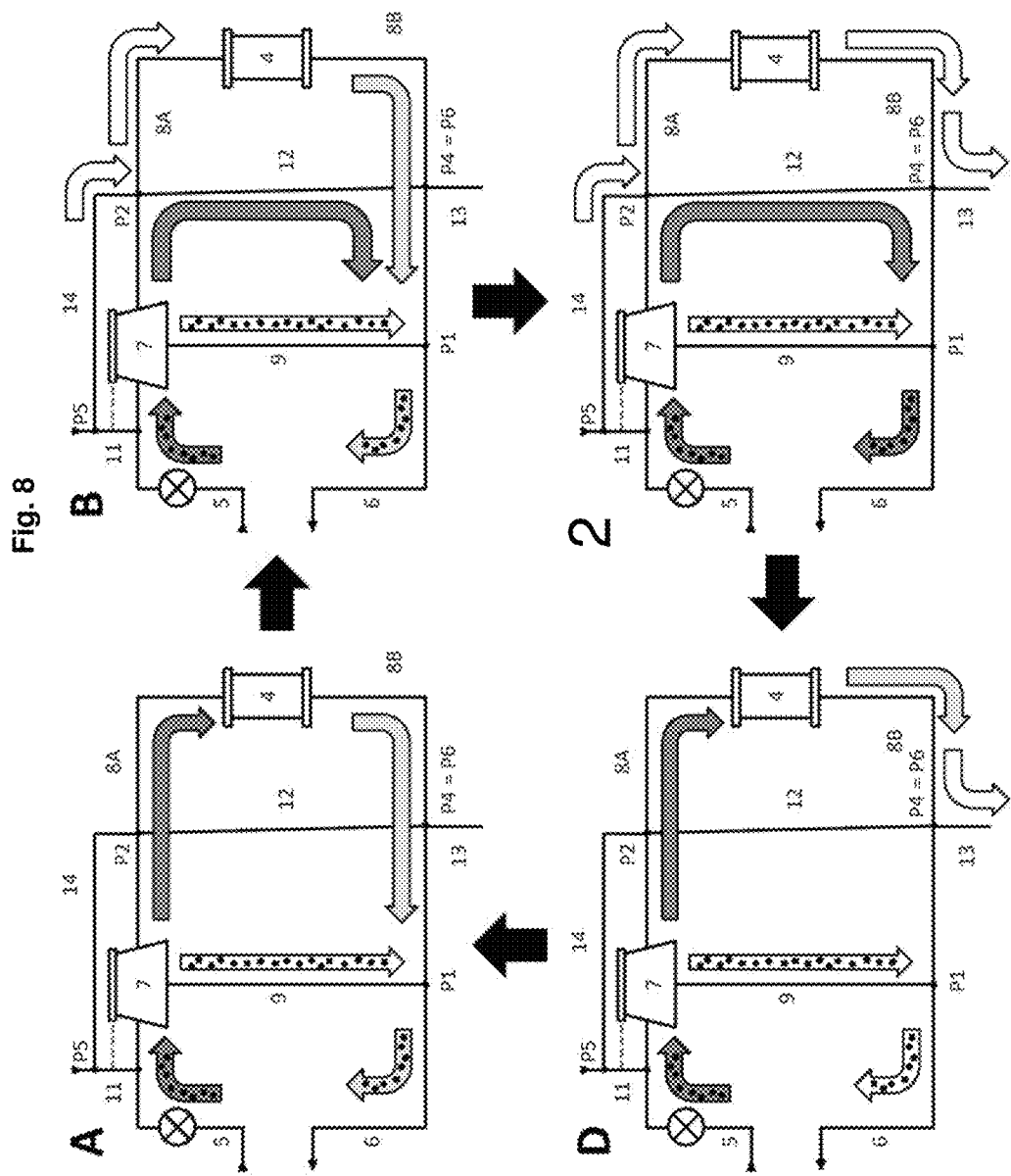
FIG. 8: Schematic illustration of a regeneration method according to the invention.
(A) In normal operation, the untreated blood (dark gray & dotted arrow) from the patient is separated into the untreated plasma (dark gray arrow) and the cellular components (white & dotted arrow) in the cell separator (7). The untreated plasma is directed into the apheresis column (4) via the plasma line (8A) and CRP is depleted there. The plasma treated in this way (light gray arrow) is passed via the plasma line (8B) to point (P1), where it is combined with the cellular components. The treated blood (light gray & dotted arrow) is led back to the patient via the venous line.
(B) By switching the valve at point (P2), the untreated plasma is redirected into the bypass line (12) and regeneration solution (white arrow) is introduced into the apheresis column. The majority of the thereby displaced plasma is returned to the patient.
(C) After flowing through the apheresis column (4), the regeneration solution is redirected into the waste line (13) by switching the valve at point (P6) and thus is discarded.
(D) Subsequently, the introduction of regeneration solution is stopped by switching the valve at point (P2) and the untreated plasma is reintroduced into the apheresis column (4). Most of the thereby displaced regeneration solution is discarded via the waste line (13). Subsequent valve switching at point (P6) switches back to normal operation (A).
Figure 9:
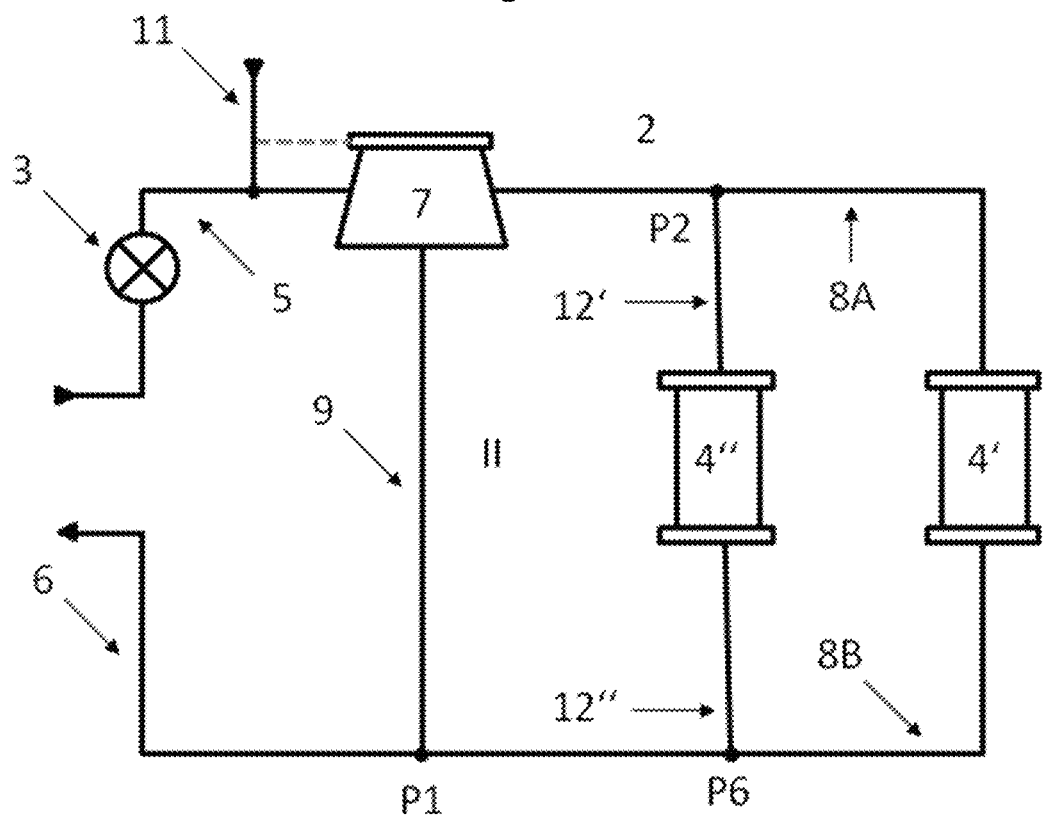
FIG. 9: Schematic illustration of an embodiment of the apheresis device (II) according to the invention for extracorporeal removal of CRP from blood. The arterial line (5), in which there is a means (3) for generation and regulation of a flow of blood (e.g. peristaltic pump), leads the blood of a patient to the cell separator (7, e.g. a centrifugal cell separator). From this, the plasma line (8A) leads to the apheresis column (4') for affinity chromatographic removal of CRP. The bypass line section (12') of the bypass line (12) branches off from the plasma line (8A), leads to the apheresis column (4") for affinity chromatographic removal of CRP from blood. From the apheresis column (4"), the bypass line section (12") of the bypass line (12) for CRP-depleted blood plasma leads to the nodal point (P1), and from the apheresis column (4'), the plasma line (8B) for CRP-depleted blood plasma leads to the nodal point (P1). Another line, the cell line (9), leads from the cell separator (7) to the nodal point (P1). The venous line (6), which leads the treated blood back to the patient, also goes off from the nodal point (P1). In addition, there is a connection line (11) for connection of a liquid container (F1), which runs into the arterial line (5) or alternatively leads directly into the cell separator (7) (dashed line). The plasma line (8A) and the bypass line section (12') of the bypass line (12) diverge at the nodal point (P2) and at the nodal point (P6) the bypass line section (12") of the bypass line (12) and the plasma line (8B) converge. For improved clarity, the central processing unit (10), which is also part of the apheresis apparatus according to the invention, is not shown.
Figure 10:
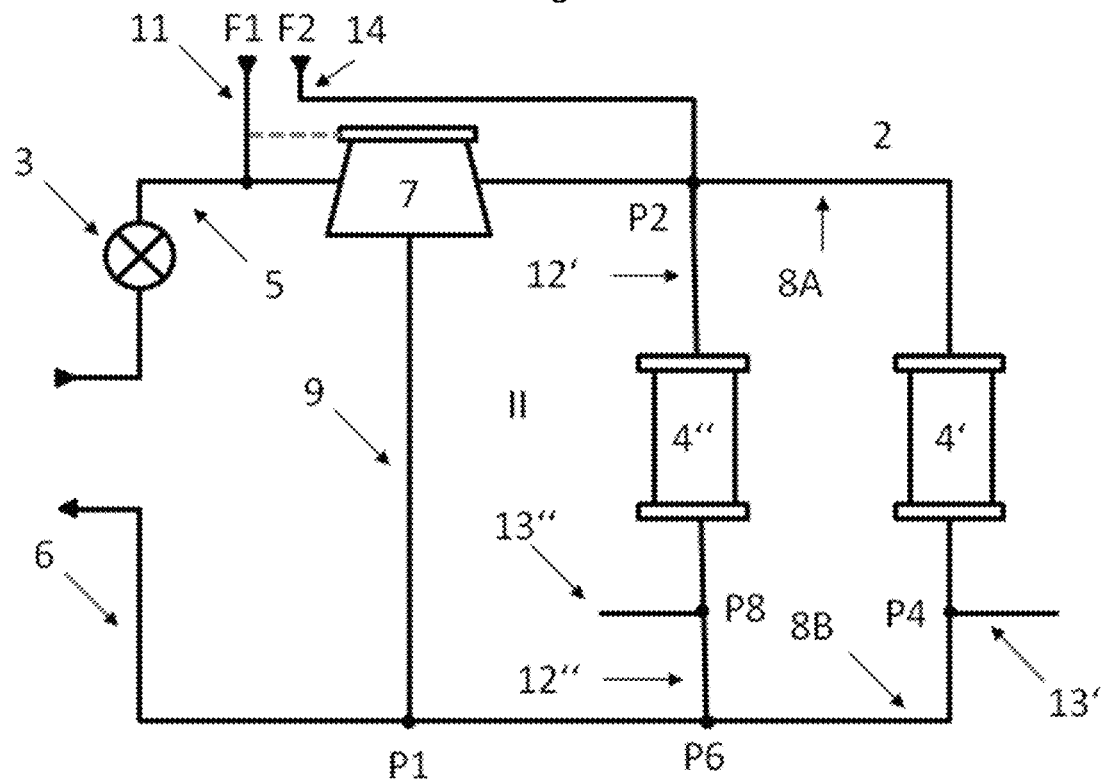
FIG. 10: Schematic illustration of an embodiment of the apheresis device according to the invention for extracorporeal removal of CRP from blood. The arterial line (5), in which there is a means (3) for generation and regulation of a flow of blood (e.g. peristaltic pump), leads the blood of a patient to the cell separator (7, e.g. a centrifugal cell separator). From this, the plasma line (8A) leads to the apheresis column (4') for affinity chromatographic removal of CRP. The bypass line section (12') of the bypass line (12) branches off from the plasma line (8A), leads to the apheresis column (4") for affinity chromatographic removal of CRP from blood. From the apheresis column (4"), the bypass line section (12") of the bypass line (12) for CRP-depleted blood plasma leads to the nodal point (P1), and from the apheresis column (4'), the plasma line (8B) for CRP-depleted blood plasma leads to the nodal point (P1). Another line, the cell line (9), leads from the cell separator (7) to the nodal point (P1). The venous line (6), which leads the treated blood back to the patient, also goes off from the nodal point (P1). In addition, there is a connection line (11) for connection of a liquid container (F1), which runs into the arterial line (5) or alternatively leads directly into the cell separator (7) (dashed line). The bypass line section (12') of the bypass line (12) and the plasma line (8A) diverge at the nodal point (P2) and at the nodal point (P6) the bypass line section (12") of the bypass line (12) and the plasma line (8B) converge. The waste line (13") branches off from the bypass line section (12') of the bypass line (12) at the nodal point (P8), and the waste line (13') branches off from the plasma line (8B) at the nodal point (P4). In addition, the regeneration line (14) for connection of a liquid container (F2) runs into the extracorporeal circulation system (2) at the nodal point (P2). For improved clarity, the central processing unit (10), which is also part of the apheresis apparatus according to the invention, is not shown.
Figure 13:
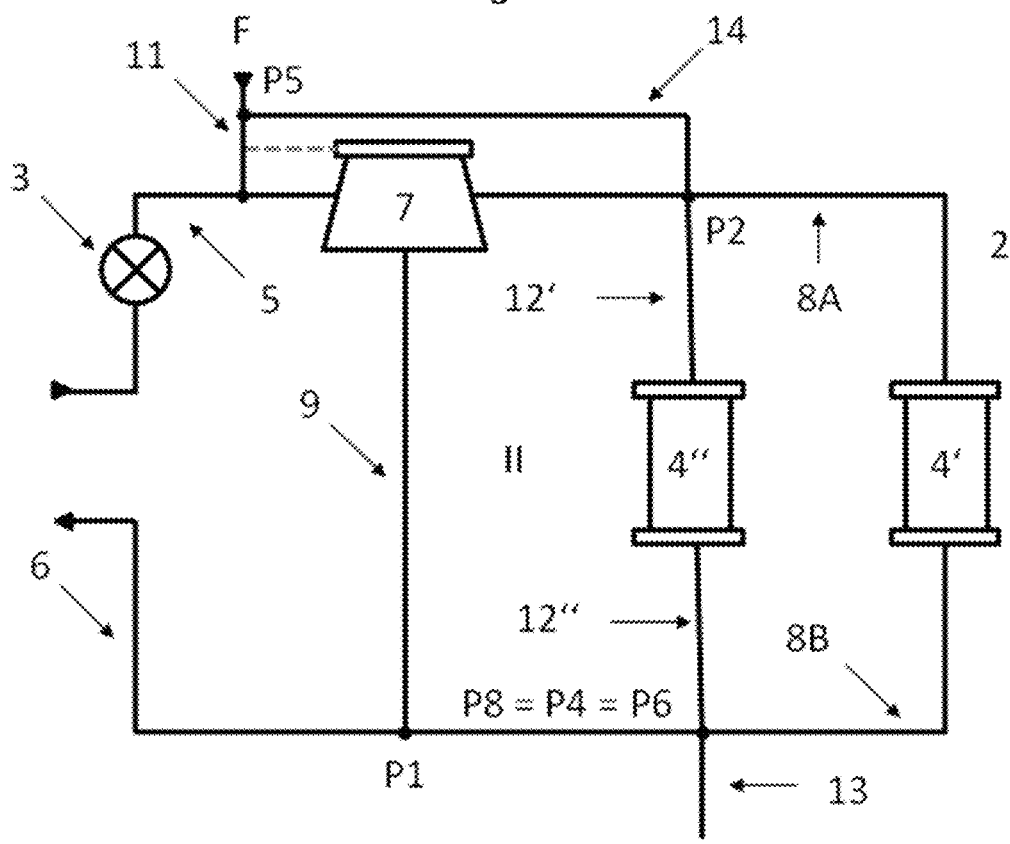
FIG. 13: Schematic illustration of an embodiment of the apheresis device according to the invention for extracorporeal removal of CRP from blood. The arterial line (5), in which there is a means (3) for generating and regulating a flow of blood (e.g. peristaltic pump), leads the blood of a patient to the cell separator (7, e.g. a centrifugal cell separator). From this, the plasma line (8A) leads to the apheresis column (4') for affinity chromatographic removal of CRP. The bypass line section (12') of the bypass line (12) branches off from the plasma line (8A), leads to the apheresis column (4") for affinity chromatographic removal of CRP from blood. From the apheresis column (4"), the bypass line section (12') of the bypass line (12) for CRP-depleted blood plasma leads to the nodal point (P1), and from the apheresis column (4'), the plasma line (8B) for CRP-depleted blood plasma leads to the nodal point (P1). Another line, the cell line (9), leads from the cell separator (7) to the nodal point (P1). The venous line (6), which leads the treated blood back to the patient, also goes off from the nodal point (P1). In addition, there is a connection line (11) for connection of a liquid container (F), which runs into the arterial line (5) or alternatively leads directly into the cell separator (7) (dashed line). The bypass line section (12') of the bypass line (12) and the plasma line (8A) diverge at the nodal point (P2) and at the nodal point (P6) the bypass line section (12") of the bypass line (12) and the plasma line (8B) converge. The waste line (13) branches off from the extracorporeal circulation system (2) at the nodal point (P6). In addition, the regeneration line (14), which branches off from the connection line (11) at the point (P5), runs into the extracorporeal circulation system (2) at the nodal point (P2). For improved clarity, the central processing unit (10), which is also part of the apheresis apparatus according to the invention, is not shown.
Figure 14:
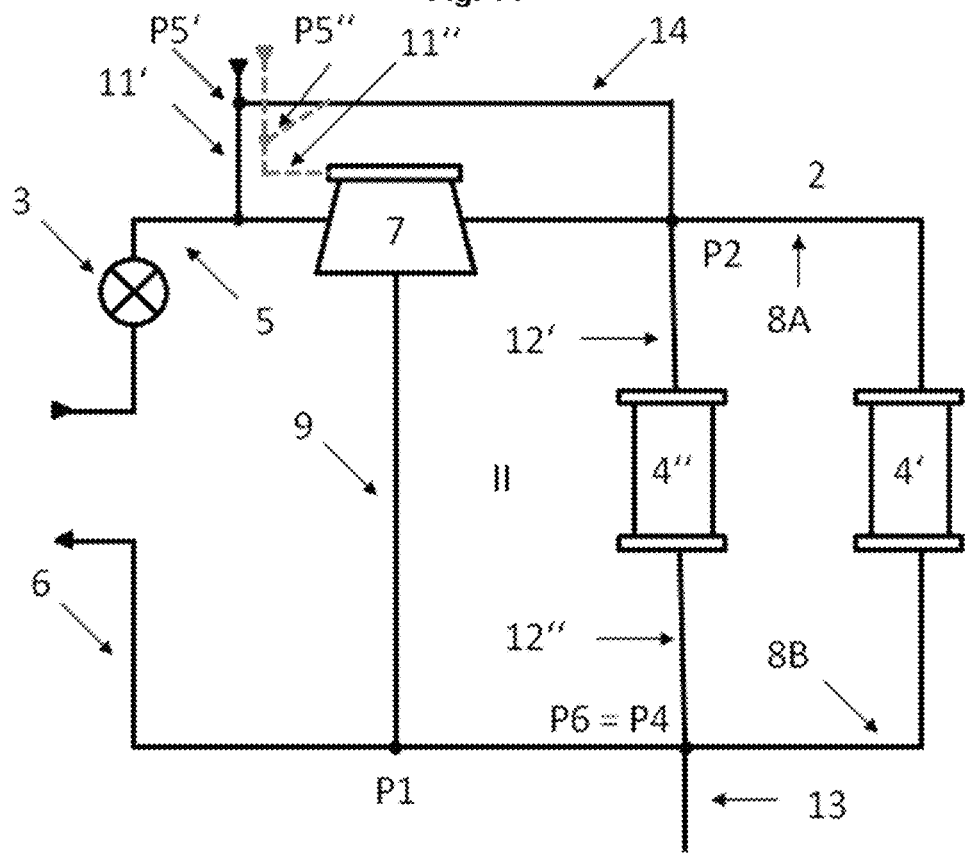
FIG. 14: Schematic illustration of an embodiment of the apheresis device according to the invention for extracorporeal removal of CRP from blood. The arterial line (5), in which there is a means (3) for generating and regulating a flow of blood (e.g. peristaltic pump), leads the blood of a patient to the cell separator (7, e.g. a centrifugal cell separator). From this, the plasma line (8A) leads to the apheresis column (4') for affinity chromatographic removal of CRP. The bypass line section (12') of the bypass line (12) branches off from the plasma line (8A), leads to the apheresis column (4") for affinity chromatographic removal of CRP from blood. From the apheresis column (4"), the bypass line section (12") of the bypass line (12) for CRP-depleted blood plasma leads to the nodal point (P1), and from the apheresis column (4'), the plasma line (8B) for CRP-depleted blood plasma leads to the nodal point (P1). Another line, the cell line (9), leads from the cell separator (7) to the nodal point (P1). The venous line (6), which leads the treated blood back to the patient, also goes off from the nodal point (P1). In addition, there is a connection line (11') that runs into the arterial line (5) but could also have run directly into the cell separator (7), as well as a connection line (11") that runs into the cell separator (7) but could also have run into the arterial line (5). The bypass line section (12') of the bypass line (12) and the plasma line (8A) diverge at the nodal point (P2) and at the nodal point (P6) the bypass line section (12") of the bypass line (12) and the plasma line (8B) converge. The waste line (13) branches off from the extracorporeal circulation system (2) at the nodal point (P6). In addition, the regeneration line (14), which is in communication with the connection line (11') at the point (P5') and is in communication with the connection line (11") at the point (P5'), runs into the extracorporeal circulation system (2) at the nodal point (P2). For improved clarity, the central processing unit (10), which is also part of the apheresis apparatus according to the invention, is not shown.
Figure 15:
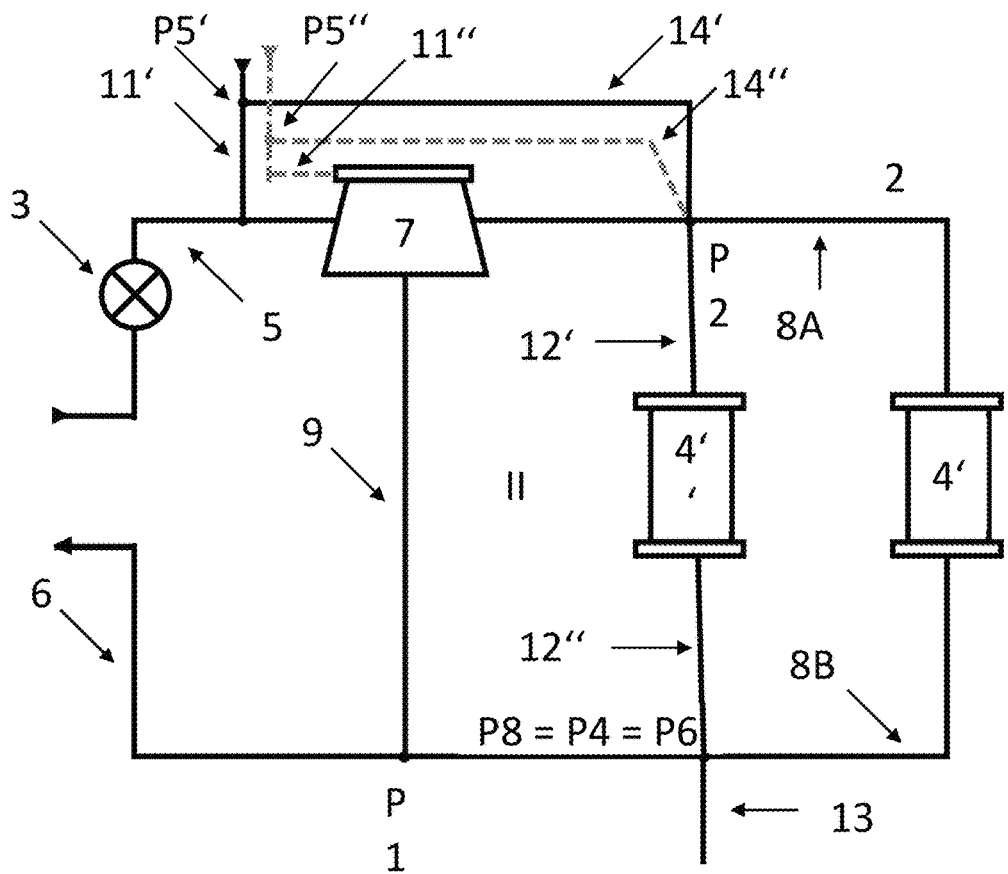
FIG. 15: Schematic illustration of an embodiment of the apheresis device according to the invention for extracorporeal removal of CRP from blood. The arterial line (5), in which there is a means (3) for generation and regulation of a flow of blood (e.g. peristaltic pump), leads the blood of a patient to the cell separator (7, e.g. a centrifugal cell separator). From this, the plasma line (8A) leads to the apheresis column (4') for affinity chromatographic removal of CRP. The bypass line section (12') of the bypass line (12) branches off from the plasma line (8A), leads to the apheresis column (4") for affinity chromatographic removal of CRP from blood. From the apheresis column (4"), the bypass line section (12") of the bypass line (12) for CRP-depleted blood plasma leads to the nodal point (P1), and from the apheresis column (4'), the plasma line (8B) for CRP-depleted blood plasma leads to the nodal point (P1). Another line, the cell line (9), leads from the cell separator (7) to the nodal point (P1). The venous line (6), which leads the treated blood back to the patient, also goes off from the nodal point (P1). In addition, there is a connection line (11') that runs into the arterial line (5) but could also have run directly into the cell separator (7), as well as a connection line (11") that runs into the cell separator (7) but could also have run into the arterial line (5). The bypass line section (12') of the bypass line (12) and the plasma line (8A) diverge at the nodal point (P2) and at the nodal point (P6) the plasma line (8B') and the plasma line (8B") converge. The waste line (12) branches off from the extracorporeal circulation system (2) at the nodal point (P6). In addition, a first regeneration line (14'), which branches off from the connection line (11') at the point (P5'), and a second regeneration line (14"), which branches off from the connection line (11") at the point (P5"), both run into the extracorporeal circulation system (2) at the nodal point (P2). For improved clarity, the central processing unit (10), which is also part of the apheresis device according to the invention, is not shown.
Figure 16:
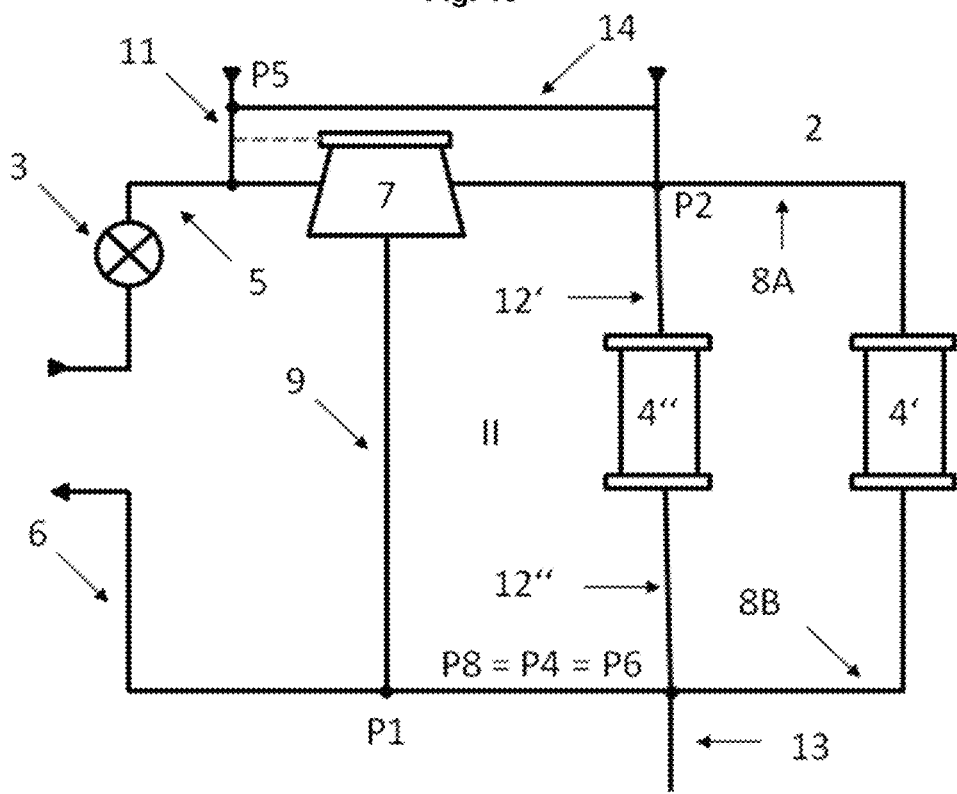
FIG. 16: Schematic illustration of an embodiment of the apheresis device according to the invention for extracorporeal removal of CRP from blood. The arterial line (5), in which there is a means (3) for generation and regulation of a flow of blood (e.g. peristaltic pump), leads the blood of a patient to the cell separator (7, e.g. a centrifugal cell separator). From this the plasma line (8A) leads to the apheresis column (4') for affinity chromatographic removal of CRP. The bypass line section (12') of the bypass line (12) branches off from the plasma line (8A), leads to the apheresis column (4") for affinity chromatographic removal of CRP from blood. From the apheresis column (4"), the bypass line section (12") of the bypass line (12) for CRP-depleted blood plasma leads to the nodal point (P1), and from the apheresis column (4'), the plasma line (8B) for CRP-depleted blood plasma leads to the nodal point (P1). Another line, the cell line (9), leads from the cell separator (7) to the nodal point (P1). The venous line (6), which leads the treated blood back to the patient, also goes off from the nodal point (P1). In addition, there is a connection line (11) for connection of a liquid container (F), which runs into the arterial line (5) or alternatively leads directly into the cell separator (7) (dashed line). The bypass line section (12') of the bypass line (12) and the plasma line (8A) diverge at the nodal point (P2) and at the nodal point (P6) the bypass line section (12") of the bypass line (12) and the plasma line (8B) converge. The waste line (13) branches off from the extracorporeal circulation system (2) at the nodal point (P6). In addition, the regeneration line (14), which branches off from the connection line (11) at the point (P5), runs into the extracorporeal circulation system (2) at the nodal point (P2). This time, the inlet line has an additional connection for a liquid container, wherein this connection is located after the cell separator (7) in the direction of flow, so that liquid from this additional liquid container cannot be fed into the cell separator (7) and cannot be fed into the arterial line (5) before the cell separator (7), but only into the bypass line section (12') of the bypass line (12) or into the plasma line (8A) in the direction of flow after the cell separator (7) or directly into the apheresis column (4') or directly into the apheresis column (4"). For improved clarity, the central processing unit (10), which is also part of the apheresis device according to the invention, is not shown.

1—apheresis device
2—extracorporeal circulation system
3—means for generation and regulation of a flow of blood (or blood plasma) in the extracorporeal circulation system (pump)
4—apheresis column for affinity chromatographic removal of CRP
4'—apheresis column for affinity chromatographic removal of CRP
4"—apheresis column for affinity chromatographic removal of CRP
5—arterial line
6—venous line
7—cell separator
8A—plasma line (before the apheresis column)
8B—plasma line (after the apheresis column)
9—cell line
10—central processing unit (CPU)
11—connection line
12—bypass line
12'—bypass line section of the bypass line
12"—bypass line section of the bypass line
13—waste line
13'—waste line
13"—waste line
14—regeneration line
14'—regeneration line
14"—regeneration line
F—liquid container
F1—liquid container 1
F2—liquid container 2
P1—nodal point at which the plasma line (8B) merges into the venous line (6) or nodal point at which the bypass line section (12") of the bypass line (12) or (8B) and the cell line (9) converge and merge into the venous line (6)
P2—nodal point at which the bypass line (12) branches off from the plasma line (8A) or nodal point at which the bypass line section (12') of the bypass line and the plasma line (8B) diverge
P3—nodal point at which the bypass line (12) flows into the cell line (9)
P4—nodal point at which the waste line (13) branches off from the plasma line (8B) or nodal point at which the waste line (13') branches off from the plasma line (8B)
P5—nodal point at which the regeneration line (14) branches off from the connection line (11)
P5, P5'—nodal point at which the regeneration line (14) branches off from the connection line (11) or (11') respectively.
P6—nodal point at which the bypass line (12) runs into the plasma line (8B) or nodal point at which the bypass line section (12") of the bypass line (12) and the plasma line (8B) converge and run together as the bypass line section (12") of the bypass line (12) or (8B) to the point P1.
P7—nodal point in the regeneration line (14) from which the regeneration line (14) divides the lines (15') and (15").
P8—nodal point at which the waste line (13") branches off from the bypass line section (12") of the bypass line.

What is claimed is:

1. An apheresis device for extracorporeal removal of CRP from blood comprising:
   an extracorporeal circulation system for blood,
   means for generation and regulation of a flow of blood in the extracorporeal circulation system,
   a cell separator for separation of the blood into blood plasma and cellular components,
   at least one apheresis column for affinity chromatographic removal of CRP from blood,
   wherein the extracorporeal circulation system comprises an arterial line to the cell separator, a first plasma line from the cell separator to the apheresis column, a second plasma line for CRP-depleted blood plasma from the apheresis column to a point, a cell line for the separated cellular components from the cell separator to the point and a venous line starting from the point,
   a central processing unit for controlling the apheresis device,
   at least one connection line for connection of at least one liquid container to the arterial line or the cell separator,
   characterized in that
   a bypass line branches off from the first plasma line and runs into the second plasma line,
   a waste line goes off directly from the apheresis column or from the second plasma line in the direction of flow before the junction of the bypass line, and
   at least one regeneration line which goes off from the at least one liquid container or from the at least one connection line and leads to the first plasma line in a direction of flow at or after the branch of the bypass line or runs directly into the apheresis column.

2. The device according to claim 1, wherein the at least one regeneration line leading into the first plasma line or directly into the apheresis column, starts from a point in the at least one connection line.

3. The device according to claim 1, wherein the apheresis device has at least two connection lines each for connection of at least one liquid container to the arterial line or the cell separator, and wherein there is a regeneration line per liquid container which go off from the respective liquid container or its connection line and which each lead into the first plasma line or directly into the apheresis column.

4. The device according to claim 1, wherein the apheresis device has two connection lines each for connection of at least one liquid container to the arterial line or the cell separator, and wherein the at least one regeneration line leading into the first plasma line or directly into the apheresis column connects to the connection line at a point and to the connection line at a point.

5. The device according to claim 1, wherein the apheresis device has two connection lines each for connection of at least one liquid container to the arterial line or the cell separator, and wherein two regeneration lines go off from the two liquid containers or the two connection lines and lead into the first plasma line or directly into the apheresis column.

6. The device according to claim 1, wherein the apheresis device has a first connection line for connection of a liquid container to the arterial line or the cell separator and a second connection line for connection of a liquid container to the arterial line or the cell separator, and wherein a first regeneration line goes off from the liquid container or the first connection line and leads into the first plasma line in the direction of flow after the branch of the bypass line or directly into the apheresis column and a second regeneration line goes off from the liquid container or the second connection line and leads into the first plasma line in the direction of flow after the branch of the bypass line or into the first regeneration line or directly into the apheresis column.

7. The device according to claim 1, wherein the bypass line leads from a point in the first plasma line to a point in the second plasma line and the waste line goes off from a point from the second plasma line and the at least one regeneration line runs into the first plasma line at point.

8. An apheresis device for extracorporeal removal of CRP from blood comprising:
   an extracorporeal circulation system for blood,
   a means for generation and regulation of a flow of blood in the extracorporeal circulation system,
   a cell separator for separation of the blood into blood plasma and cellular components,
   two apheresis columns for affinity chromatographic removal of CRP from blood,
   wherein the extracorporeal circulation system comprises an arterial line to the cell separator, a first plasma line from the cell separator to a first apheresis column, a second plasma line for CRP-depleted blood plasma from the first apheresis column to a point, a cell line for the separated cellular components from the cell separator to the point and a venous line starting from the point,
   a central processing unit for controlling the apheresis device,
   at least one connection line for connection of at least one liquid container to the arterial line or the cell separator,
   characterized in that
   a bypass line branches off from the first plasma line and runs into the second plasma line, and the bypass line comprises a second apheresis column,
   a waste line goes off directly from the first apheresis column or from the second plasma line in the direction of flow before the junction of the bypass line, and
   at least one regeneration line which goes off from the at least one liquid container or from the at least one connection line and leads to the first plasma line in the direction of flow at or after the branch of the bypass line or runs directly into the first apheresis column, and
   wherein a second apheresis column is connected in parallel to the first apheresis column and both apheresis columns cannot be used simultaneously for CRP removal.

9. A method for regeneration of an apheresis column for affinity chromatographic removal of CRP in an apheresis device according to claim 1, the method enabling the regeneration during operation and being characterized by the following steps:
   (A) starting redirection of the separated plasma from the plasma line into the bypass line, thereby stopping the introduction of the separated plasma from the plasma line into the apheresis column,
   (B) starting introduction of regeneration solution via the at least one regeneration line into the plasma line or directly into the apheresis column,
   (C) starting redirection of the liquid flow exiting the apheresis column from the plasma line into the waste line,
   (D) stopping the introduction of regeneration solution and stopping the redirection of the separated plasma from the plasma line into the bypass line, thereby introducing the separated plasma from the plasma line into the apheresis column, (E) closing the waste line and forwarding the liquid flow exiting the apheresis column into the venous line.

10. The method according to claim 9 for regeneration of an apheresis column for affinity chromatographic removal of CRP in an apheresis device according to claim 1, the method being characterized by the following steps:
(A) starting redirection of the separated plasma from the plasma line into the bypass line, thereby stopping the introduction of the separated plasma from the plasma line into the apheresis column,
(B) starting introduction of rinsing solution via the at least one regeneration line into the plasma line or directly into the apheresis column,
(C) stopping the introduction of rinsing solution and transition to the introduction of a regeneration solution via the at least one regeneration line into the plasma line or directly into the apheresis column,
(D) starting the redirection of the liquid flow exiting the apheresis column from the plasma line into the waste line,
(E) stopping the introduction of regeneration solution and transition to the introduction of the rinsing solution via the at least one regeneration line into the plasma line or directly into the apheresis column,
(F) closing the waste line and forwarding the liquid flow exiting the apheresis column into the venous line,
(G) stopping the introduction of rinsing solution and stopping the redirection of the separated plasma from the plasma line into the bypass line, thereby directing the separated plasma from the plasma line into the apheresis column.

11. The method according to claim 9, wherein the regeneration solution(s) are selected from the group comprising or consisting of citrate solution, TRIS-glycine solution, NaCl solution, full electrolyte solution and EDTA solution and especially citrate solution.

12. The method according to claim 9, wherein the rinsing solution is a physiological NaCl solution and/or the regeneration solution is a citrate solution.

13. The method according to claim 12, wherein step (C) is initiated after a total volume X of regeneration solution(s) has been introduced into the plasma line or directly into the apheresis column, wherein X corresponds at least 75% of the volume of the device between the point at which the regeneration line runs into the extracorporeal circulation system in the direction of flow after the branching of the bypass line and the point at which the waste line originates from the extracorporeal circulation system.

14. A method for regeneration of an apheresis column for affinity chromatographic removal of CRP during operation of a second apheresis column in an apheresis device according to claim 8 comprising the following steps:
(A) beginning with the flow of blood plasma through the apheresis column, starting introduction of the separated plasma from the plasma line into the apheresis column and directing the CRP-depleted blood plasma into the venous line, thereby stopping the introduction of the separated plasma via the bypass line section of the bypass line into the apheresis column,
(B) starting the introduction of regeneration solution via the at least one regeneration line into the bypass line section of the bypass line or directly into the apheresis column,
(C) starting redirection of the liquid flow exiting the apheresis column from the bypass line section of the bypass line into the waste line,
(D) starting introduction of the separated plasma via the bypass line section of the bypass line into the apheresis column and directing the CRP-depleted blood plasma into the venous line, thereby stopping the introduction of the separated plasma via the plasma line into the apheresis column,
(E) closing the waste line and starting redirection of the liquid flow exiting the apheresis column from the plasma line into the waste line.

* * * * *